United States Patent
Schaller

(10) Patent No.: US 7,666,226 B2
(45) Date of Patent: Feb. 23, 2010

(54) SPINAL TISSUE DISTRACTION DEVICES

(75) Inventor: Laurent Schaller, Los Altos, CA (US)

(73) Assignee: Benvenue Medical, Inc., Santa Clara, CA (US)

( * ) Notice: Subject to any disclaimer, the term of this patent is extended or adjusted under 35 U.S.C. 154(b) by 89 days.

(21) Appl. No.: 11/464,790

(22) Filed: Aug. 15, 2006

(65) Prior Publication Data
US 2007/0055272 A1     Mar. 8, 2007

Related U.S. Application Data

(60) Provisional application No. 60/708,691, filed on Aug. 16, 2005, provisional application No. 60/738,432, filed on Nov. 21, 2005, provisional application No. 60/784,185, filed on Mar. 21, 2006.

(51) Int. Cl.
*A61F 2/44*     (2006.01)
(52) U.S. Cl. .................................. 623/17.11
(58) Field of Classification Search ................... 606/90, 606/92, 105; 623/17.11–17.16
See application file for complete search history.

(56) References Cited

U.S. PATENT DOCUMENTS

| | | |
|---|---|---|
| 1,965,653 A | 7/1934 | Kennedy |
| 3,091,237 A | 5/1963 | Skinner |
| 3,112,743 A | 12/1963 | Cochran et al. |
| 3,648,294 A | 3/1972 | Shahrestani |
| 3,800,788 A | 4/1974 | White |
| 3,875,595 A | 4/1975 | Froning |
| 3,889,665 A | 6/1975 | Ling et al. |
| 3,964,480 A | 6/1976 | Froning |
| 4,262,676 A | 4/1981 | Jamshidi |
| 4,274,163 A | 6/1981 | Malcom et al. |
| 4,312,337 A | 1/1982 | Donohue |
| 4,313,434 A | 2/1982 | Segal |

(Continued)

FOREIGN PATENT DOCUMENTS

DE     19710392 C1     7/1999

(Continued)

OTHER PUBLICATIONS

PCT Invitation to Pay Additional Fees (Form PCT/ISA/206), Re: International application No. PCT/US2006/031861 dated Jan. 15, 2007.

(Continued)

*Primary Examiner*—Eduardo C Robert
*Assistant Examiner*—Julianna N Harvey
(74) *Attorney, Agent, or Firm*—Cook Alex Ltd.

(57) ABSTRACT

Spinal tissue distraction devices that include at least one guide member for guiding a distraction device to a location between layers of spinal tissue. The guide member has a proximal end portion and a distal end portion. The distal end portion is adapted for insertion between the tissue layers and defines a shape of a desired support structure. The distraction device is slidably mounted on the guide member for advancing the distraction device distally along the guide member for insertion of the distraction device between the tissue layers. The distraction device substantially conforms to the shape defined by the distal end portion of the guide member to form a support structure that separates, supports or both separates and supports the tissue layers.

14 Claims, 25 Drawing Sheets

U.S. PATENT DOCUMENTS

| | | | |
|---|---|---|---|
| 4,399,814 A | 8/1983 | Pratt, Jr. et al. |
| 4,462,394 A | 7/1984 | Jacobs |
| 4,466,435 A | 8/1984 | Murray |
| 4,467,479 A | 8/1984 | Brody |
| 4,488,549 A | 12/1984 | Lee et al. |
| 4,562,598 A | 1/1986 | Kranz |
| 4,595,006 A | 6/1986 | Burke et al. |
| 4,625,722 A | 12/1986 | Murray |
| 4,627,434 A | 12/1986 | Murray |
| 4,628,945 A | 12/1986 | Johnson, Jr. |
| 4,630,616 A | 12/1986 | Tretinyak |
| 4,665,906 A | 5/1987 | Jervis |
| 4,686,973 A | 8/1987 | Frisch |
| 4,697,584 A | 10/1987 | Haynes |
| 4,706,670 A | 11/1987 | Andersen et al. |
| 4,714,478 A | 12/1987 | Fischer |
| 4,743,256 A | 5/1988 | Brantigan |
| 4,772,287 A | 9/1988 | Ray et al. |
| 4,834,069 A | 5/1989 | Umeda |
| 4,838,282 A | 6/1989 | Strasser et al. |
| 4,863,476 A | 9/1989 | Shepperd |
| 4,878,915 A | 11/1989 | Brantigan |
| 4,888,022 A | 12/1989 | Huebsch |
| 4,888,024 A | 12/1989 | Powlan |
| 4,892,550 A | 1/1990 | Huebsch |
| 4,896,662 A | 1/1990 | Noble |
| 4,941,466 A | 7/1990 | Romano |
| 4,961,740 A | 10/1990 | Ray et al. |
| 4,969,888 A | 11/1990 | Scholten et al. |
| 5,015,247 A | 5/1991 | Michelson |
| 5,015,255 A | 5/1991 | Kuslich |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,071,435 A | 12/1991 | Fuchs et al. |
| 5,098,435 A | 3/1992 | Stednitz et al. |
| 5,102,413 A | 4/1992 | Poddar |
| 5,108,404 A | 4/1992 | Scholten et al. |
| 5,122,130 A | 6/1992 | Keller |
| 5,123,926 A | 6/1992 | Pisharodi |
| 5,147,366 A | 9/1992 | Arroyo et al. |
| 5,163,989 A | 11/1992 | Campbell et al. |
| 5,171,280 A | 12/1992 | Baumgartner |
| 5,176,683 A | 1/1993 | Kimsey et al. |
| 5,176,692 A | 1/1993 | Wilk et al. |
| 5,183,052 A | 2/1993 | Terwilliger |
| 5,192,327 A | 3/1993 | Brantigan |
| 5,242,879 A | 9/1993 | Abe et al. |
| 5,257,632 A | 11/1993 | Turkel et al. |
| 5,263,953 A | 11/1993 | Bagby |
| 5,303,718 A | 4/1994 | Krajicek |
| 5,306,308 A | 4/1994 | Gross et al. |
| 5,306,310 A | 4/1994 | Siebels |
| 5,322,505 A | 6/1994 | Krause et al. |
| 5,330,429 A | 7/1994 | Noguchi et al. |
| 5,331,975 A | 7/1994 | Bonutti |
| 5,361,752 A | 11/1994 | Moll et al. |
| 5,383,932 A | 1/1995 | Wilson et al. |
| 5,385,151 A | 1/1995 | Scarfone et al. |
| 5,423,816 A | 6/1995 | Lin |
| 5,423,817 A | 6/1995 | Lin |
| 5,423,850 A | 6/1995 | Berger |
| 5,431,658 A | 7/1995 | Moskovich |
| 5,441,538 A | 8/1995 | Bonutti |
| 5,454,365 A | 10/1995 | Bonutti |
| 5,454,827 A | 10/1995 | Aust et al. |
| 5,462,563 A | 10/1995 | Shearer et al. |
| 5,468,245 A | 11/1995 | Vargas, III |
| 5,480,400 A | 1/1996 | Berger |
| 5,484,437 A | 1/1996 | Michelson |
| 5,509,923 A | 4/1996 | Middleman et al. |
| 5,514,143 A | 5/1996 | Bonutti et al. |
| 5,514,153 A | 5/1996 | Bonutti |
| 5,522,398 A | 6/1996 | Goldenberg et al. |
| 5,522,790 A | 6/1996 | Moll et al. |
| 5,522,846 A | 6/1996 | Bonutti |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,538,009 A | 7/1996 | Byrne et al. |
| 5,540,711 A | 7/1996 | Kieturakis et al. |
| 5,545,222 A | 8/1996 | Bonutti |
| 5,549,679 A | 8/1996 | Kuslich |
| 5,562,736 A | 10/1996 | Ray et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,593,409 A | 1/1997 | Michelson |
| 5,601,556 A | 2/1997 | Pisharodi |
| 5,601,572 A | 2/1997 | Middleman et al. |
| 5,632,746 A | 5/1997 | Middleman et al. |
| 5,645,597 A | 7/1997 | Krapiva |
| 5,665,122 A | 9/1997 | Kambin |
| 5,669,926 A | 9/1997 | Aust et al. |
| 5,674,295 A | 10/1997 | Ray et al. |
| 5,681,263 A | 10/1997 | Flesch |
| 5,693,100 A | 12/1997 | Pisharodi |
| 5,695,513 A | 12/1997 | Johnson et al. |
| 5,700,239 A | 12/1997 | Yoon |
| 5,702,453 A | 12/1997 | Rabbe et al. |
| 5,702,454 A | 12/1997 | Baumgartner |
| 5,716,416 A | 2/1998 | Lin |
| 5,741,253 A | 4/1998 | Michelson |
| 5,749,879 A | 5/1998 | Middleman et al. |
| 5,755,797 A | 5/1998 | Baumgartner |
| 5,772,661 A | 6/1998 | Michelson |
| 5,782,832 A | 7/1998 | Larsen et al. |
| 5,788,703 A | 8/1998 | Mittelmeier et al. |
| 5,807,275 A | 9/1998 | Jamshidi |
| 5,820,628 A | 10/1998 | Middleman et al. |
| 5,823,979 A | 10/1998 | Mezo |
| 5,824,093 A | 10/1998 | Ray et al. |
| 5,827,289 A | 10/1998 | Reiley et al. |
| 5,836,948 A | 11/1998 | Zucherman et al. |
| 5,851,212 A | 12/1998 | Zirps et al. |
| 5,860,977 A | 1/1999 | Zucherman et al. |
| 5,865,848 A | 2/1999 | Baker |
| 5,904,690 A | 5/1999 | Middleman et al. |
| 5,919,235 A | 7/1999 | Husson et al. |
| 5,925,074 A | 7/1999 | Gingras et al. |
| 5,961,554 A | 10/1999 | Janson et al. |
| 5,972,015 A | 10/1999 | Scribner et al. |
| 5,976,186 A | 11/1999 | Bao et al. |
| 5,980,522 A | 11/1999 | Koros et al. |
| 6,015,436 A | 1/2000 | Schonhoffer |
| 6,019,793 A | 2/2000 | Perren et al. |
| 6,030,401 A | 2/2000 | Marino |
| 6,033,406 A | 3/2000 | Mathews |
| 6,033,412 A | 3/2000 | Losken et al. |
| 6,039,740 A | 3/2000 | Olerud |
| 6,045,552 A | 4/2000 | Zucherman et al. |
| 6,048,342 A | 4/2000 | Zucherman et al. |
| 6,048,346 A | 4/2000 | Reiley et al. |
| 6,048,360 A | 4/2000 | Khosravi et al. |
| 6,066,154 A | 5/2000 | Reiley et al. |
| 6,068,630 A | 5/2000 | Zucherman et al. |
| 6,083,225 A | 7/2000 | Winslow et al. |
| 6,090,143 A | 7/2000 | Meriwether et al. |
| 6,102,950 A | 8/2000 | Vaccaro |
| 6,110,210 A | 8/2000 | Norton et al. |
| 6,113,640 A | 9/2000 | Tormala et al. |

| | | | | | | |
|---|---|---|---|---|---|---|
| 6,119,044 | A | 9/2000 | Kuzma | 6,582,431 B1 | 6/2003 | Ray |
| 6,123,705 | A | 9/2000 | Michelson | 6,582,433 B1 | 6/2003 | Yun |
| 6,126,660 | A | 10/2000 | Dietz | 6,595,998 B2 | 7/2003 | Johnson et al. |
| 6,127,597 | A | 10/2000 | Beyar et al. | 6,602,293 B1 | 8/2003 | Biermann et al. |
| 6,159,211 | A | 12/2000 | Boriani et al. | 6,607,544 B1 | 8/2003 | Boucher et al. |
| 6,159,244 | A | 12/2000 | Suddaby | 6,610,094 B2 | 8/2003 | Husson |
| 6,165,218 | A | 12/2000 | Husson et al. | 6,613,054 B2 | 9/2003 | Scribner et al. |
| 6,174,337 | B1 | 1/2001 | Keenan | 6,620,196 B1 | 9/2003 | Trieu |
| 6,179,873 | B1 | 1/2001 | Zientek | 6,623,505 B2 | 9/2003 | Scribner et al. |
| 6,187,048 | B1 | 2/2001 | Milner et al. | D482,787 S | 11/2003 | Reiss |
| 6,190,414 | B1 | 2/2001 | Young et al. | 6,641,587 B2 | 11/2003 | Scribner et al. |
| 6,193,757 | B1 | 2/2001 | Foley et al. | 6,645,213 B2 | 11/2003 | Sand et al. |
| 6,197,033 | B1 | 3/2001 | Haid, Jr. et al. | 6,648,917 B2 | 11/2003 | Gerbec et al. |
| D439,980 | S | 4/2001 | Reiley et al. | D483,495 S | 12/2003 | Sand |
| 6,217,579 | B1 | 4/2001 | Koros | 6,656,178 B1 | 12/2003 | Veldhuizen et al. |
| 6,221,082 | B1 | 4/2001 | Marino et al. | 6,656,180 B2 | 12/2003 | Stahurski |
| 6,224,603 | B1 | 5/2001 | Marino | 6,660,037 B1 | 12/2003 | Husson et al. |
| 6,235,030 | B1 | 5/2001 | Zucherman et al. | 6,663,647 B2 | 12/2003 | Reiley et al. |
| 6,235,043 | B1 | 5/2001 | Reiley et al. | 6,666,890 B2 | 12/2003 | Michelson |
| 6,238,491 | B1 | 5/2001 | Davidson et al. | 6,666,891 B2 | 12/2003 | Boehm, Jr. et al. |
| 6,241,734 | B1 | 6/2001 | Scribner et al. | 6,676,663 B2 | 1/2004 | Higueras et al. |
| 6,248,110 | B1 | 6/2001 | Reiley et al. | 6,676,665 B2 | 1/2004 | Foley et al. |
| 6,251,140 | B1 | 6/2001 | Marino et al. | 6,682,561 B2 | 1/2004 | Songer et al. |
| 6,261,289 | B1 | 7/2001 | Levy | 6,685,742 B1 | 2/2004 | Jackson |
| 6,264,695 | B1 | 7/2001 | Stoy | 6,689,125 B1 | 2/2004 | Keith et al. |
| 6,267,763 | B1 | 7/2001 | Castro | 6,689,168 B2 | 2/2004 | Lieberman |
| 6,280,456 | B1 | 8/2001 | Scribner et al. | 6,692,563 B2 | 2/2004 | Zimmermann |
| 6,280,475 | B1 | 8/2001 | Bao et al. | 6,706,070 B1 | 3/2004 | Wagner et al. |
| 6,290,724 | B1 | 9/2001 | Marino | 6,716,216 B1 | 4/2004 | Boucher et al. |
| D449,691 | S | 10/2001 | Reiley et al. | 6,716,247 B2 | 4/2004 | Michelson |
| 6,296,647 | B1 | 10/2001 | Robioneck et al. | 6,716,957 B2 | 4/2004 | Tunc |
| 6,312,443 | B1 | 11/2001 | Stone | 6,719,761 B1 | 4/2004 | Reiley et al. |
| 6,364,828 | B1 | 4/2002 | Yeung et al. | 6,719,773 B1 | 4/2004 | Boucher et al. |
| 6,368,325 | B1 | 4/2002 | McKinley et al. | 6,723,128 B2 | 4/2004 | Uk |
| 6,387,130 | B1 | 5/2002 | Stone et al. | 6,726,691 B2 | 4/2004 | Osorio et al. |
| 6,402,750 | B1 | 6/2002 | Atkinson et al. | D490,159 S | 5/2004 | Sand |
| 6,419,705 | B1 | 7/2002 | Erickson | 6,740,093 B2 | 5/2004 | Hochschuler et al. |
| 6,423,071 | B1 | 7/2002 | Lawson | D492,032 S | 6/2004 | Muller et al. |
| 6,423,083 | B2 | 7/2002 | Reiley et al. | 6,755,841 B2 | 6/2004 | Fraser et al. |
| 6,423,089 | B1 | 7/2002 | Gingras et al. | D492,775 S | 7/2004 | Doelling et al. |
| 6,425,919 | B1 | 7/2002 | Lambrecht | D493,533 S | 7/2004 | Blain |
| 6,428,541 | B1 | 8/2002 | Boyd et al. | 6,758,673 B2 | 7/2004 | Fromovich et al. |
| 6,436,140 | B1 | 8/2002 | Liu et al. | 6,764,514 B1 | 7/2004 | Li et al. |
| 6,440,138 | B1 | 8/2002 | Reiley et al. | D495,417 S | 8/2004 | Doelling et al. |
| 6,451,019 | B1 | 9/2002 | Zucherman et al. | 6,773,460 B2 | 8/2004 | Jackson |
| 6,468,279 | B1 | 10/2002 | Reo | 6,783,530 B1 | 8/2004 | Levy |
| 6,478,805 | B1 | 11/2002 | Marino et al. | 6,793,679 B2 | 9/2004 | Michelson |
| 6,482,235 | B1 | 11/2002 | Lambrecht et al. | 6,796,983 B1 | 9/2004 | Zucherman et al. |
| 6,485,518 | B1 | 11/2002 | Cornwall et al. | 6,805,695 B2 | 10/2004 | Keith et al. |
| D467,657 | S | 12/2002 | Scribner | 6,808,537 B2 | 10/2004 | Michelson |
| 6,488,710 | B2 | 12/2002 | Besselink | 6,814,736 B2 | 11/2004 | Reiley et al. |
| 6,491,626 | B1 | 12/2002 | Stone et al. | 6,814,756 B1 | 11/2004 | Michelson |
| 6,491,695 | B1 | 12/2002 | Roggenbuck | 6,821,298 B1 | 11/2004 | Jackson |
| 6,498,421 | B1 * | 12/2002 | Oh et al. ............... 310/323.18 | 6,830,589 B2 | 12/2004 | Erickson |
| 6,500,178 | B2 | 12/2002 | Zucherman et al. | 6,835,205 B2 | 12/2004 | Atkinson et al. |
| 6,500,205 | B1 | 12/2002 | Michelson | 6,835,206 B2 | 12/2004 | Jackson |
| 6,508,839 | B1 | 1/2003 | Lambrecht et al. | 6,840,944 B2 | 1/2005 | Suddaby |
| 6,511,471 | B2 | 1/2003 | Rosenman et al. | 6,852,126 B2 | 2/2005 | Ahlgren |
| 6,512,958 | B1 | 1/2003 | Swoyer et al. | 6,852,129 B2 | 2/2005 | Gerbec et al. |
| D469,871 | S | 2/2003 | Sand | 6,863,668 B2 | 3/2005 | Gillespie et al. |
| 6,520,991 | B2 | 2/2003 | Huene | 6,863,672 B2 | 3/2005 | Reiley et al. |
| D472,323 | S | 3/2003 | Sand | 6,863,673 B2 | 3/2005 | Gerbec et al. |
| 6,530,930 | B1 | 3/2003 | Marino et al. | 6,866,682 B1 | 3/2005 | An et al. |
| 6,533,791 | B1 | 3/2003 | Betz et al. | 6,881,228 B2 | 4/2005 | Zdeblick et al. |
| 6,533,797 | B1 | 3/2003 | Stone et al. | 6,883,520 B2 | 4/2005 | Lambrecht et al. |
| 6,540,747 | B1 | 4/2003 | Marino | 6,887,248 B2 | 5/2005 | McKinley et al. |
| 6,554,833 | B2 | 4/2003 | Levy et al. | 6,893,466 B2 | 5/2005 | Trieu |
| 6,558,390 | B2 | 5/2003 | Cragg | 6,899,716 B2 | 5/2005 | Cragg |
| 6,562,074 | B2 | 5/2003 | Gerbec et al. | 6,899,719 B2 | 5/2005 | Reiley et al. |
| 6,575,919 | B1 | 6/2003 | Reiley et al. | D506,828 S | 6/2005 | Layne et al. |
| 6,575,979 | B1 | 6/2003 | Cragg | 6,905,512 B2 | 6/2005 | Paes et al. |
| 6,576,016 | B1 | 6/2003 | Hochshuler et al. | 6,908,506 B2 | 6/2005 | Zimmermann |
| 6,579,291 | B1 | 6/2003 | Keith et al. | 6,921,403 B2 | 7/2005 | Cragg et al. |

| | | |
|---|---|---|
| 6,923,810 B1 | 8/2005 | Michelson |
| 6,923,813 B2 | 8/2005 | Phillips et al. |
| 6,923,814 B1 | 8/2005 | Hildebrand et al. |
| 6,929,647 B2 | 8/2005 | Cohen |
| 6,945,973 B2 | 9/2005 | Bray |
| 6,952,129 B2 | 10/2005 | Lin et al. |
| 6,962,606 B2 | 11/2005 | Michelson |
| 6,964,674 B1 | 11/2005 | Matsuura et al. |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,008,453 B1 | 3/2006 | Michelson |
| 7,014,633 B2 | 3/2006 | Cragg |
| 7,018,089 B2 | 3/2006 | Wenz et al. |
| 7,018,415 B1 | 3/2006 | McKay |
| 7,018,453 B2 | 3/2006 | Klein et al. |
| 7,029,498 B2 | 4/2006 | Boehm et al. |
| 7,044,954 B2 | 5/2006 | Reiley et al. |
| 7,063,703 B2 | 6/2006 | Reo |
| 7,066,961 B2 | 6/2006 | Michelson |
| 7,069,087 B2 | 6/2006 | Sharkey et al. |
| 7,070,598 B2 | 7/2006 | Lim et al. |
| 7,074,226 B2 | 7/2006 | Roehm, III et al. |
| 7,081,120 B2 | 7/2006 | Li et al. |
| 7,081,122 B1 | 7/2006 | Reiley et al. |
| 7,087,055 B2 | 8/2006 | Lim et al. |
| 7,094,257 B2 | 8/2006 | Mujwid et al. |
| 7,115,128 B2 | 10/2006 | Michelson |
| 7,115,163 B2 | 10/2006 | Zimmermann |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| 7,156,874 B2 | 1/2007 | Paponneau et al. |
| 7,156,875 B2 | 1/2007 | Michelson |
| 7,166,107 B2 | 1/2007 | Anderson |
| 7,179,293 B2 | 2/2007 | McKay |
| 7,189,242 B2 | 3/2007 | Boyd et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,220,281 B2 | 5/2007 | Lambrecht et al. |
| 7,223,227 B2 | 5/2007 | Pflueger |
| 7,226,481 B2 | 6/2007 | Kuslich |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,267,687 B2 | 9/2007 | McGuckin, Jr. |
| 7,270,679 B2 | 9/2007 | Istephanous et al. |
| 7,311,713 B2 | 12/2007 | Johnson et al. |
| 7,316,714 B2 | 1/2008 | Gordon et al. |
| 7,318,840 B2 | 1/2008 | McKay |
| 7,320,689 B2 | 1/2008 | Keller |
| 7,322,962 B2 | 1/2008 | Forrest |
| 7,383,639 B2 | 6/2008 | Malandain |
| 7,485,134 B2 | 2/2009 | Simonson |
| 2001/0011174 A1 | 8/2001 | Reiley et al. |
| 2001/0016741 A1 | 8/2001 | Burkus et al. |
| 2002/0016583 A1 | 2/2002 | Cragg |
| 2002/0026195 A1 | 2/2002 | Layne et al. |
| 2002/0026244 A1 | 2/2002 | Trieu |
| 2002/0045942 A1 | 4/2002 | Ham |
| 2002/0068974 A1 | 6/2002 | Kuslich et al. |
| 2002/0082608 A1 | 6/2002 | Reiley et al. |
| 2002/0087163 A1 | 7/2002 | Dixon et al. |
| 2002/0091390 A1 | 7/2002 | Michelson |
| 2002/0099385 A1 | 7/2002 | Ralph et al. |
| 2002/0107519 A1 | 8/2002 | Dixon et al. |
| 2002/0107573 A1 * | 8/2002 | Steinberg ................. 623/17.12 |
| 2002/0156482 A1 | 10/2002 | Scribner et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173851 A1 | 11/2002 | McKay |
| 2002/0183761 A1 | 12/2002 | Johnson et al. |
| 2002/0183778 A1 | 12/2002 | Reiley et al. |
| 2002/0191487 A1 | 12/2002 | Sand |
| 2003/0018390 A1 | 1/2003 | Husson |
| 2003/0032963 A1 | 2/2003 | Reiss et al. |
| 2003/0050644 A1 | 3/2003 | Boucher et al. |
| 2003/0074075 A1 * | 4/2003 | Thomas et al. ........... 623/17.16 |
| 2003/0108588 A1 | 6/2003 | Chen et al. |
| 2003/0130664 A1 | 7/2003 | Boucher et al. |
| 2003/0171812 A1 | 9/2003 | Grunberg et al. |
| 2003/0191414 A1 | 10/2003 | Reiley et al. |
| 2003/0191489 A1 | 10/2003 | Reiley et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0199979 A1 | 10/2003 | McGuckin, Jr. |
| 2003/0220648 A1 | 11/2003 | Osorio et al. |
| 2003/0220695 A1 | 11/2003 | Sevrain |
| 2003/0229372 A1 | 12/2003 | Reiley et al. |
| 2003/0233096 A1 | 12/2003 | Osorio et al. |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0019354 A1 | 1/2004 | Johnson et al. |
| 2004/0024408 A1 | 2/2004 | Burkus et al. |
| 2004/0024409 A1 | 2/2004 | Sand et al. |
| 2004/0024463 A1 | 2/2004 | Thomas, Jr. et al. |
| 2004/0024465 A1 | 2/2004 | Lambrecht et al. |
| 2004/0034429 A1 | 2/2004 | Lambrecht et al. |
| 2004/0049203 A1 | 3/2004 | Scribner et al. |
| 2004/0059333 A1 | 3/2004 | Carl et al. |
| 2004/0059339 A1 | 3/2004 | Roehm, III et al. |
| 2004/0059418 A1 | 3/2004 | McKay et al. |
| 2004/0064144 A1 | 4/2004 | Johnson et al. |
| 2004/0073308 A1 | 4/2004 | Kuslich et al. |
| 2004/0082953 A1 | 4/2004 | Petit |
| 2004/0087947 A1 | 5/2004 | Lim et al. |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0097924 A1 | 5/2004 | Lambrecht et al. |
| 2004/0097930 A1 | 5/2004 | Justis et al. |
| 2004/0097932 A1 | 5/2004 | Ray, III et al. |
| 2004/0098131 A1 | 5/2004 | Bryan et al. |
| 2004/0102774 A1 | 5/2004 | Trieu |
| 2004/0106940 A1 | 6/2004 | Shaolian et al. |
| 2004/0111161 A1 | 6/2004 | Trieu |
| 2004/0117019 A1 | 6/2004 | Trieu et al. |
| 2004/0133229 A1 | 7/2004 | Lambrecht et al. |
| 2004/0133280 A1 | 7/2004 | Trieu |
| 2004/0138748 A1 | 7/2004 | Boyer, II et al. |
| 2004/0153064 A1 | 8/2004 | Foley et al. |
| 2004/0153115 A1 | 8/2004 | Reiley et al. |
| 2004/0158206 A1 | 8/2004 | Aboul-Hosn et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0176775 A1 | 9/2004 | Burkus et al. |
| 2004/0186471 A1 | 9/2004 | Trieu |
| 2004/0186528 A1 | 9/2004 | Ries et al. |

| | | | | | |
|---|---|---|---|---|---|
| 2004/0186573 A1 | 9/2004 | Ferree | 2005/0182412 A1 | 8/2005 | Johnson et al. |
| 2004/0210231 A1 | 10/2004 | Boucher et al. | 2005/0182413 A1 | 8/2005 | Johnson et al. |
| 2004/0210310 A1 | 10/2004 | Trieu | 2005/0182414 A1 | 8/2005 | Manzi et al. |
| 2004/0215344 A1 | 10/2004 | Hochschuler et al. | 2005/0187556 A1 | 8/2005 | Stack et al. |
| 2004/0220580 A1 | 11/2004 | Johnson et al. | 2005/0187558 A1 | 8/2005 | Johnson et al. |
| 2004/0220672 A1 | 11/2004 | Shadduck | 2005/0187559 A1 | 8/2005 | Raymond et al. |
| 2004/0225296 A1 | 11/2004 | Reiss et al. | 2005/0187564 A1 | 8/2005 | Jayaraman |
| 2004/0225361 A1 | 11/2004 | Glenn et al. | 2005/0197707 A1 | 9/2005 | Trieu et al. |
| 2004/0230191 A1 | 11/2004 | Frey et al. | 2005/0216087 A1 | 9/2005 | Zucherman et al. |
| 2004/0230309 A1 | 11/2004 | DiMauro et al. | 2005/0222684 A1 | 10/2005 | Ferree |
| 2004/0249377 A1 | 12/2004 | Kaes et al. | 2005/0228383 A1 | 10/2005 | Zucherman et al. |
| 2004/0254520 A1 | 12/2004 | Porteous et al. | 2005/0228391 A1 | 10/2005 | Levy et al. |
| 2004/0254644 A1 | 12/2004 | Taylor | 2005/0228397 A1 | 10/2005 | Malandain et al. |
| 2004/0260300 A1 | 12/2004 | Gorensek et al. | 2005/0234425 A1 | 10/2005 | Miller et al. |
| 2004/0260397 A1 | 12/2004 | Lambrecht et al. | 2005/0234451 A1 | 10/2005 | Markworth |
| 2004/0267271 A9 | 12/2004 | Scribner et al. | 2005/0234452 A1 | 10/2005 | Malandain |
| 2005/0004578 A1 | 1/2005 | Lambrecht et al. | 2005/0234456 A1 | 10/2005 | Malandain |
| 2005/0010293 A1 | 1/2005 | Zucherman et al. | 2005/0240182 A1 | 10/2005 | Zucherman et al. |
| 2005/0010298 A1 | 1/2005 | Zucherman et al. | 2005/0240189 A1 | 10/2005 | Rousseau et al. |
| 2005/0015148 A1 | 1/2005 | Jansen et al. | 2005/0240193 A1 | 10/2005 | Layne et al. |
| 2005/0015152 A1 | 1/2005 | Sweeney | 2005/0240269 A1 | 10/2005 | Lambrecht et al. |
| 2005/0033295 A1 | 2/2005 | Wisnewski | 2005/0251149 A1 | 11/2005 | Wenz |
| 2005/0033440 A1 | 2/2005 | Lambrecht et al. | 2005/0251260 A1 | 11/2005 | Gerber et al. |
| 2005/0038517 A1 | 2/2005 | Carrison et al. | 2005/0261684 A1 | 11/2005 | Shaolian et al. |
| 2005/0043737 A1 | 2/2005 | Reiley et al. | 2005/0261695 A1 | 11/2005 | Cragg et al. |
| 2005/0043796 A1 | 2/2005 | Grant et al. | 2005/0261781 A1 | 11/2005 | Sennett et al. |
| 2005/0055097 A1 | 3/2005 | Grunberg et al. | 2005/0273166 A1 | 12/2005 | Sweeney |
| 2005/0060036 A1 | 3/2005 | Schultz et al. | 2005/0273173 A1 | 12/2005 | Gordon |
| 2005/0060038 A1 | 3/2005 | Lambrecht et al. | 2005/0278027 A1 | 12/2005 | Hyde, Jr. |
| 2005/0065519 A1 | 3/2005 | Michelson | 2005/0278029 A1 | 12/2005 | Trieu |
| 2005/0065609 A1 | 3/2005 | Wardlaw | 2005/0283244 A1 | 12/2005 | Gordon et al. |
| 2005/0069571 A1 | 3/2005 | Slivka et al. | 2005/0287071 A1 | 12/2005 | Wenz |
| 2005/0070908 A1 | 3/2005 | Cragg | 2006/0004456 A1 | 1/2006 | McKay |
| 2005/0070911 A1 | 3/2005 | Carrison et al. | 2006/0009779 A1 | 1/2006 | Collins et al. |
| 2005/0070913 A1 | 3/2005 | Milbocker et al. | 2006/0030850 A1 | 2/2006 | Keegan et al. |
| 2005/0071011 A1 | 3/2005 | Ralph et al. | 2006/0030943 A1 | 2/2006 | Peterman |
| 2005/0080488 A1 | 4/2005 | Schultz | 2006/0036241 A1 | 2/2006 | Siegal |
| 2005/0090833 A1 | 4/2005 | DiPoto | 2006/0036259 A1 | 2/2006 | Carl et al. |
| 2005/0090852 A1 | 4/2005 | Layne et al. | 2006/0036261 A1 | 2/2006 | McDonnell |
| 2005/0090899 A1 | 4/2005 | DiPoto | 2006/0036273 A1 | 2/2006 | Siegal |
| 2005/0107880 A1 | 5/2005 | Shimp et al. | 2006/0058807 A1 | 3/2006 | Landry et al. |
| 2005/0113918 A1 | 5/2005 | Messerli et al. | 2006/0058880 A1 | 3/2006 | Wysocki et al. |
| 2005/0113919 A1 | 5/2005 | Cragg et al. | 2006/0064171 A1 | 3/2006 | Trieu |
| 2005/0113928 A1 | 5/2005 | Cragg et al. | 2006/0069439 A1 | 3/2006 | Zucherman et al. |
| 2005/0118228 A1 | 6/2005 | Trieu | 2006/0069440 A1 | 3/2006 | Zucherman et al. |
| 2005/0119662 A1 | 6/2005 | Reiley et al. | 2006/0085002 A1 | 4/2006 | Trieu et al. |
| 2005/0119750 A1 | 6/2005 | Studer | 2006/0085009 A1 | 4/2006 | Truckai et al. |
| 2005/0119751 A1 | 6/2005 | Lawson | 2006/0089642 A1 | 4/2006 | Diaz et al. |
| 2005/0119752 A1 | 6/2005 | Williams et al. | 2006/0089646 A1 | 4/2006 | Bonutti |
| 2005/0119754 A1 | 6/2005 | Trieu et al. | 2006/0089654 A1 | 4/2006 | Lins et al. |
| 2005/0124989 A1 | 6/2005 | Suddaby | 2006/0089718 A1 | 4/2006 | Zucherman et al. |
| 2005/0124992 A1 | 6/2005 | Ferree | 2006/0089719 A1 | 4/2006 | Trieu |
| 2005/0124999 A1 | 6/2005 | Teitelbaum et al. | 2006/0095045 A1 | 5/2006 | Trieu |
| 2005/0125066 A1 | 6/2005 | McAfee | 2006/0095046 A1 | 5/2006 | Trieu et al. |
| 2005/0131267 A1 | 6/2005 | Talmadge | 2006/0095134 A1 | 5/2006 | Trieu et al. |
| 2005/0131268 A1 | 6/2005 | Talmadge | 2006/0095138 A1 | 5/2006 | Truckai et al. |
| 2005/0131269 A1 | 6/2005 | Talmadge | 2006/0100706 A1 | 5/2006 | Shadduck et al. |
| 2005/0131536 A1 | 6/2005 | Eisermann et al. | 2006/0106397 A1 | 5/2006 | Lins |
| 2005/0131540 A1 | 6/2005 | Trieu | 2006/0106459 A1 | 5/2006 | Truckai et al. |
| 2005/0131541 A1 | 6/2005 | Trieu | 2006/0122704 A1 | 6/2006 | Vresilovic et al. |
| 2005/0137602 A1 | 6/2005 | Assell et al. | 2006/0129244 A1 | 6/2006 | Ensign |
| 2005/0142211 A1 | 6/2005 | Wenz | 2006/0136064 A1 | 6/2006 | Sherman |
| 2005/0143763 A1 | 6/2005 | Ortiz et al. | 2006/0142858 A1 | 6/2006 | Colleran et al. |
| 2005/0143827 A1 | 6/2005 | Globerman et al. | 2006/0142864 A1 | 6/2006 | Cauthen |
| 2005/0149022 A1 | 7/2005 | Shaolian et al. | 2006/0149136 A1 | 7/2006 | Seto et al. |
| 2005/0149191 A1 | 7/2005 | Cragg et al. | 2006/0149237 A1 | 7/2006 | Markworth et al. |
| 2005/0149194 A1 | 7/2005 | Ahlgren | 2006/0149252 A1 | 7/2006 | Markworth et al. |
| 2005/0149197 A1 | 7/2005 | Cauthen | 2006/0149379 A1 | 7/2006 | Kuslich et al. |
| 2005/0154396 A1 | 7/2005 | Foley et al. | 2006/0149380 A1 | 7/2006 | Lotz et al. |
| 2005/0154463 A1 | 7/2005 | Trieu | 2006/0155379 A1 | 7/2006 | Heneveld, Sr. et al. |
| 2005/0165406 A1 | 7/2005 | Assell et al. | 2006/0161162 A1 | 7/2006 | Lambrecht et al. |
| 2005/0171539 A1 | 8/2005 | Braun et al. | 2006/0161166 A1 | 7/2006 | Johnson et al. |
| 2005/0171552 A1 | 8/2005 | Johnson et al. | 2006/0167553 A1 | 7/2006 | Cauthen, III et al. |

| | | |
|---|---|---|
| 2006/0173545 A1 | 8/2006 | Cauthen, III et al. |
| 2006/0178746 A1 | 8/2006 | Bartish, Jr., et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195191 A1 | 8/2006 | Sweeney, II et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0235423 A1 | 10/2006 | Cantu |
| 2006/0235521 A1 | 10/2006 | Zucherman et al. |
| 2006/0241663 A1 | 10/2006 | Rice et al. |
| 2006/0241770 A1 | 10/2006 | Rhoda et al. |
| 2006/0247770 A1 | 11/2006 | Peterman |
| 2006/0247771 A1 | 11/2006 | Peterman et al. |
| 2006/0247781 A1 | 11/2006 | Francis |
| 2006/0264896 A1 | 11/2006 | Palmer |
| 2006/0264939 A1 | 11/2006 | Zucherman et al. |
| 2006/0264945 A1 | 11/2006 | Edidin et al. |
| 2006/0265067 A1 | 11/2006 | Zucherman et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow |
| 2006/0282167 A1 | 12/2006 | Lambrecht et al. |
| 2006/0293662 A1 | 12/2006 | Boyer, II et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010889 A1 | 1/2007 | Francis |
| 2007/0032703 A1 | 2/2007 | Sankaran et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055237 A1 | 3/2007 | Edidin et al. |
| 2007/0055246 A1 | 3/2007 | Zucherman et al. |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0068329 A1 | 3/2007 | Phan et al. |
| 2007/0073292 A1 | 3/2007 | Kohm et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093899 A1 | 4/2007 | Dutoit et al. |
| 2007/0093906 A1 | 4/2007 | Hudgins et al. |
| 2007/0123986 A1 | 5/2007 | Schaller |
| 2007/0135922 A1 | 6/2007 | Trieu |
| 2007/0149978 A1 | 6/2007 | Shezifi et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0162127 A1 | 7/2007 | Peterman et al. |
| 2007/0167945 A1 | 7/2007 | Lange et al. |
| 2007/0168038 A1 | 7/2007 | Trieu |
| 2007/0179612 A1 | 8/2007 | Johnson et al. |
| 2007/0179615 A1 | 8/2007 | Heinz et al. |
| 2007/0179616 A1 | 8/2007 | Braddock, Jr., et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0208426 A1 | 9/2007 | Trieu |
| 2007/0213717 A1 | 9/2007 | Trieu et al. |
| 2007/0219634 A1 | 9/2007 | Greenhalgh et al. |
| 2007/0233074 A1 | 10/2007 | Anderson et al. |
| 2007/0260255 A1 | 11/2007 | Haddock et al. |
| 2007/0270957 A1 | 11/2007 | Heinz |
| 2007/0282443 A1 | 12/2007 | Globerman et al. |
| 2008/0021557 A1 | 1/2008 | Trieu |
| 2008/0027437 A1 | 1/2008 | Johnson et al. |
| 2008/0027453 A1 | 1/2008 | Johnson et al. |
| 2008/0027454 A1 | 1/2008 | Johnson et al. |
| 2008/0229597 A1 | 9/2008 | Malandain |
| 2008/0281346 A1 | 11/2008 | Greenhalgh et al. |
| 2008/0281364 A1 | 11/2008 | Chirico et al. |
| 2009/0048678 A1 | 2/2009 | Saal et al. |

FOREIGN PATENT DOCUMENTS

| | | |
|---|---|---|
| DE | 202006005868 | 6/2006 |
| EP | 0529275 A2 | 3/1993 |
| EP | 0 621 020 A1 | 10/1994 |
| EP | 1 157 676 A1 | 4/2001 |
| EP | 1157676 A1 | 11/2001 |
| WO | WO 01/10316 A1 | 2/2001 |
| WO | WO 02/17824 A2 | 3/2002 |
| WO | WO 02/30338 A1 | 4/2002 |
| WO | WO 02/43628 A1 | 6/2002 |
| WO | WO 02/47563 A1 | 6/2002 |
| WO | WO 02/071921 A2 | 9/2002 |
| WO | WO 03/007854 A1 | 1/2003 |
| WO | WO 03/020169 A2 | 3/2003 |
| WO | WO 03/022165 A1 | 3/2003 |
| WO | WO 03/028587 A2 | 4/2003 |
| WO | WO 03/059180 A2 | 7/2003 |
| WO | WO2004/034924 A2 | 4/2004 |
| WO | WO 2004/082526 A2 | 9/2004 |
| WO | WO 2004/108022 A1 | 12/2004 |
| WO | WO 2005/032433 A2 | 4/2005 |
| WO | WO 2005/051246 A2 | 6/2005 |
| WO | WO 2005/081877 A2 | 9/2005 |
| WO | WO 2006/047645 A2 | 5/2006 |
| WO | WO 2006/060420 A1 | 6/2006 |
| WO | WO 2006/066228 A2 | 6/2006 |

| WO | WO 2006/072941 A2 | 7/2006 |
| WO | WO 2007/022194 A2 | 2/2007 |
| WO | WO2007/067726 A2 | 6/2007 |

OTHER PUBLICATIONS

Annex to PCT Invitation to Pay Additional Fees, Re: International application No. PCT/US2006/031861 dated Jan. 15, 2007.

PCT Notification concerning transmittal of International Preliminary report on patentability and PCT Written Opinion of the International Searching Authority, PCT Application No. US2006/031861 dated Feb. 28, 2008.

John A. Carrino, Roxanne Chan and Alexander R. Vaccaro, "Vertebral Augmentation: Vertebroplasty and Kyphoplasty", Seminars in Roentgenology, vol. 39, No. 1 (Jan. 2004): pp. 68-84.

Ajeya P. Joshi, M.D. and Paul A. Glazer, M.D., "Vertebroplasty: Current Concepts and Outlook", 2003, (9 Pages), From: http://www.spineuniverse.com/displayarticle.php/article2076.html.

U.S. Appl. No. 11/464,782 (pending) to Schaller filed Aug. 15, 2006, entitled "Spinal Tissue Distraction Devices".

U.S. Appl. No. 11/464,793 (pending) to Schaller filed Aug. 15, 2006, entitled "Devices For Limiting The Movement Of Material Introduced Between Layers Of Spinal Tissue".

U.S. Appl. No. 11/464,807 (pending) to Schaller filed Aug. 15, 2006, entitled "Methods of Distracting Tissue Layers of the Human Spine".

U.S. Appl. No. 11/464,812 (pending) to Schaller filed Aug. 15, 2006, entitled "Methods of Distracting Tissue Layers of the Human Spine".

U.S. Appl. No. 11/464,815 (pending) to Schaller filed Aug. 15, 2006, entitled "Methods For Limiting The Movement Of Material Introduced Between Layers Of Spinal Tissue".

PCT/US2006/031861 (pending) to Schaller filed Aug. 15, 2006, entitled "Spinal Tissue Distraction Devices".

Notification of Transmittal of International Search Report, International Search Report and Written Opinion for PCT/US08/54590 dated Aug. 22, 2008.

Notification of Transmittal of International Search Report, International Search Report and Written Opinion for PCT/US08/54508 dated Aug. 27, 2008.

U.S. Appl. No. 60/689,570, filed Jun. 13, 2005; Inventor: Tzony Siegal: Title: Directional Drilling System.

USPTO Office Action of Aug. 19, 2009 for U.S. Appl. No. 11/464,807.

* cited by examiner

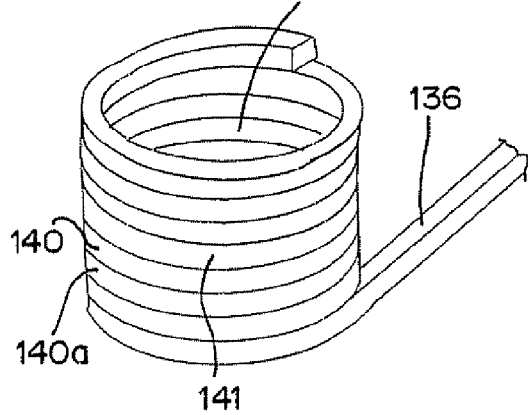
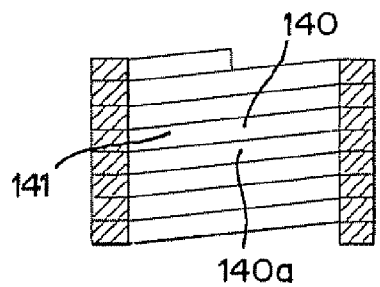
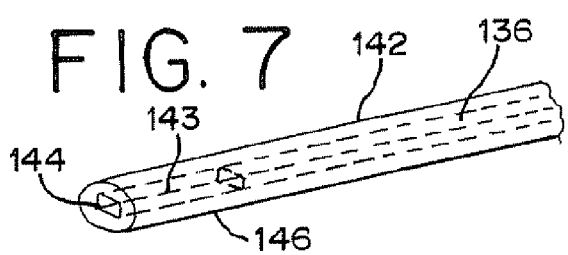
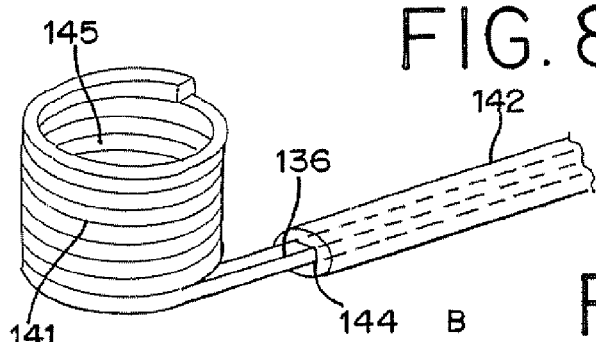
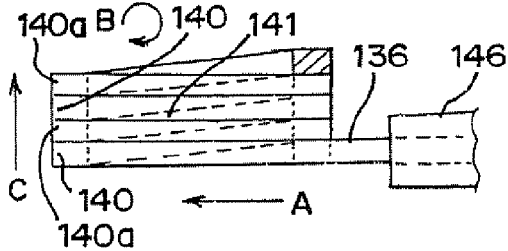
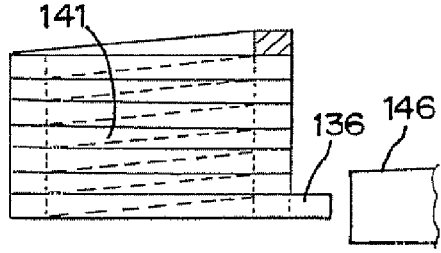

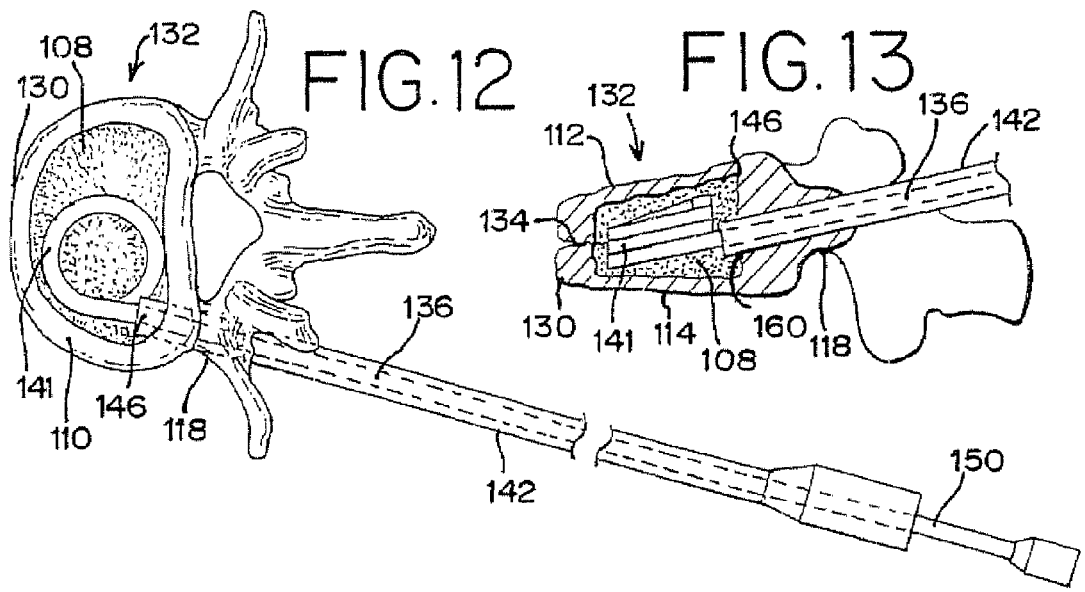
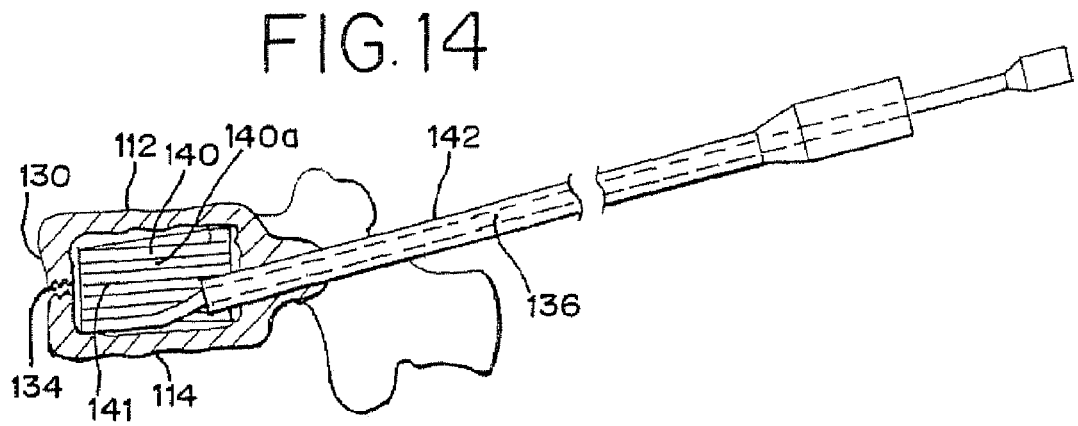
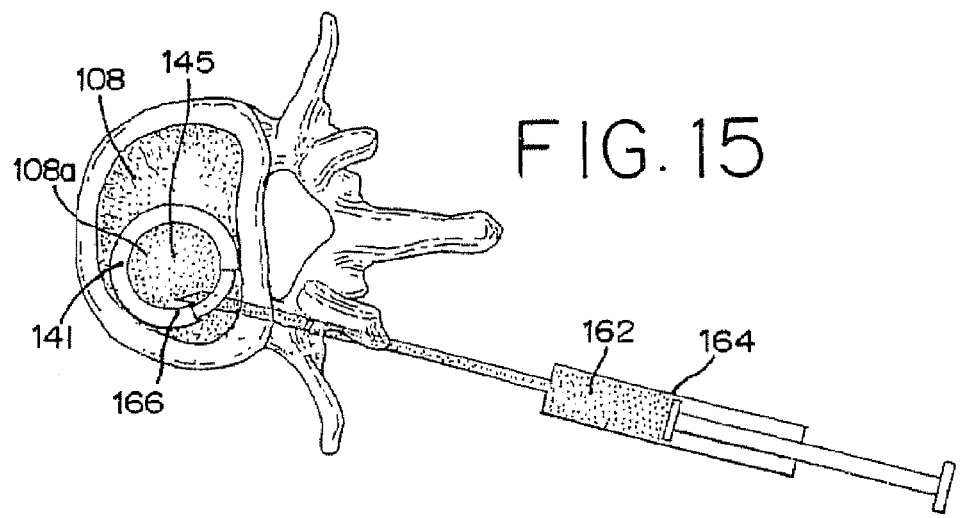

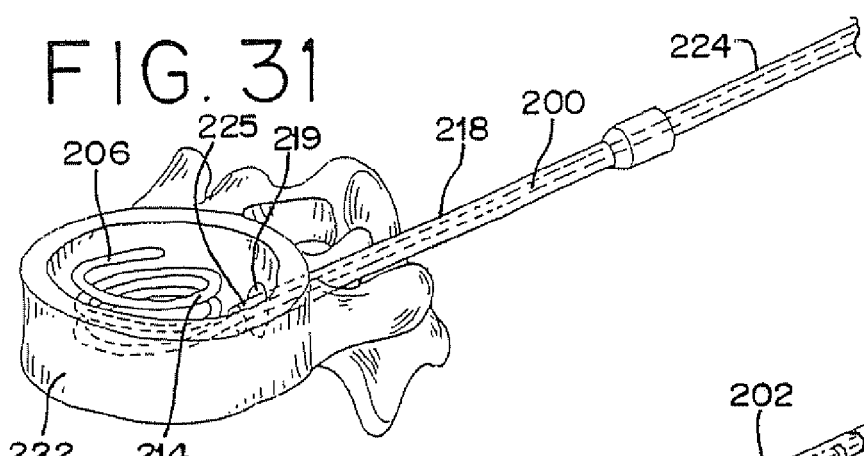
FIG. 31
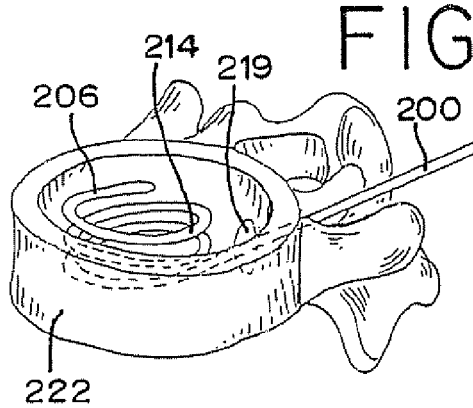
FIG. 32
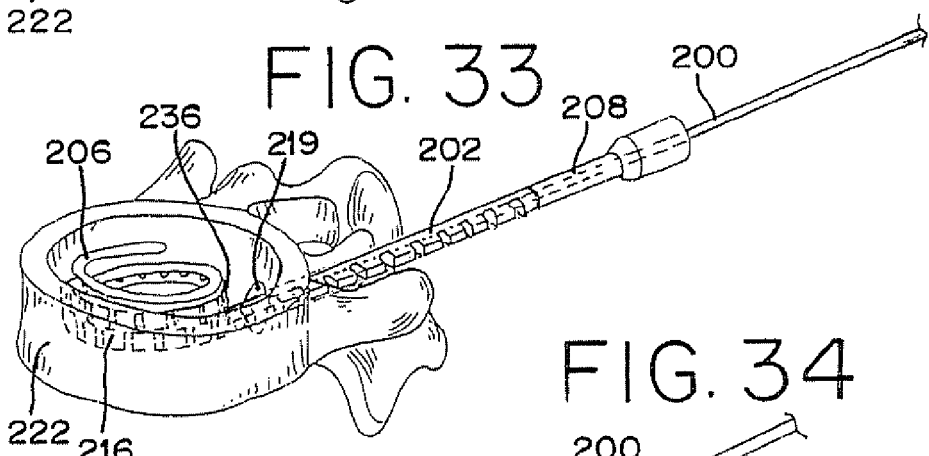
FIG. 33
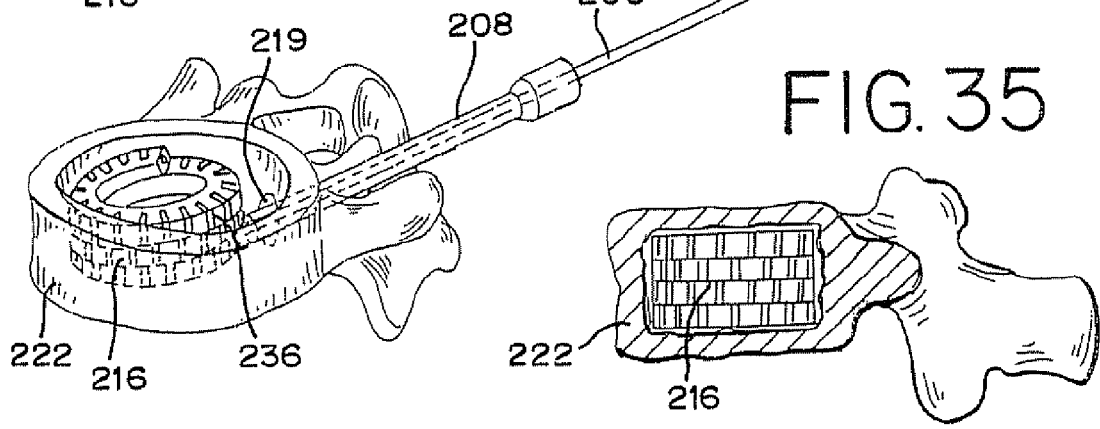
FIG. 34
FIG. 35

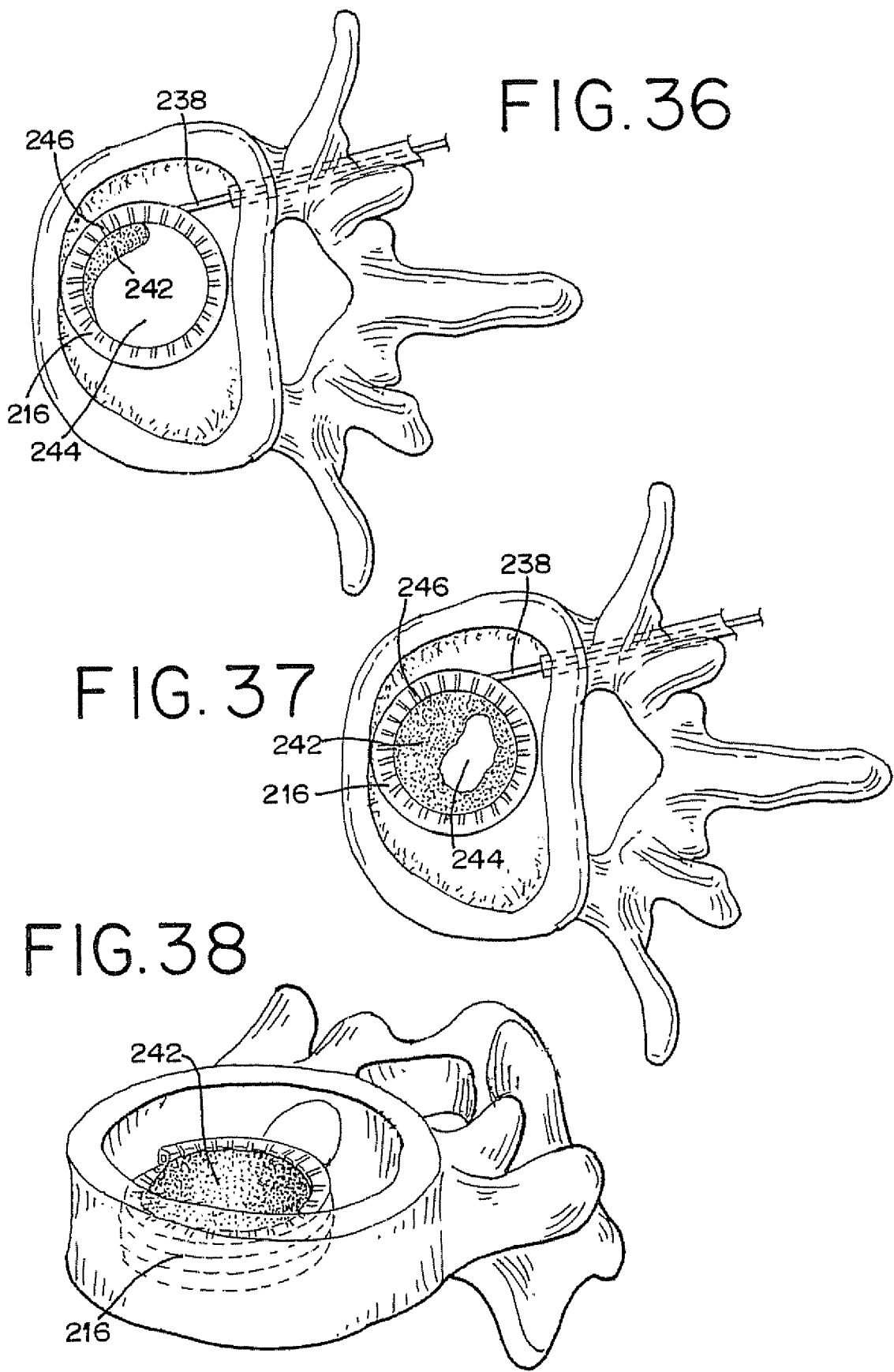

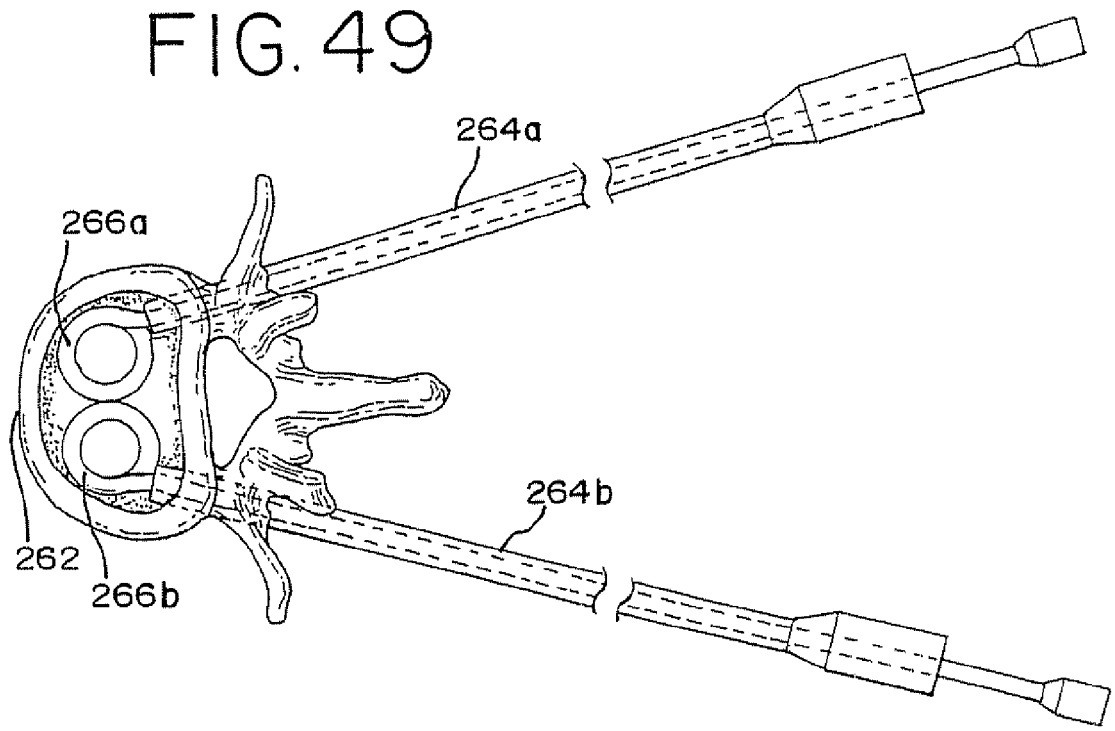

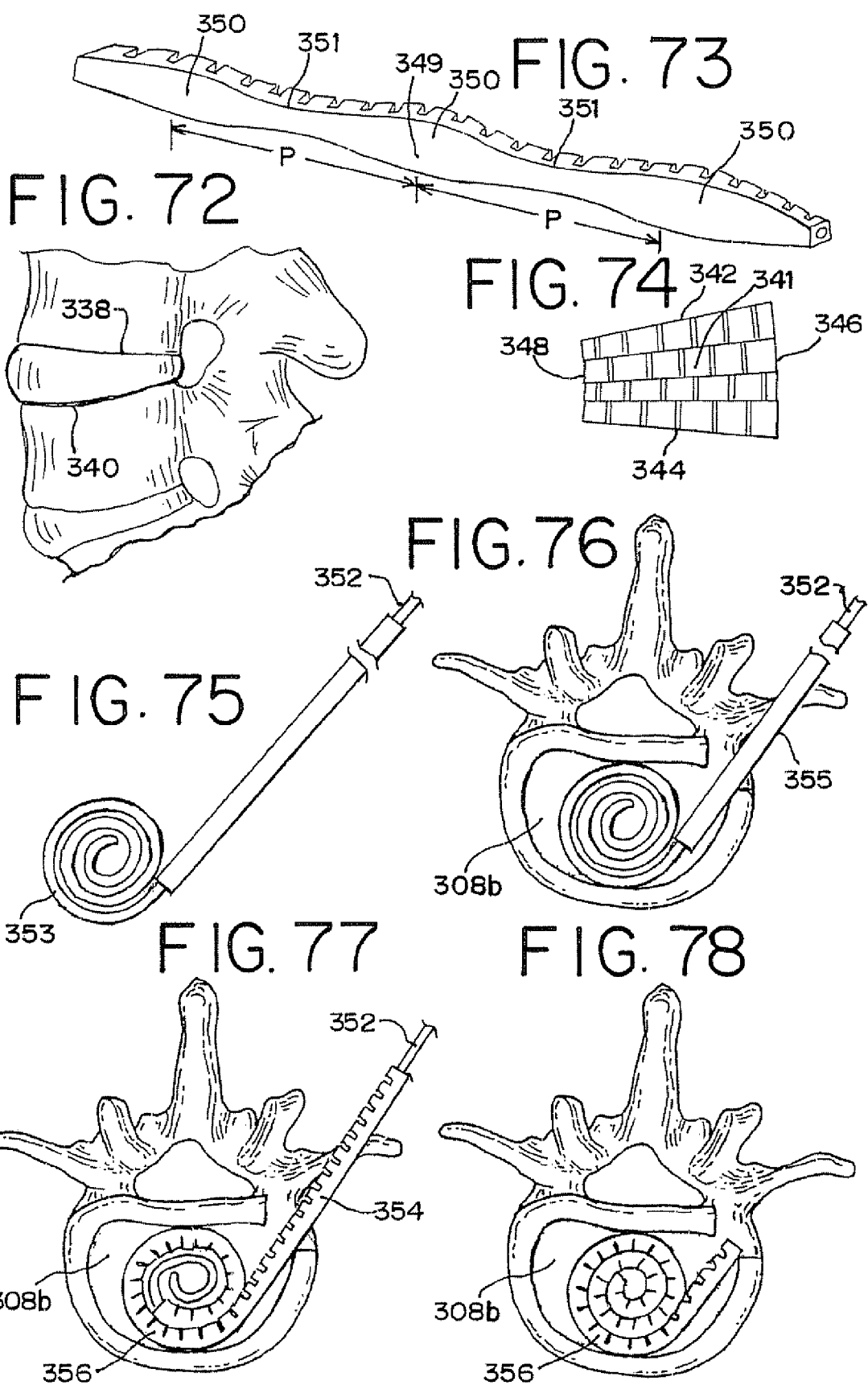

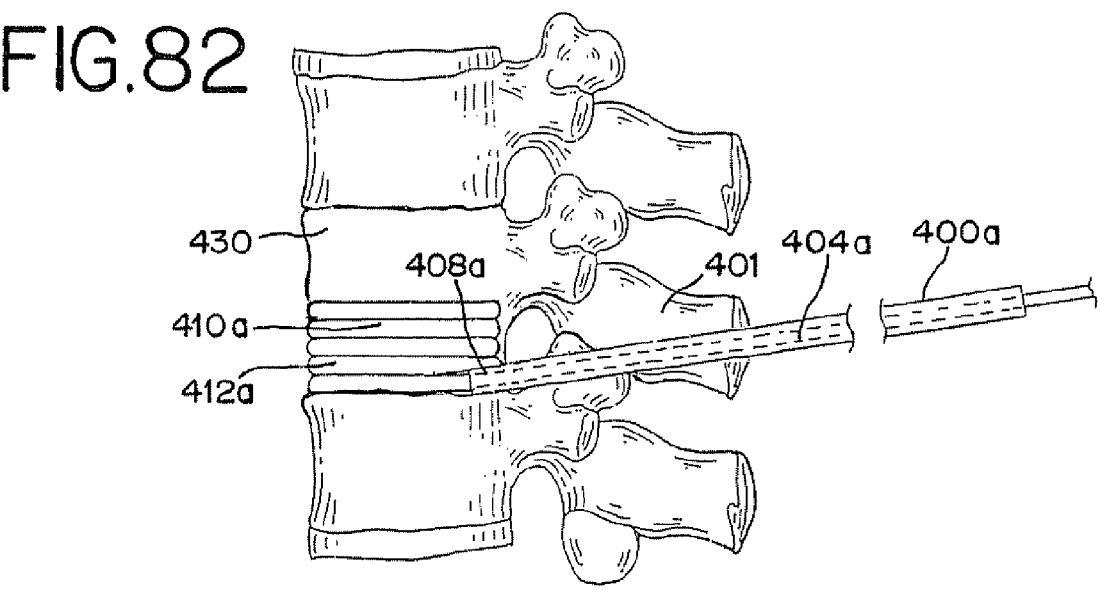
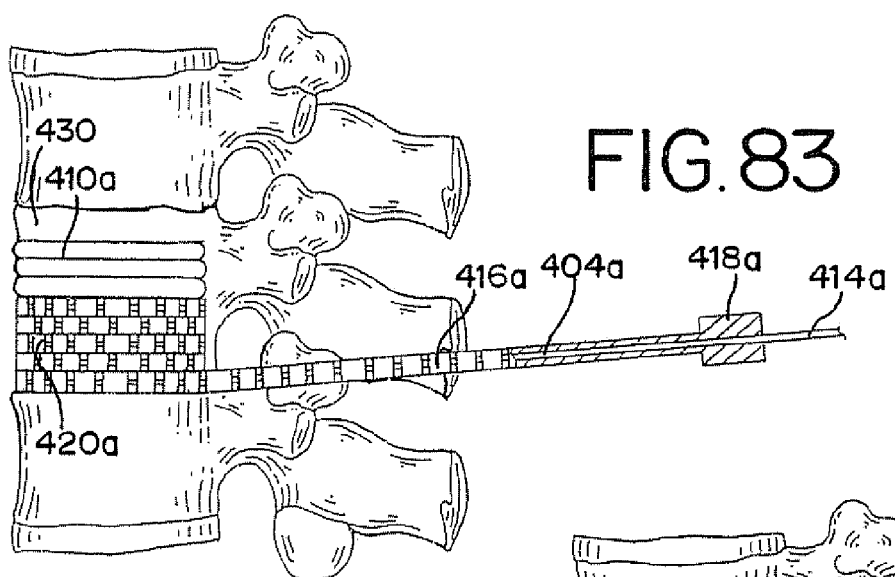
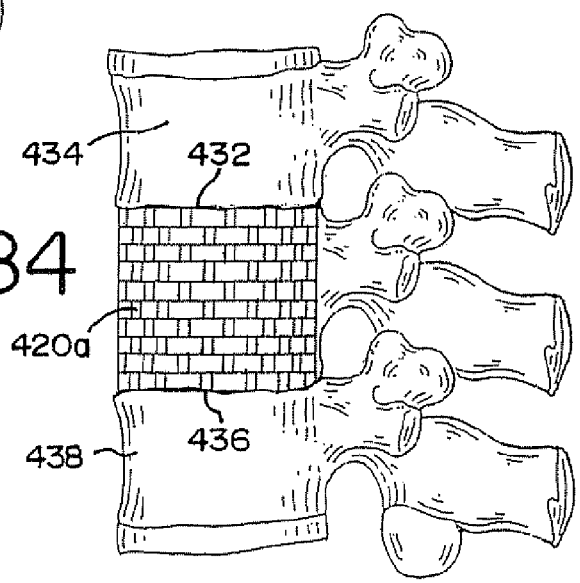

SPINAL TISSUE DISTRACTION DEVICES

This application claims the benefit of U.S. Provisional Application No. 60/708,691, filed Aug. 16, 2005; U.S. Provisional Application No. 60/738,432, filed Nov. 21, 2005; and U.S. Provisional Application No. 60/784,185, filed Mar. 21, 2006, all of which are hereby incorporated herein by reference.

FIELD OF THE INVENTION

The present invention generally relates to apparatus and methods employed in minimally invasive surgical procedures and more particularly to such apparatus and methods in orthopedic procedures for separating and/or supporting tissue layers.

BACKGROUND OF THE INVENTION

A variety of physical conditions involve two tissue surfaces that, for diagnosis or treatment of the condition, need to be separated or distracted from one another and then supported in a spaced-apart relationship. Such separation or distraction may be to gain exposure to selected tissue structures, to apply a therapeutic pressure to selected tissues, to return or reposition tissue structures to a more normal or original anatomic position and form, to deliver a drug or growth factor, to alter, influence or deter further growth of select tissues or to carry out other diagnostic or therapeutic procedures. Depending on the condition being treated, the tissue surfaces may be opposed or contiguous and may be bone, skin, soft tissue, or a combination thereof.

One such a condition that occurs in the orthopedic field is vertebral compression fractures. Vertebral compression fractures affect a significant part of the population, and add significant cost to the health care system. A vertebral compression fracture is a crushing or collapsing injury to one or more vertebrae. Vertebral fractures are generally but not exclusively associated with osteoporosis, metastasis, and/or trauma. Osteoporosis reduces bone density, thereby weakening bones and predisposing them to fracture. The osteoporosis-weakened vertebrae can collapse during normal activity and are also more vulnerable to injury from shock or other forces acting on the spine. In severe cases of osteoporosis, actions as simple as bending forward can be enough to cause a vertebral compression fracture. Vertebral compression fractures are the most common type of osteoporotic fractures according to the National Institute of Health.

The mechanism of such vertebral fractures is typically one of flexion with axial compression where even minor events can cause damage to the weakened bone. While the fractures may heal without intervention, the crushed bone may fail to heal adequately. Moreover, if the bones are allowed to heal on their own, the spine may be deformed to the extent the vertebrae were compressed by the fracture. Spinal deformity may lead to breathing and gastrointestinal complications, and adverse loading of adjacent vertebrae.

Vertebral fractures happen most frequently at the thoracolumbar junction, with a relatively normal distribution of fractures around this point. Vertebral fractures can permanently alter the shape and strength of the spine. Commonly, they cause loss of height and a humped back. This disorder (called kyphosis or "dowager's hump") is an exaggeration of the spinal curve that causes the shoulders to slump forward and the top of the back to look enlarged and humped. In severe cases, the body's center of mass is moved further away from the spine resulting in increased bending moment on the spine and increased loading of individual vertebrae.

Another contributing factor to vertebral fractures is metastatic disease. When cancer cells spread to the spine, the cancer may cause destruction of part of the vertebra, weakening and predisposing the bone to fracture.

Osteoporosis and metastatic disease are common root causes leading to vertebral fractures, but trauma to healthy vertebrae can also cause fractures ranging from minor to severe. Such trauma may result from a fall, a forceful jump, a car accident, or any event that compresses or otherwise stresses the spine past its breaking point. The resulting fractures typically are compression fractures or burst fractures.

Vertebral fractures can occur without pain. However, they often cause a severe "band-like" pain that radiates from the spine around both sides of the body. It is commonly believed that the source of acute pain in compression fractures is the result of instability at the fracture site, allowing motion that irritates nerves in and around the vertebrae.

Until recently, treatment of vertebral compression fractures has consisted of conservative measures including rest, analgesics, dietary, and medical regimens to restore bone density or prevent further bone loss, avoidance of injury, and bracing. Unfortunately, the typical patient is an elderly person. As a class of patients, the elderly generally do not tolerate extended bed rest well. As a result, minimally invasive surgical methods for treating vertebral compression fractures have recently been introduced and are gaining popularity.

One technique used to treat vertebral compression fractures is injection of bone filler into the fractured vertebral body. This procedure is commonly referred to as percutaneous vertebroplasty. Vertebroplasty involves injecting bone filler (for example, bone cement, allograph material or autograph material) into the collapsed vertebra to stabilize and strengthen the crushed bone.

In vertebroplasty, physicians typically use one of two surgical approaches to access thoracic and lumbar vertebral bodies: transpedicular or extrapedicular. The transpedicular approach involves the placement of a needle or wire through the pedicle into the vertebral body, and the physician may choose to use either a unilateral access or bilateral transpedicular approach. The extrapedicular technique involves an entry point through the posterolateral corner of the vertebral body.

Regardless of the surgical approach, the physician generally places a small diameter guide wire or needle along the path intended for the bone filler delivery needle. The guide wire is advanced into the vertebral body under fluoroscopic guidance to the delivery point within the vertebra. The access channel into the vertebra may be enlarged to accommodate the delivery tube. In some cases, the delivery tube is placed directly into the vertebral body and forms its own opening. In other cases, an access cannula is placed over the guide wire and advanced into the vertebral body. After placement, the cannula is replaced with the delivery tube, which is passed over the guide wire or pin. In both cases, a hollow needle or similar tube is placed through the delivery tube into the vertebral body and used to deliver the bone filler into the vertebra.

In this procedure, the use of lower viscosity bone filler and higher injection pressures tend to disperse the bone filler throughout the vertebral body. However, such procedures dramatically increase the risk of bone filler extravasation from the vertebral body. The transpedicular approach requires use of a relatively small needle (generally 11 gauge or smaller). In general, the small diameter needle required for a transpedicular approach necessitates injecting the bone filler in a more liquid (less viscous) state. Further, the pressure required to flow bone filler through a small gauge needle is relatively high. The difficulty of controlling or stopping bone filler flow into injury-sensitive areas increases as the required pressure increases. In contrast, the extrapedicular approach provides sufficient room to accommodate a larger needle (up to about 6 mm internal diameter in the lumbar region and lower thoracic regions). The larger needle used in the extrapedicular approach allows injection of bone filler in a thicker, more controllable viscous state. Therefore, many physicians now advocate the extrapedicular approach so that the bone filler may be delivered through a larger cannula under lower pressure. However, the transpedicular approach is still the preferred approach. Caution, however, must still be taken to prevent extravasation, with the greatest attention given to preventing posterior extravasation because it may cause spinal cord trauma. Physicians typically use repeated fluoroscopic imaging to monitor bone filler propagation and to avoid flow into areas of critical concern. If a foraminal leak results, the patient may require surgical decompression and/or suffer paralysis.

Another type of treatment for vertebral fractures is known as Kyphoplasty. Kyphoplasty is a modified vertebral fracture treatment that uses one or two balloons, similar to angioplasty balloons, to attempt to reduce the fracture and, perhaps, restore some vertebral height prior to injecting the bone filler. One or two balloons are typically introduced into the vertebra via bilateral transpedicular cannula. The balloons are inflated to reduce the fracture. After the balloon(s) are deflated and removed, leaving a relatively empty cavity, bone cement is injected into the vertebra. In theory, inflation of the balloons may restore some vertebral height. However, in practice it is difficult to consistently attain meaningful and predictable height restoration. The inconsistent results may be due, in part, to the manner in which the balloon expands in a compressible media, such as the cancellous tissue within the vertebrae, and the structural orientation of the trabecular bone within the vertebra, although there may be additional factors as well.

Thus there is a need for devices and methods to treat the above mentioned diseases, in particular compression vertebral fractures.

Another condition that can be treated by distraction or separation of tissue layers is disruption or degeneration of an intervertebral disk. An intervertebral disk is made up of strong connective tissue which holds one vertebra to the next and acts as a cushion between vertebras. The disk is divided into two distinct regions: the nucleus pulposus and the annulus fibrosus. The nucleus lies at the center of the disk and is surrounded and contained by the annulus. The annulus contains collagen fibers that form concentric lamellae that surround the nucleus. The collagen fibers insert into the endplates of the adjacent vertebral bodies to form a reinforced structure. Cartilaginous endplates are located at the interface between the disk and the adjacent vertebral bodies.

Proper disk height is necessary to ensure proper functionality of the intervertebral disk and spinal column. The disk serves several functions, although its primary function is to facilitate mobility of the spine. In addition, the disk provides for load bearing, load transfer and shock absorption between vertebral levels. The weight of the person generates a compressive load on the disks, but this load is not uniform during typical bending movements. During forward flexion, the posterior annular fibers are stretched while the anterior fibers are compressed. In addition, a translocation of the nucleus occurs as the center of gravity of the nucleus shifts away from the center and towards the extended side.

Changes in disk height can have both local and broader effects. On the local (or cellular) level, decreased disk height results in increased pressure in the nucleus, which can lead to a decrease in cell matrix synthesis and an increase in cell necrosis and apoptosis. In addition, increases in intra-diskal pressure create an unfavorable environment for fluid transfer into the disk, which can cause a further decrease in disk height.

Decreased disk height may also result in significant changes in the overall mechanical stability of the spine. With decreasing height of the disk, the facet joints bear increasing loads and may undergo hypertrophy and degeneration, and may even act as a source of pain over time. Increased stiffness of the spinal column and decreased range of motion resulting from loss of disk height can lead to further instability of the spine, as well as back pain. Radicular pain may result from a decrease in foraminal volume caused by decreased disk height. Specifically, as disk height decreases, the volume of the foraminal canal, through which the spinal nerve roots pass, decreases. This decrease may lead to spinal nerve impingement, with associated radiating pain and dysfunction.

Finally, adjacent segment loading increases as the disk height decreases at a given level. The disks that must bear additional loading are susceptible to accelerated degeneration and compromise, which may eventually propagate along the destabilized spinal column.

In spite of all of these detriments that accompany decreases in disk height, where the change in disk height is gradual many of the ill effects may be "tolerable" to the spine and may allow time for the spinal system to adapt to the gradual changes. However, a sudden decrease in disk volume caused by surgical removal of the disk or disk nucleus can heighten the local and global problems noted above.

The many causes of disruption or degeneration of the intervertebral disk can be generally categorized as mechanical, genetic and biochemical. Mechanical damage can include herniation in which a portion of the nucleus pulposus projects through a fissure or tear in the annulus fibrosus. Genetic and biochemical causes can result in changes in the extracellular matrix pattern of the disk and a decrease in biosynthesis of extracellular matrix components by the cells of the disk. Degeneration is a progressive process that usually begins with a decrease in the ability of the extracellular matrix in the central nucleus pulposus to bind water due to reduced proteoglycan content. With a loss of water content, the nucleus becomes desiccated resulting in a decrease in internal disk hydraulic pressure that ultimately results in a loss of disk height. This loss of disk height can cause non-tensile loading and buckling of the annulus. The loss of disk height also causes the annular lamellae to delaminate, resulting in annular fissures and rupture of the annulus. Herniation may then occur as rupture leads to protrusion of the nucleus.

Many disk defects are treated through a surgical procedure, such as a diskectomy in which the nucleus pulposus material is removed. During a total diskectomy, a substantial amount (and usually all) of the volume of the nucleus pulposus is removed and immediate loss of disk height and volume can result. Even with a partial diskectomy, loss of disk height can ensue.

Diskectomy alone is the most common spinal surgical treatment. The procedure is frequently used to treat radicular pain resulting from nerve impingement by a disk bulge or disk fragments contacting the spinal neural structures.

In another common spinal procedure, the diskectomy may be followed by an implant procedure in which a prosthesis is introduced into the cavity left in the disk space after the nucleus material is removed. Thus far, the most prominent prosthesis is a mechanical device or a "cage" that is sized to restore the proper disk height and is configured for fixation between adjacent vertebrae. These mechanical solutions take on a variety of forms including solid kidney-shaped implants, hollow blocks filled with bone growth material, and threaded cylindrical cages.

A challenge of inserting a disk implant posteriorly is that a device large enough to contact the endplates and slightly expand the intervertebral space between the endplates must be inserted through a limited space. This challenge is often further heightened by the presence of posterior osteophytes, which may cause converging or "fish mouthing" of the posterior endplates that results in very limited access to the disk. A further challenge in degenerative disk spaces is the tendency of the disk space to assume a lenticular shape, which requires a relatively larger implant that often is not easily introduced without causing trauma to the nerve roots. The size of rigid devices that may safely be introduced into the disk space is thereby limited.

Cages of the prior art have been generally successful in promoting fusion and approximating proper disk height. Cages inserted from the posterior approach, however, are limited in size by the interval between the nerve roots. Some examples of prior art devices are shown in U.S. Pat. No. 5,015,247 to Michelson, which describes an artificial threaded spinal fusion implant; U.S. patent application Ser. No. 10/999,727 to Foley et al., which describes vertebral spacer devices for repairing damaged vertebral disks; U.S. Pat. No. 4,309,777 to Patil, which describes a motion preserving implant that has spiked outer surfaces to resist dislocation and contains a series of springs to urge the vertebrae away from each other; and finally, U.S. patent application Ser. No. 10/968,425 to Enayati, which describes an expandable intervertebral prosthesis. All the above patents and patent applications are hereby incorporated herein by reference.

Therefore, a need remains for a device that can be inserted into an intervertebral disk space in a minimally invasive procedure and is large enough to contact and separate adjacent vertebral endplates. There also remains a need for a device that reduces potential trauma to the nerve roots and still allows restoration of disk space height.

Another related area in which tissue distraction may be required is spinal fusion. Fusion is a surgical technique in which one or more of the vertebrae of the spine are united together ("fused") so that motion no longer occurs between them. In spinal fusion surgery, bone grafts are placed around the spine, and the body then heals the grafts over several months—similar to healing a fracture—and joins or "fuses" the vertebrae together.

There are many potential reasons for a surgeon to consider fusing vertebrae, such as treatment of fractured (broken) vertebra, correction of deformity (spinal curves or slippages), elimination of pain from painful motion, treatment of instability, and treatment of some cervical disk herniations.

One of the more common reasons to conduct spinal fusion is to treat a vertebral fracture. Although not all spinal fractures need surgery, some fractures, particularly those associated with spinal cord or nerve injury, generally require fusion as part of the surgical treatment. Certain types of spinal deformity, such as scoliosis, also are commonly treated with spinal fusion. Scoliosis is an "S" shaped curvature of the spine that sometimes occurs in children and adolescents. Fusion can be used as a form of treatment for very large curves or for progressively worsening smaller curves. Additionally, fusion can be used to treat spondylolisthesis, which is a condition that occurs when hairline fractures allow vertebrae to slip forward on top of each other.

Another condition that is treated by fusion surgery is actual or potential instability. Instability refers to abnormal or excessive motion between two or more vertebrae. It is commonly believed that instability can either be a source of back or neck pain or cause potential irritation or damage to adjacent nerves. Although there is some disagreement on the precise definition of instability, many surgeons agree that definite instability of one or more segments of the spine can be treated by fusion.

Cervical disk herniations that require surgery usually need removal of the herniated disk (diskectomy) and fusion. With this procedure, the disk is removed through an incision in the front of the neck (anteriorly) and a small piece of bone is inserted in place of the disk. Although disk removal is commonly combined with fusion in the neck, this is not generally true in the low back (lumbar spine).

Spinal fusion is also sometimes considered in the treatment of a painful spinal condition without clear instability. A major obstacle to the successful treatment of spine pain by fusion is the difficulty in accurately identifying the source of a patient's pain. The theory is that pain can originate from painful spinal motion, and fusing the vertebrae together to eliminate the motion will eliminate the pain.

There are many surgical approaches and methods to fuse the spine, and they all involve placement of a bone graft between the vertebrae. The spine may be approached and the graft placed either from the back (posterior approach), from the front (anterior approach) or by a combination of both. In the neck, the anterior approach is more common and in the lumbar and thoracic regions a posterior approach is usually employed.

The ultimate goal of fusion is to obtain a solid union between two or more vertebrae. Fusion may or may not involve the use of supplemental hardware (instrumentation), such as plates, rods, screws and cages. Instrumentation can sometimes be used to correct a deformity, but it usually is just used as an internal splint to hold the vertebrae together while the bone grafts heal. Whether or not hardware is used, bone or bone substitutes are commonly used to get the vertebrae to fuse together. The bone may be taken either from another bone in the patient (autograft) or from a bone bank (allograft).

Yet another related area in which tissue distraction may be required is in the replacement of essentially an entire or a partially removed vertebra. Such removal is generally necessitated by extensive vertebral fractures, or tumors, and is not usually associated with the treatment of disk disease. Vertebral bodies may be compromised due to disease, defect, or injury. In certain cases, it becomes necessary to remove or replace one or more of the vertebral bodies or disks to alleviate pain or regain spinal functionality.

In the treatment of a removed vertebra, a device is used to form a temporary structural mechanical support that aids in replacing the removed vertebra with bone filler, such as calcium phosphate which promotes healing. A number of methods and devices have been disclosed in the prior art for replacing a diseased or damaged vertebral body. These prior art devices and the procedures associated therewith have difficulty in maintaining the proper structural scaffolding while a castable material, such as bone cement, is hardened in the cavity left by the removed vertebral body. The maintaining of proper structural scaffolding has been especially difficult in a minimally invasive posterior surgical approaches.

Spinal fusion or lumbar spinal fusion is one way to treat a compromised vertebral body due to unstable burst fractures, severe compression fractures, and tumor decompression. In a spinal fusion procedure, the disks above and below the compromised vertebral body are removed and a strut graft and plate are then used to make the vertebrae above and below the replaced vertebral body grow together and become one bone.

Some of the prior art vertebral body replacement systems include U.S. Pat. No. 6,086,613 to Camino et al., which describes an interbody fusion system made of a titanium mesh and endplates; U.S. Pat. No. 5,192,327 to Brantigan, which describes the use of singular or stackable modular implants; U.S. Pat. No. 6,585,770 to White et al., which describes a hollow body with an opening to receive bone growth inducing material; and U.S. Pat. No. 6,758,862 to Berry, which describes a vertebral replacement body device. All of the aforementioned references are hereby incorporated herein by reference.

Thus, there remains a need for improved devices for replacing one or more removed or partially removed vertebral bodies especially from a posterior approach and in a minimally invasive surgical intervention.

SUMMARY OF INVENTION

The present invention addresses many of the shortcomings in the prior devices and methods by providing a distraction device that separates or distracts tissue layers and maintains such separation.

A first aspect of the invention generally relates to distraction device systems for treating the human spine. The distraction device systems preferably comprise at least one guide member for guiding a generally elongated member to a location between the tissue layers of the spine. The guide member has a proximal end portion and a distal end portion. The distal end portion of the guide member is adapted to be inserted between tissue layers and defines a shape of a desired support structure. The elongated member is slidably mounted on the guide member for advancing the elongated member distally along the guide member to insert the elongated member between the tissue layers. The elongated member substantially conforms to the shape defined by the distal end portion of the guide member to form a support structure that separates, supports or both separates and supports the tissue layers.

Another aspect of the invention relates to distraction systems for treating the human spine. In one embodiment, the distraction system can include at least one guide member for guiding a distraction device to a location between the tissue layers of the spine. The guide member has a proximal end portion and a distal end portion. The distal end portion of the guide member is adapted to be inserted between tissue layers and defines a shape of a multi-tiered support structure. The distraction device is slidably mounted on the guide member for advancing the distraction device distally along the guide member to insert the distraction device between the tissue layers. The distraction device substantially conforms to the shape defined by the distal end portion of the guide member to form a multi-tiered support structure that separates, supports or both separates and supports the tissue layers.

Another aspect of the invention relates to intravertebral distraction systems for the treatment of vertebral defects and injuries, such as compression fracture. In one embodiment, the distraction system generally comprises at least one guide member for guiding a distraction device to a location within a vertebral body. The guide member has a proximal end portion and a distal end portion. The distal end portion of the guide member is adapted to be inserted into the vertebral body and defines a shape of a desired support structure. The distraction device is slidably mounted on the guide member for advancing the distraction device distally along the guide member for insertion into the vertebral body. The distraction device substantially conforms to the shape defined by the distal end portion of the guide member to form a support structure that separates, supports or both separates and supports the superior and inferior endplates.

Yet another aspect of the present invention relates to an intervertebral distraction system insertable between endplates of a superior vertebra and an inferior vertebra. In one embodiment, the distraction system comprises at least one guide member for guiding a distraction device to a location between a superior vertebra and an inferior vertebra. The guide member has a proximal end portion and a distal end portion. The distal end portion of the guide member is adapted to be inserted between the superior and inferior vertebrae and defines a shape of a multi-tiered support structure. The distraction device is slidably mounted on the guide member for advancing the distraction distally along the guide member for insertion between the superior and inferior vertebrae. The distraction device substantially conforms to the shape defined by the distal end portion of the guide member to form a multi-tiered support structure that separates, supports or both separates and supports the superior and inferior vertebrae.

These and other aspects of the present invention are set forth in the following detailed description. In that respect, it should be noted that the present invention includes a number of different aspects which may have utility alone and/or in combination with other aspects. Accordingly, the above summary is not exhaustive identification of each such aspect that is now or may hereafter be claimed, but represents an overview of the present invention to assist in understanding the more detailed description that follows. The scope of the invention is as set forth in the claims now or hereafter filed.

BRIEF DESCRIPTION OF THE FIGURES

In the course of this description, reference will be made to the accompanying drawings, wherein:

FIG. 5 is a perspective view of one embodiment of the distraction device of the present invention, shown in the form of a coil or a spring;

FIG. 6 is a vertical cross-sectional view of the distraction device of FIG. 5;

FIG. 7 is a perspective view of one embodiment of a delivery system of the present invention, showing a cannula, pusher and a pre-deployed distraction device;

FIG. 8 is a perspective view of the delivery system of FIG. 7 showing the distraction device partially ejected from the cannula;

FIGS. 9-11 are partial side views of the system of FIG. 7, illustrating a deployment sequence of the distraction device;

FIG. 12 is a top cross-sectional view of a vertebra and the deployment system of FIG. 7, showing the deployment of a distraction device within the vertebral body;

FIG. 13 is a side cross-sectional view of the vertebra and deployment system of FIG. 12, illustrating the partial deployment of the distraction device within a fractured vertebra;

FIG. 14 is a side cross-sectional view of the vertebra and deployment system of FIG. 12, with the distraction device essentially fully deployed to restore the height of the vertebral body;

FIG. 15 is a top cross-sectional view of a vertebra having a distraction device located within the vertebral body and bone filler (or "cement") being delivered within the vertebral body;

FIG. 31 is a perspective view of the vertebra shown in FIG. 30 with the guide wire partially deployed within the vertebral body;

FIG. 32 is a perspective view of the vertebra of FIG. 30 shown after the cannula and introducer sheath have been removed and a distraction device and pusher mounted on the guide wire;

FIG. 33 is a perspective view of the vertebra of FIG. 30 shown with the distraction device partially advanced or deployed within the vertebral body;

FIG. 34 is a perspective view of the vertebra of FIG. 30 shown with the distraction device substantially fully deployed within the vertebral body;

FIG. 35 is a side cross-sectional view of the vertebra of FIG. 30, with the distraction device fully deployed within the vertebral body;

FIG. 36 is a top cross-sectional view of a vertebra having a distraction device deployed within the vertebral body and bone filler being injected into the treatment site within the distraction device;

FIG. 37 is a top cross-sectional view of the vertebra shown in FIG. 36 having bone filler injected and contained within the inner space defined by the distraction device when in the deployed position defining a generally hollow cylindrical coil or helical shaped support structure within the vertebra;

FIG. 38 is a perspective view of the vertebra shown in FIG. 36 having bone filler substantially occupying the area within the distraction device;

FIG. 49 is a top partial cross-sectional view of a vertebral body with two delivery access opening being used in a transpendicular approach for side by side placement of distraction devices or guide wires;

FIG. 72 is a side view of a vertebral column with adjacent vertebrae having non-parallel endplates;

FIG. 73 is a perspective view of another embodiment of a distraction device of the present invention;

FIG. 74 is a side view of the distraction device of FIG. 73 when coiled to define a support structure;

FIG. 75 is a top view of a cannula delivering a guide wire in a spiral configuration;

FIG. 76 is a top cross-sectional view of an intervertebral disk with the guide wire deployed into the nucleus space;

FIG. 77 is a top cross-sectional view of the intervertebral disk of FIG. 76 with a distraction device placed over the guide wire and partially deployed within the vertebral body; and FIG. 78 is a top cross-sectional view of the intervertebral disk of FIG. 78 shown with the spiral shape distraction device deployed within the nucleus space;

FIG. 82 is a side view of a section of a vertebral column in which the vertebral body of one of the vertebra along with the adjacent disks have been substantially removed, and a guide wire is being deployed into the space created by such removal;

FIG. 83 is a side view of the vertebral column section of FIG. 82 shown with a distraction device mounted on the guide wire and partially deployed into the space created by the removal of the vertebral body and adjacent disks;

FIG. 84 is a side view of the vertebral column section of FIG. 82 shown with the distraction device fully deployed within the space created by the removal of the vertebral body and disks.

DETAILED DESCRIPTION

Figure 1:
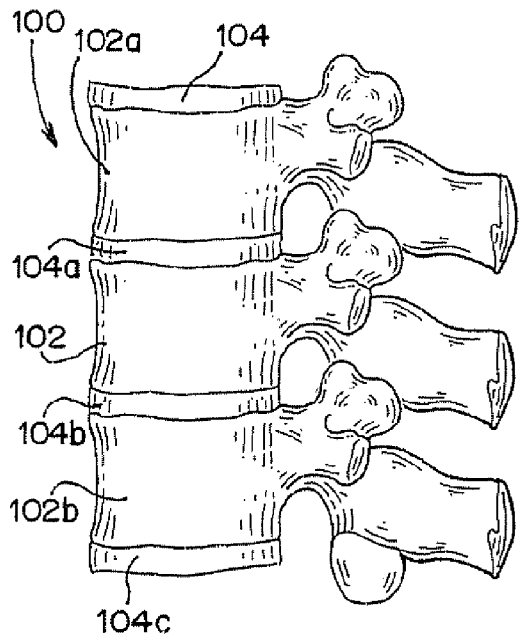
FIG. 1 is a partial side view of a normal human vertebral column.

FIG. 1 illustrates a section of a healthy vertebral (spinal) column, generally designated as 100, without injury. The vertebral column 100 includes adjacent vertebrae 102, 102a and 102b and intervertebral disks 104, 104a, 104b and 104c separating adjacent vertebrae.

Figure 3:
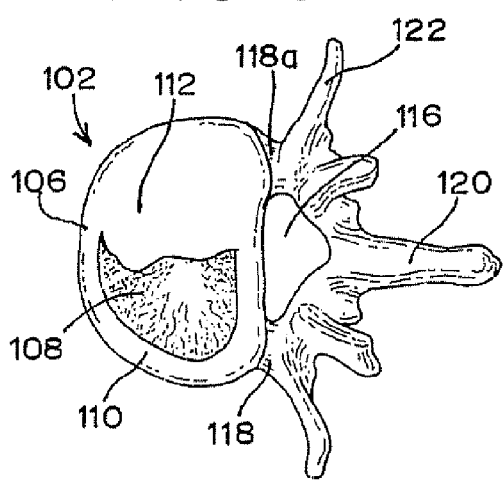
FIG. 3 is a top view of a vertebra with an endplate partially removed.
Figure 4:
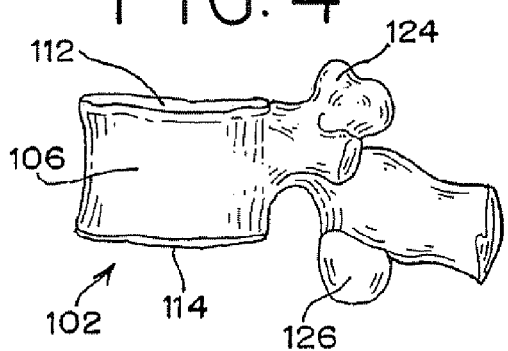
FIG. 4 is a side view of the vertebra of FIG. 3.

FIGS. 3 and 4 illustrate in more detail a normal vertebra and its attributes. The vertebra, generally designated as 102, includes a vertebral body 106 that is roughly cylindrically and comprised of inner cancellous bone 108 surrounded by the cortical rim 110, which is comprised of a thin layer of cortical compact bone. The cortical rim 110 can be weakened by osteoporosis and may be fractured due to excessive movement and/or loading. The body 106 of the vertebra is capped at the top by a superior endplate 112 and at the bottom by an inferior endplate 114, made of a cartilaginous layer. To the posterior (or rear) of the vertebral body 106 is the vertebral foramen 116, which contains the spinal cord (not shown). On either side of the vertebral foramen 116 are the pedicles 118, 118a, which lead to the spinal process 120. Other elements of the vertebra include the transverse process 122, the superior articular process 124 and the inferior articular process 126.

Figure 2:
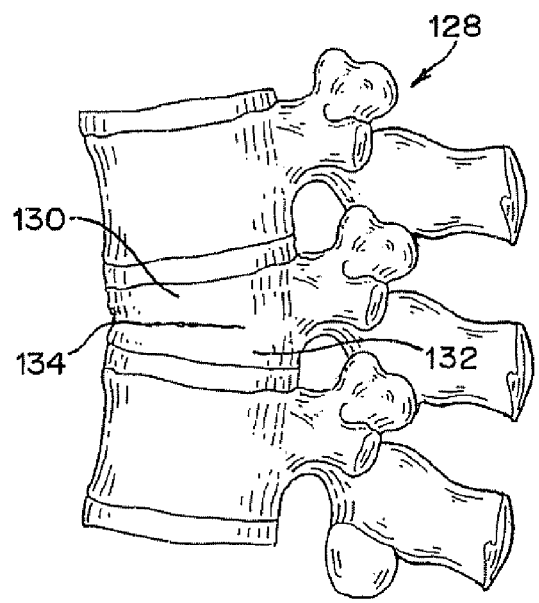
FIG. 2 is comparable to FIG. 1, but shows a vertebral compression fracture in one of the vertebral bodies.

FIG. 2 illustrates a damaged vertebral column, generally designated as 128, with a vertebral body 130 of a vertebra 132 suffering from a compression fracture 134. The vertebral body 130 suffering from the compression fraction 134 becomes typically wedge shaped and reduces the height of both the vertebra 132 and vertebral column 128 on the anterior (or front) side. As a result, this reduction of height can affect the normal curvature of the vertebral column 128. It is understood that pain caused by a compressed vertebral fracture 134 can sometimes be relieved by procedures like vertebroplasty and kyphoplasty, (these procedures have been described in the background), however such procedures have safety concerns and sometimes fails to provide a desired or predictable height restoration.

Turning now to a detailed description of illustrated embodiments of the present invention. The apparatus or device of the present invention, which is generally defined as a distraction device, can serve to actively separate tissue layers by engaging them and forcing them apart, or to support the separation of tissue layers separated by the distraction device itself or by other devices or processes or a combination of these. Accordingly, the term "distracting device" is intended to have a general meaning and is not limited to devices that only actively separate tissue layers, only support tissue layers or only both actively separate and support tissue layers. For example, the distraction device in general can be used to actively separate layers of tissue and then be removed after such separation, or the distraction device could be used to support layers of tissue that have been previously separated by a different device. Alternatively, the distraction device can be used to actively separate the layers of tissue and remain in place to support the layers of tissue in order to maintain such separation. Unless more specifically set forth in the claims, as used herein, "distraction device" encompasses any and all of these.

It should also be understood that various embodiments of the device, system and method of the present invention are illustrated for purposes of explanation in the treatment of vertebral compression fractures, height restoration of a diseased disk, vertebral fusion procedures and/or replacement of removed disks or vertebra. However, in its broader aspects, the present invention is not limited to these particular applications and may be used in connection with other tissue layers, such as soft tissue layers, although it has particular utility and benefit in treatment of vertebral conditions.

FIG. 5 illustrates one embodiment of a distraction device, generally designated as 136, in accordance with the present invention. In this embodiment, the distraction device 136 is preferably comprised of an elongated member, such as thread or ribbon, made of a shape memory material, such as a Nitinol (NiTi) or other suitable alloy (Cu—Al—Ni, Ti—Nb—Al, Au—Cd, etc.), a shape memory polymer or other suitable materials. In this illustrated embodiment, the distraction device thread or ribbon has a rectangular cross-section. However, as described in more detail below, the distraction device can have a variety of shapes and profiles.

When deployed between tissue layers, as shown in FIGS. 5, 14, 16-26, 29, 35, 39-48, 50-54, 65, 71, 74, 72, 81 and 84, for example, the distraction device 136 defines a support structure of a predetermined configuration such as a multi-tiered arrangement, scaffolding or platform that serves to actively separate or support (or both) opposed tissue layers. In FIG. 5, the distraction device, as deployed, has a helical, coil or spring-like configuration. As illustrated, the distraction device defines a helical configuration with a tight pitch forming an essentially hollow cylinder or cage. As shown, each turn or winding 140 is wound on top of the previous winding 140a to form a plurality of stacked windings or tiers with little or no spacing between each winding or tier. In this configuration, the distraction device 136 forms a very stiff column or support structure 141 along the axis of a center line of the coil or spring as shown in FIG. 6.

Preferably, the support structure 141 includes or defines an innerspace or resident volume 145. As used herein, "resident volume" refers generally to a structural characteristic of the support structure. The resident volume is a volume that is generally defined by the distraction device, when it is in the deployed configuration. The resident volume is not necessarily a volume completely enclosed by the distraction device and can be any volume generally defined by the distraction device. This term does not necessarily mean that the resident volume is an open or void volume or cavity and does not preclude a situation in which the resident volume is, at some point in time, filled with another material, such as bone filler, cement, therapeutic drugs or the like. It also does not preclude the resident volume from containing undisturbed human tissue that is located or remains within the resident volume during or after deployment of the distraction device, as will be explained in more detail below. For example, if the distraction device is employed to separate adjoining soft tissue layers, such as subcutaneous fat and underlying muscle tissue, the resident volume of the distraction device may be hollow or void of tissue after separation. On the other hand, if inserted into a vertebra having cancellous bone tissue therein, the resident volume will contain undisturbed bone tissue and no void or cavity is formed by the distraction device.

In order to shape the distraction device 136 like a coil or spring, it is helpful to understand the characteristics of a shape memory alloy. Nickel-Titanium alloys, such as Nitinol, exhibit the phenomena of thermal shape memory and superelasticity. The term thermal shape memory refers to the material's ability to return from a plastically deformed shape to a pre-determined shape upon increasing the temperature of the material. The term superelasticity refers to the elastic ability of the material. Materials with superelastic characteristics can be deformed by applying a force to constrain the material in a deformed or constrained shape. Once the force or constraint is removed, the material will substantially return to its pre-determined or initial shape. Superelastic materials, such as Nickel-titanium alloys, can be considerably more elastic than stainless steel. The pre-determined or initial shape can be referred to as the free state and the deformed shape can be referred to as the constrained state.

The initial or pre-determined shape of a shape memory material is normally set by a heat treatment process, which is well known in the art. In the present invention, the material selected is wound on a mandrel and securely attached so it can be heat treated to set the desire shape, in this case, to be configured like a tight pitch coil or helical shape. The heat cycle is typically around 500° C. and for a period of 10 minutes to 60 minutes depending on the strength of the material, spring constant and oxide layer required. The mandrel could range in sizes from about 0.125 to about 2.0 inches, but is preferably around 0.5 inches in diameter. The wind direction could be right hand or left hand, with a tight pitch, having little or no space between adjacent coils or turns. However, other pitches could be used if required by the application, and if the material is of sufficient strength, the coils can be spaced apart.

Because of the shape memory characteristics of the material used in the construction of the distraction device 136, the distraction device can be deformed prior to or during delivery to a desired treatment site, and then returned to its original shape within the treatment site. In other words, the distraction device has an inherent tendency or is predisposed to form itself into its deployed shape. Referring to FIGS. 5-8, for example, the distraction device 136 is first formed into the helical or coil shape seen in FIG. 5. It may then be unwound or deformed into a substantially linear configuration or pre-deployed configuration (see FIG. 7) by insertion into a cannula 142 for delivery. The cannula 142 constrains the distraction device 136 (shown in phantom within the cannula) in the deformed (straight) shape as the distraction device is passed through the cannula. While constrained within the cannula, the deformed shape or pre-deployed shape of the elongated member is substantially linear in that the shape can be perfectly straight or the shape could include slight bends or zigzags. Upon exiting an opening 144 in a distal end portion 146 of the cannula 142, the distraction device 136, by change of configuration, returns to its initial or free state, as illustrated in FIG. 8. As shown, a coiled portion of the distraction device 136 is outside of the cannula 142 in the free state and the remaining portion of the distraction device is inside the cannula in a constrained state. When the distraction device 136 exits the cannula 142 and reforms into a coil shape it defines or provides a support structure 141 that includes a resident volume 145. The support structure 141 may be used in a vertebra to actively separate endplates and restore height, or the support structure may be used to support endplates that have been previously separated by a different device.

The cannula 142 preferably has a lumen 143 and a bore 144 that is complementary to or the same as the cross-section of the distraction device 136. The distraction device 136 can be pushed or pulled through the cannula 142 with the aid of a pushrod 150 or other suitable advancement device. The proximal end 152 of the cannula 142 may have a knob or handle 154 or other structure for ease of use and a proximal end 156 of the pushrod 150 also may have a knob or handle 158 as well.

FIGS. 9, 10 and 11 depict the action of the distraction device 136 as it reforms into its initial or deployed configuration upon being advanced out of the distal end 146 of the cannula 142. As previously explained, the distraction device 136, i.e., the elongated member or ribbon, is inserted or loaded into the cannula 142 where it may be deformed into a constrained state, e.g., a substantially straight or linear state. The pushrod 150 (not shown) or other suitable advancement mechanism is manipulated to advance the distraction device out of the distal end 146 of the cannula 142. As the distraction device 136 exits out the distal end portion 146 of the cannula 142 in the direction of the arrow A, the device begins to return to its wound or coil shape because it is no longer being constrained by the cannula. In the illustrated embodiment, the distraction device 136 returns to the initial configuration as it winds in a clockwise direction as indicated by arrow B.

As shown in FIG. 10, the distraction device 136 continues to advance out of the distal end 146 of the cannula 142, in the direction of arrow A and continues to wind in the direction of arrow B. As the number of windings 140 increase, the height or extent of the coiled shaped support structure 141 also increases as represented by arrow C. Preferably, in use, the extent or height of the support structure will increase in the direction of tissue separation. The process will continue until the desired height or extent of the support structure 141 is obtained and/or the distraction device 136 is fully displaced from the cannula. When the distraction device is completely pushed out of the cannula 142, as illustrated in FIG. 11, the coil shaped support structure 141 is at its full deployed height, which preferably is the distance required for height restoration of a compressed vertebra or a diseased disk when the device is used for such treatments.

In a typical procedure for treatment of a vertebral compression fracture, access to the vertebra can be gained by using the same procedures and techniques that are used for the other vertebral procedures mentioned above, or by any other procedures and techniques generally known by those skilled in the art. Referring to FIGS. 12 and 13, which illustrate one potential procedure, an access opening 160 is drilled into the cortical rim 110 of the vertebral body 130 of a vertebra 132 suffering from a compression fracture 134. The cannula 142 is inserted through the access hole 160 into the vertebral body 130. Alternatively, the cannula 142 may be placed adjacent to the access hole 160 instead of inserted through the access hole. Typically, the access opening 160 will be drilled through the pedicle 118, which is sometimes referred to as a transpedicular approach. However, the access hole 160 could be made in any other portion of the cortical rim 110 as the physician may chose.

The distraction device 136 may be prepositioned within the cannula 142, which constrains the distraction device in the deformed or pre-deployed configuration. As the pushrod 150 is advanced, the distraction device 136 is advanced out of the distal end portion 146 of the cannula 142 and into the cancellous bone 108 of the vertebral body 130. Upon exiting the cannula 142, the distraction device 136 will begin to revert, by change of configuration, to its initial or deployed coil shape to define support structure 141. Thus, as it is advanced from the cannula, the distraction device 136 winds up into the relatively spongy cancellous bone 108 of the vertebral body 130 as shown in FIG. 13. Preferably, as the distraction device traverses or passes through the cancellous bone 108 there is no compression of cancellous bone. Additionally, in a preferred embodiment, the distraction device does not create a significant void or cavity within the cancellous bone, but instead winds through the cancellous bone so that undisturbed cancellous bone 108a is located within the resident volume 145 defined by the support structure 141.

As deployment of the distraction device 136 progresses into the cancellous bone 108 between the endplates 112, 114, in this embodiment, the spring-shaped distraction device support structure 141 will contact the endplates and start to distract the endplates (or actively separate them) apart from each other as the support structure increases in height. The distraction device 136 will be advanced out of the cannula 142 until the distraction device attains the desired height or extent as measured in the direction of endplate separation, or the endplates 112, 114 have been separated by a desired distance. Typically, the distraction device 136 is advanced until the height of the distraction device support structure 141 is such that it returns the endplates 112, 114 to a normal pre-compression position, or such other spacing as the physician deems appropriate as illustrated in FIG. 14, therefore alleviating a potential deformity that could eventually result in kyphosis. It is understood that the action accomplished by the distraction device preferably restores all or a substantial portion of the original height of the vertebra, although there may be circumstances where partial height restoration is deemed sufficient.

In one embodiment of the present invention, the height of the vertebra is estimated prior to the procedure by measuring adjacent vertebrae, and then an appropriate sized distraction device that will achieve the desired height upon completely exiting the cannula is selected. Alternatively, the height of the distraction device could be monitored during the procedure, and when the desired height is attained, the distraction device ("ribbon") could be severed at a location near the distal end of the cannula.

Another optional and beneficial aspect of the distraction device of the present invention is the ability to control the delivery of flowable material, such as bone filler, for example bone cement, allograph, autograph or some other biocompatible material, or therapeutic drug into the treatment site. One example of an appropriate bone filler is polymethyl methacrylate (PMMA), commercially available as Kyphx HV-R from Kyphon, Spineplex from Stryker, Simplex from Stryker Howmedica and Parallax Acrylic Resin with Tracers TA from Arthocare. The distraction device also can be used to control the delivery of drugs or other agents or fluids, depending on the application.

Figure 15A:
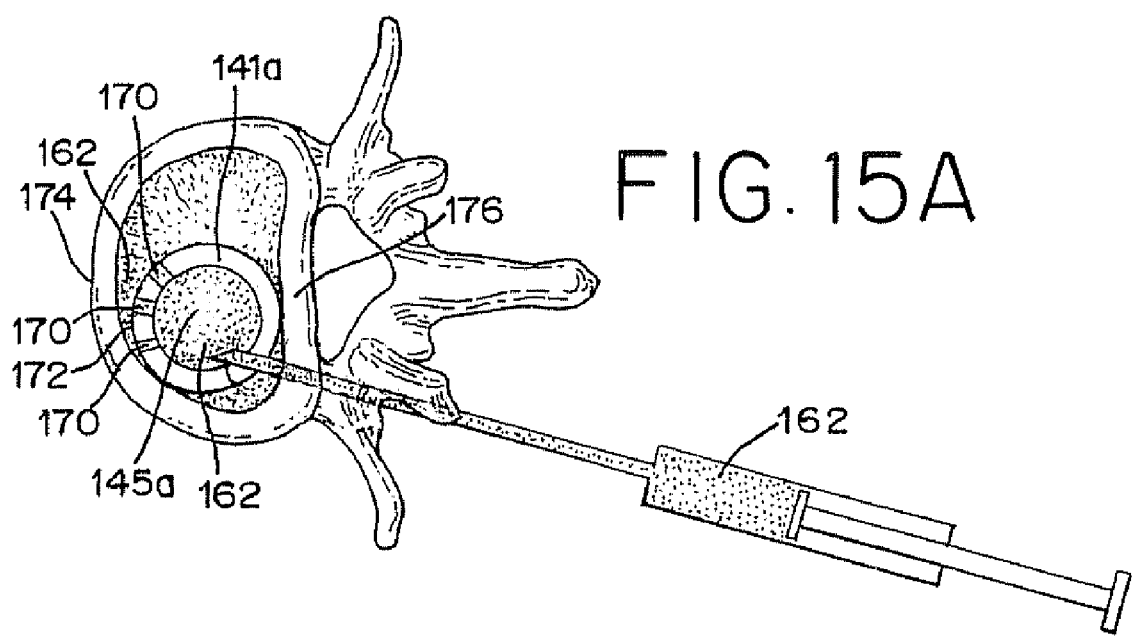
FIG. 15A is a top cross-sectional view of a vertebra having a distraction device located within the vertebra body, the distraction device having channels or grooves to direct the flow of injected bone filler.

For example, once the support structure 141 defined by the distraction device is in place, bone filler 162 can be introduced into the treatment site to assist in stabilization of the distraction device and to aid in supporting the separation of the endplates 112, 114. As illustrated in FIG. 15, a syringe 164 can be used to deliver the bone filler 162 into the treatment site. The tip 166 of the syringe 164 can be inserted between the windings 140, 140a (shown in FIG. 14) of the coil shaped distraction device 136 to access the resident volume 145 (which may or may not contain undisturbed cancellous bone, depending on the desired application) defined by the support structure 141. When the resident volume 145 is filled with cancellous bone, introduction of bone filler into the resident volume creates a cancellous bone/bone filler amalgam, similar to prior vertebroplasty procedures, and the support structure 141, in effect, acts like a container or barrier that contains the bone filler 162 within a specified location and prevents or reduces the potential for bone filler contact with more sensitive tissue such as nerve fibers. In alternative embodiments, the support structure may also serve to limit and direct the flow of the bone filler into areas outside the distraction device, as illustrated in FIG. 15A and explained in more detail below. The container effect greatly reduces the complications associated with injection of bone filler because the container-like effect of the distraction device greatly reduces the chances of extravasation.

The distraction device can have a variety of the cross-sectional profiles configurations, as shown in FIGS. 16-26. However, it will be understood that other designs or profiles could be used based on the appropriate type of treatment required without departing for the present invention. Turning now to the illustrated configurations, the cross-sectional profile of the elongated member or ribbon of the distraction device 136 may be of a variety of shapes, depending on the application and desired attributes. In certain applications, the profile may be more significant to functionality than in other applications.

Figure 16:
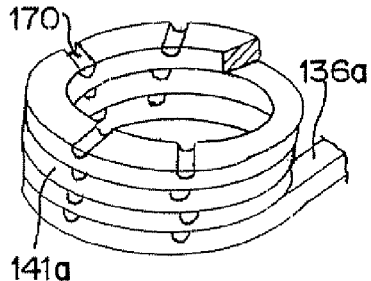
FIGS. 16-26 are perspective views of different embodiments of distraction devices with different cross-sectional profiles.

In FIG. 16, the cross-sectional shape of the distraction device is generally rectangular. When the distraction device is made from a shape memory material using the process described above, the winding surface on the mandrel is preferably the short axis for better stability and increased surface contact when inserted into a vertebra. In other words, the distraction device is formed so that the wider side contacts the tissue to be distracted (e.g., endplates of a vertebra) to provide reduced contact pressure. However, the distraction device could also be wound on the long axis depending on the application. The range of the material profile could be from about 0.005×0.010 inches (about 0.127 mm×0.254 mm) (height× width) to about 0.10×0.50 inches (about 2.54 mm×12.7 mm), but preferably in the range of 0.01×0.02 inches (about 12.7 mm×0.5 mm) to 0.05×0.25 inches (about 1.27 mm×6.35 mm).

If desired, the distraction device 136a can include lateral grooves or slots 170 or other lateral passageways at strategic locations. These grooves 170 or other passageways may be formed by drilling, cutting, grinding or compressing the distraction device material. When the distraction device is made of a shape memory material, the grooves or passageways can be formed either before or after winding and heat treating. The grooves 170 can be uniformly or randomly spaced apart and, depending on the desired treatment, located only on one side of the support structure defined by the distraction device. The grooves 170 can be used to direct and limit the flow of bone filler injected into and around the treatment site. For example, as illustrated in FIG. 15A, the grooves 170 can be located on the distraction device so that they are on only the anterior side 172 of the support structure. When the grooves 170 are arranged as such, the grooves control the direction of the bone filler 162 so that the bone filler injected into the center area 145a defined by the support structure 141a is directed to flow toward the anterior portion 174 of the vertebral body and away from the posterior portion 176 where the bone filler 162 could penetrate the blood venous return system, which could create embolism complications or cause spinal cord trauma.

Figure 17:
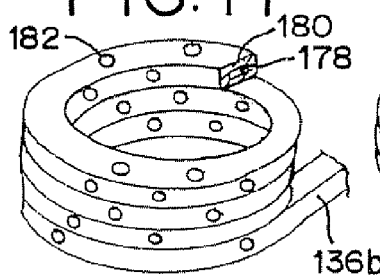

In FIG. 17, the cross-sectional shape of the distraction device 136b is that of a generally rectangular tube having a channel 178 extending therethrough. This profile configuration may be similar to the rectangular outer dimensions detailed in the previous embodiment and may have a wall 180 within the range of about 0.002 to 0.25 inches (about 0.05 mm to 6.35 mm), but more preferably in the range of about 0.005 to 0.020 inches (about 0.127 mm to 6.35 mm).

The distraction device could also include apertures or holes 182 which extend through the wall 180 and communicate with the internal bore or channel 178. The apertures 182 can be uniformly or randomly spaced apart and may be of the same size or vary in size. Additionally, the apertures 182 could be limited to the inner wall of the distraction device or to the outer wall of the distraction device or could be located on both the inner and outer walls. Further, the apertures 182 could be limited to one side of the distraction device, such as on the anterior side or posterior side. Bone filler can be delivered to the treatment site by inserting the tip of the syringe into the channel 178 and injecting the bone filler into the channel. The bone filler will flow along the channel 178 and escape out of the apertures 182 in the desired directions into the treatment site. The location and arrangement of the apertures will determine the direction of bone filler injected within the treatment site.

The distraction device also may be coated with a polymer based of bone filler material that can be activated upon implantation and diffused into the surrounding tissue. This potential feature is applicable to a distraction device of any cross-sectional shape.

Figure 18:
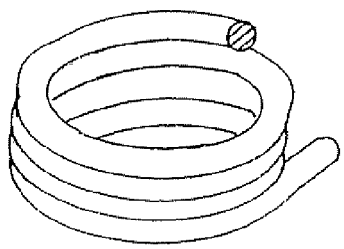

In FIG. 18, the cross-sectional shape is round. This profile may be slightly less stable during certain treatments because, in some cases, the windings could have the tendency to slip over each other. However introduction of bone filler material into the center of the windings may, after curing add substantially to the stability of this distraction device as well as the others shown in FIGS. 16-26. The diameter of the circular cross-sectional distraction device in FIG. 18 preferably ranges from about 0.005 to 0.025 inches (about 0.127 mm to 0.635 mm).

Figure 19:
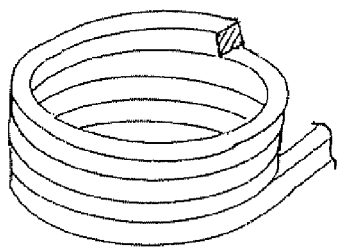

In FIG. 19, the cross-sectional shape is square. This profile has similar advantages as the rectangular profile and would be much stiffer at the same width dimension as the rectangular one.

Figure 20:
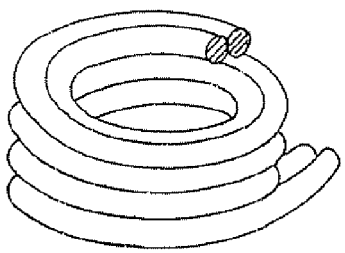

In FIG. 20, the cross-sectional shape is double round. This profile has improved stability over a single round profile while being easy to wind. The double round profile could be extruded as such or welded together or otherwise joined prior to winding and heat treatment. The size of each round section is preferably in the same range as the round profile.

Figure 21:
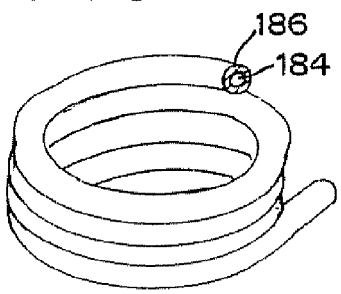

In FIG. 21, the cross-sectional shape is that of a round tube that includes a channel or bore 184 that forms a lumen through the distraction device. This profile may have similar dimensions as the round profile, and may have a wall 186 with a thickness in the range of about 0.002 to 0.05 inches (about 0.05 mm to 1.27 mm). This embodiment of the distraction device may also include apertures, generally similar to the apertures 182 described above with respect to FIG. 17, for flow of bone filler or other material into the treatment site.

Figure 22:
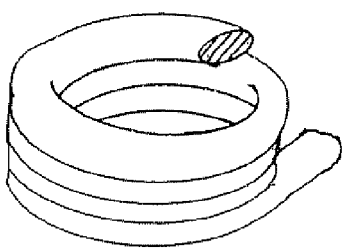

In FIG. 22, the cross-sectional shape is oblong. This profile can be obtained by taking a distraction device that has the same dimensions as the round profile and flattening it, preferably prior to heat treatment if the device is made of a shape memory material. The flattening process could use roller technology where the material is pushed between rollers that are separated by a distance less than the diameter of the distraction device. Several passes might be necessary depending on the thickness required. One of the advantages is potentially an increase in stability over a round profile without having any sharp corners or edges that are commonly associated with interfering surfaces.

Figure 23:
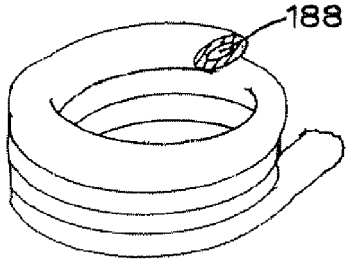

In FIG. 23, the cross-sectional shape is that of an oblong tube. This profile is generally similar to the oblong profile, but includes a center channel or bore 188 defining a lumen through the distraction device. Additionally, this embodiment could also include the apertures generally similar to those described above with respect to FIG. 17.

Figure 24:
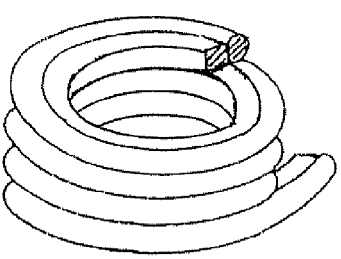

In FIG. 24, the cross-sectional shape is a combination of the above shapes. This profile combines two or more of the previously described profiles. For instance, the device could have a square and a round profile, as shown. It is understood that any combination of profiles can be achieved using one or more profiles as might be required by the application.

Figure 25:
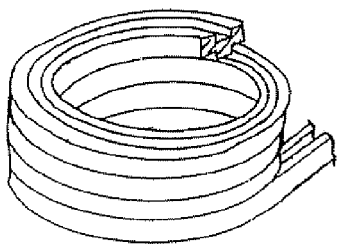

In FIG. 25, the cross-sectional shape is a custom profile. This type of profile may require special manufacturing process like special extrusion dies or secondary manufacturing after extrusion to create the desired profile. The advantage of such profile would be the locking characteristic of the windings on top of each other to form a very solid column not only in the vertical direction but also resistant to sliding or shifting in the lateral direction as well.

Figure 26:
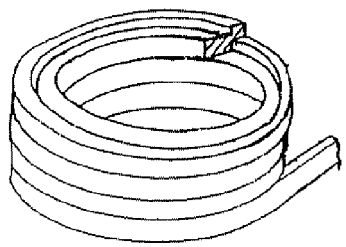

In FIG. 26, the cross-sectional shape is another custom profile having benefits as described above with reference to FIG. 25.

The distraction devices of the present invention may also be used in intervertebral disk treatments and intervertebral body fusion procedures, as well as, total or partial vertebral body replacements procedures. One of the advantages of the present invention is the ability to use the device in a minimally invasive surgery setting that allows the surgeon to use an endoscopic approach to remove damaged spinal tissue due to disease, such as trauma or tumor and to deploy the device into the space created by such removal.

Figure 26A:
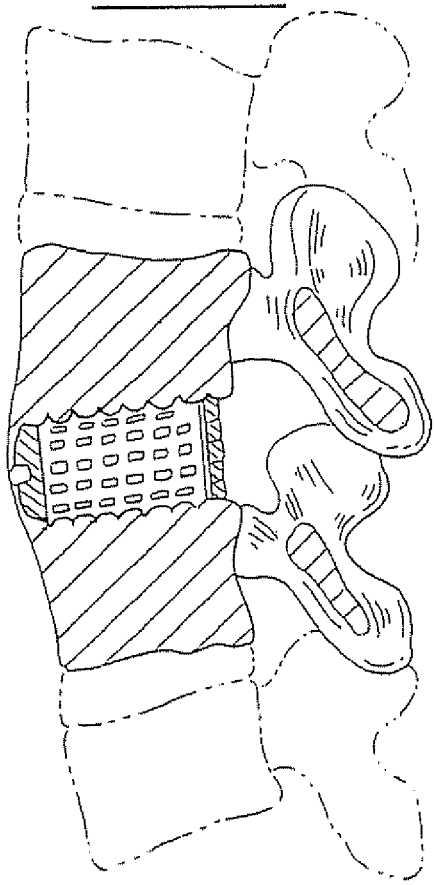
FIG. 26A is an illustration of a prior art device in which a "cage" is inserted between adjacent vertebrae.

FIG. 26A illustrates a prior art device, sometimes referred to as a "cage," that is used in intervertebral disk treatments and intervertebral body fusion procedures. These cage type devices typically have a fixed size that does not substantially change before, during or after implantation. Thus, in order to implant "cage" type devices, a relatively large incision is made in the patient's back and spinal tissue to accommodate the size of the device being inserted. Additionally, the use of a separate tool may be required to separate or distract the spinal tissue prior to insertion of the device between the tissue.

Figure 26B:
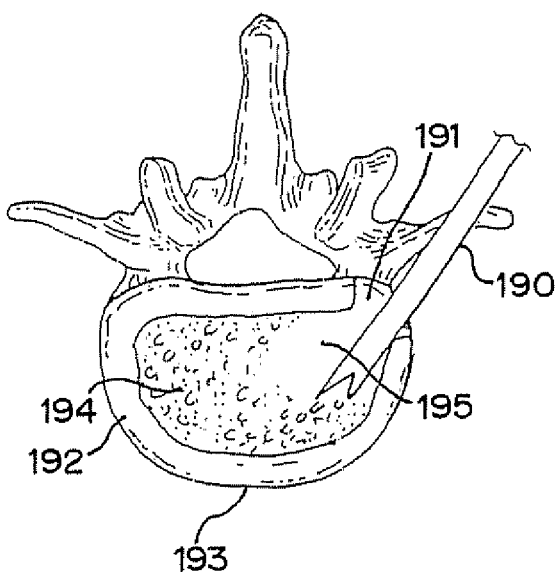
FIG. 26B is a top cross-sectional view of an intervertebral disk shown with a disk removal tool inserted into the disk for disk nucleus pulpous removal.

In one minimally invasive method of an intervertebral disk treatment or intervertebral body fusion procedure in accordance with the present invention, a disk nucleus removal tool 190, such as rongeurs, curettes, probes or dissectors, is inserted through a small access hole 191 in the annulus fibrous 192 of an intervertebral disk 193, as illustrated in FIG. 26B. The removal tool 190 is used to remove a portion of or the entire disk nucleus pulpous 194 by endoscopic techniques and procedures generally known to those skilled in the art.

Figure 26C:
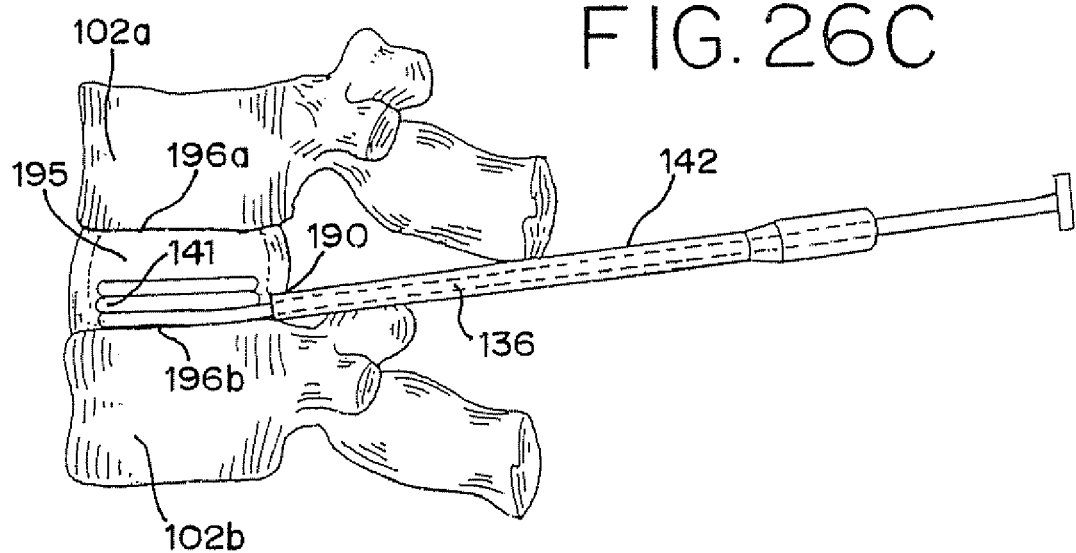
FIG. 26C is a side partial cross-sectional view of the intervertebral disk of FIG. 26B shown between superior and inferior vertebrae and with a distraction device being delivered into the intervertebral disk via a cannula.
Figure 26D:
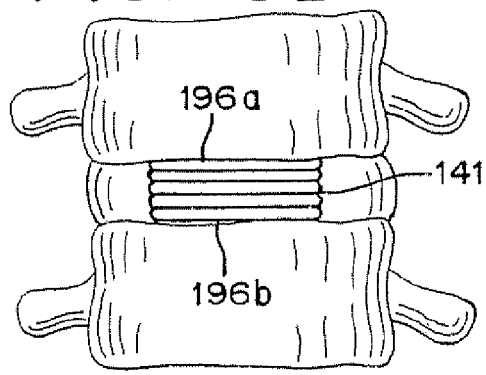
FIG. 26D is a partial cross-sectional anterior view of the intervertebral disk of FIG. 26B shown between superior and inferior vertebrae and with the distraction device completely deployed within the disk.

Referring to FIG. 26C, a delivery cannula 142 is inserted through the access hole 190 and a distraction device 136 is deployed into the space 195 created by the removal of the nucleus pulpous 194. As described above, the distraction device 136 preferably has a substantially linear pre-deployed configuration for deployment through the cannula 142 and a coiled or deployed configuration upon exiting the cannula in which the distraction device defines a support structure 141. As the distraction device 136 exits the cannula, the support structure 141 increases in extent heightwise within the space 195. As deployment of the distraction device 136 progresses, the support structure 141 will cause the endplates 196a and 196b of adjacent vertebrae 102a, 102b, respectively, to distract or separate. The distraction device 136 will be advanced out of the cannula 142 until the distraction device 136 has completely exited the cannula 142 or the support structure 141 has attained the desired height. Typically, the distraction device 136 is advanced out of the cannula until the height of the support structure 141 is such that it returns the endplates 196a, 196b to a normal position, as illustrated in FIG. 26D.

In a procedure in which the distraction device 136 is designed to be advanced completely out of the cannula 142, the desired height of the support structure 141 is pre-determined and a distraction device of an appropriate size is chosen for use. In a procedure in which the distraction device 136 is deployed until the desired height of the support structure 141 is attained, the height of the support structure may be monitored under fluoroscopy, and once the support structure has reached the desired height, the distraction device may be severed at a location near the distal end portion of the cannula.

Upon deployment, the distraction device restores disk height and stabilizes the vertebral column. Depending on the amount of nucleus pulpous tissue removed and the deployment location of the support structure, the resident volume of the support structure may be substantially empty or may contain some nucleus pulpous tissue. Optionally, bone filler, such as bone cement, allograph or autograph, or other therapeutic drugs may be inserted into the resident volume defined by the support structure and/or around the support structure to aid in stabilization of the device and/or to promote bone fusion between the adjacent vertebrae.

Figure 26E:
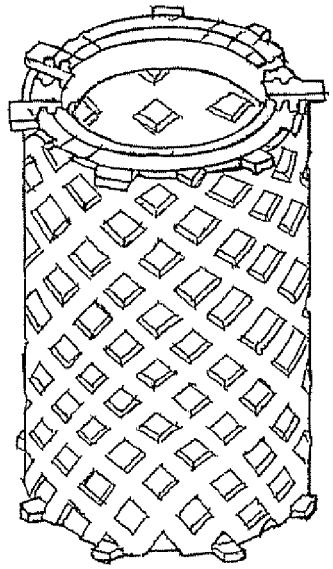
FIG. 26E is an illustration of a prior art device in which a "cage" is used for vertebral body replacement.
Figure 26F:
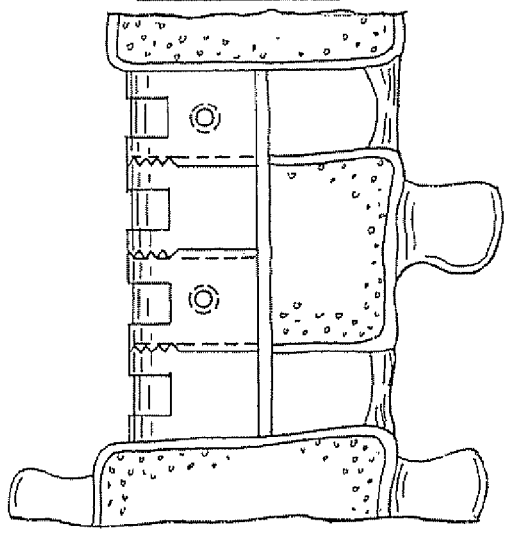
FIG. 26F is an illustration of another prior art device used for vertebral body replacement.

FIGS. 26E and 26F illustrate prior art devices, also sometimes referred to as "cages," that are used in vertebral body replacement (VBR) procedures. In a VBR procedure using such cage type devices, a portion of or the entire vertebral body is removed, and the cage is inserted into the space of the removed vertebral body. Similar to the prior art cage described above, cages of the type illustrated in FIG. 26E have a fixed size that does not substantially change before, during or after deployment. Thus, a relatively large incision is made in a patient's back and spinal tissues to implant such a device. Additionally, the procedure may require the use of a separate device to distract the tissue in order to accommodate insertion of the device.

The prior art device illustrated in FIG. 26F is somewhat different than that of the one shown in FIG. 26E in that it has individual sections which are inserted to build the device or cage. Again these sections are relatively large and require a relatively large incision for implantation.

Figure 26G:
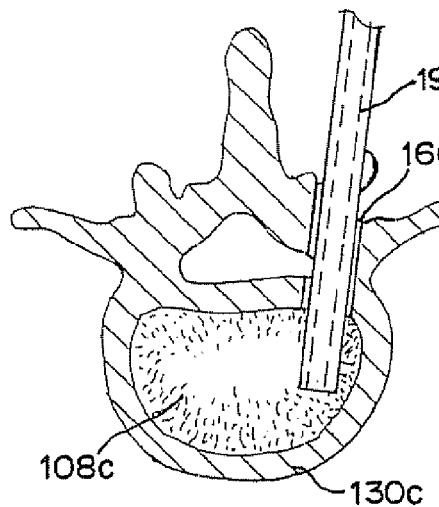
FIG. 26G is a top cross-sectional view of a vertebra shown with a vertebral bone removal inserted into the vertebra for vertebral body bone removal.

In one minimally invasive partial VBR procedure of the present invention, a vertebral bone removal tool 197 is inserted through a small access hole 160c of a vertebral body 130c as illustrated in FIG. 26G. The vertebral bone removal tool 197 can be used to remove a portion of the vertebral body or completely remove the vertebral body using endoscopic techniques and procedures generally known to those skilled in the art. Typically, this procedure is use to remove damaged vertebral bone.

Figure 26H:
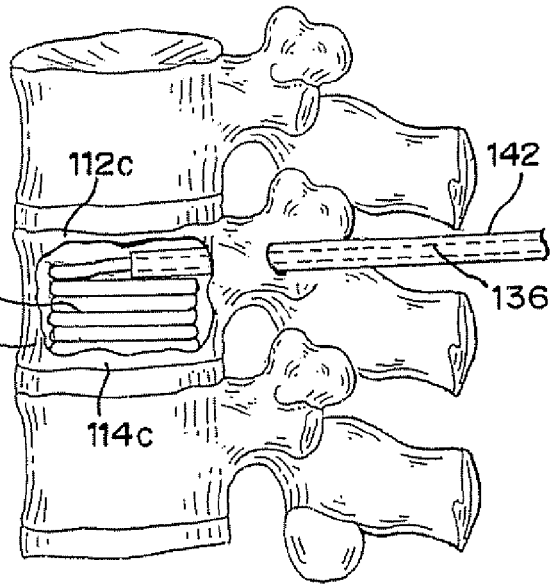
FIG. 26H is a side view of the vertebra of FIG. 26G shown within a section of a vertebral column and having portions broken away to show the delivery of a distraction device into the space created by removal of vertebral body bone.
Figure 26I:
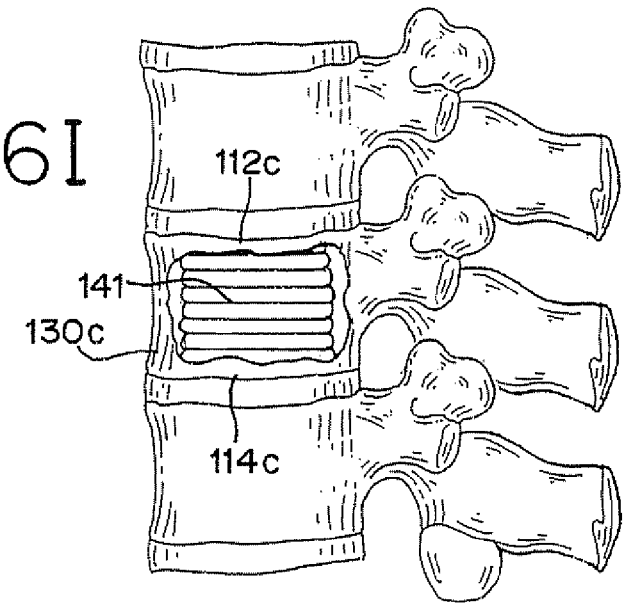
FIG. 26I is a side view of the vertebra of FIG. 26G shown within a section of a vertebral column and having portions broken away to show the distraction device completely deployed within the vertebral body.

Referring to FIG. 26H, after the damaged cancellous bone 108c has been removed, a delivery cannula 142 is inserted through the access hole 160c and a distraction device 136 is deployed into the vertebral body 130c through the cannula, using similar procedures and techniques as described above. As the distraction device 136 is deployed, it defines a support structure 141 that separates and supports the endplates 112c, 114c of the vertebral body 130c, as illustrated in FIG. 26I. After the distraction device 136 has been deployed, the resident volume of the support structure may be substantially empty or the resident volume may contain some cancellous bone depending on the amount of cancellous bone initially removed and the deployment location of the support structure. In any event, the distraction device itself does not compress the cancellous tissue to form a cavity or void volume. Optionally, bone filler or therapeutic drugs may be inserted into the resident volume and/or around the support structure to stabilize the support structure and/or to promote bone fusion.

Figure 26J:
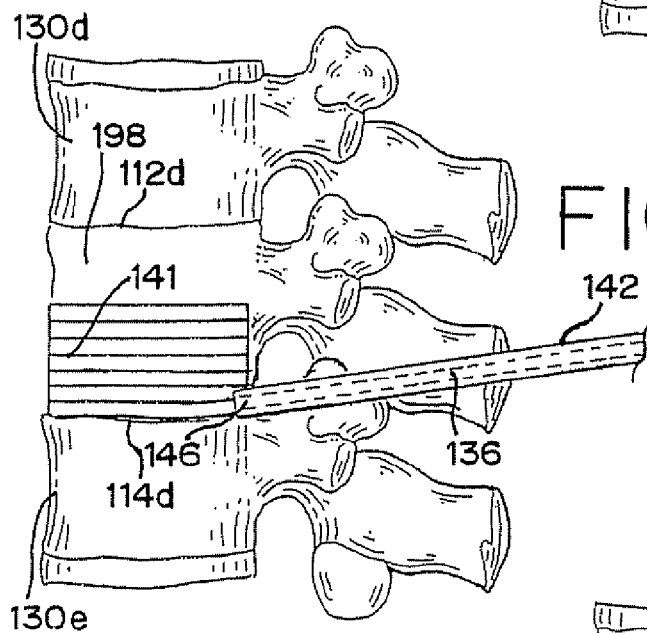
FIG. 26J is a side view of a section of a vertebral column in which the vertebral body of one of the vertebra along with the adjacent disks have been substantially removed and a distraction device is being deployed into the space created by such removal.
Figure 26K:
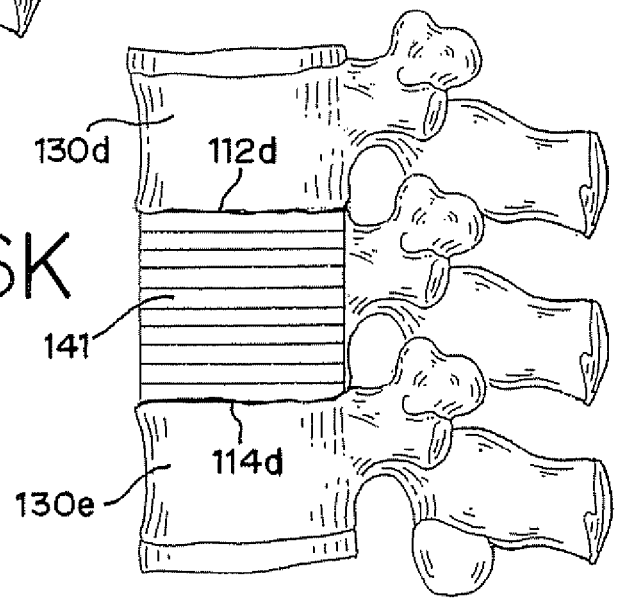
FIG. 26K is a side view of the vertebral column section of FIG. 26J shown with the distraction device completely deployed.

In one minimally invasive method of a total VBR procedure, the vertebral body removal tool described above is used to move substantially all of a vertebral body, and optionally, a disk removal tool is used to substantially remove the adjacent disks. Referring to FIG. 26J, the distal end portion 146 of a cannula 142 can be inserted into the space 198 created by the removal of the vertebral body and/or adjacent disks, and a distraction device 136 can deploy into the space, using similar minimally invasive procedures and techniques described above. Upon exiting the cannula 142, the distraction device 136 forms a support structure 141 that increases in height as the distraction device is deployed. As the support structure 141 increases in height, it contacts endplate 112d of superior vertebra 130d and endplate 114d of inferior vertebra 130e to distract and support the vertebrae in a spaced-a-part relation, as illustrated in FIG. 26K.

The deployed support structure 141 provides support and stabilizes the vertebra column. Optionally, bone filler or therapeutic drugs may be inserted into the resident volume and around the support structure to stabilize the support structure and/or to promote bone fusion.

Figure 27:
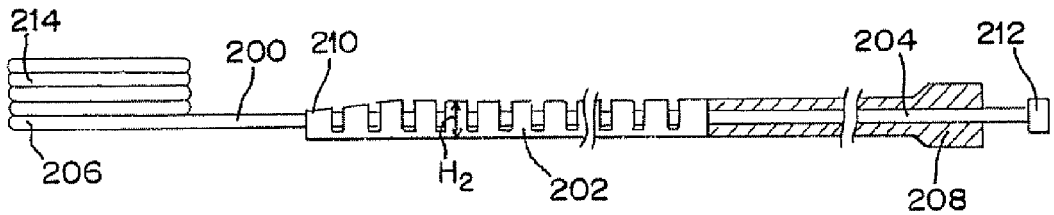
FIG. 27 is a partial cross-sectional side view of another embodiment of a distraction device and delivery system employing a pusher for advancing the distraction device over a guide wire.

FIG. 27 illustrates another embodiment of the distraction device and delivery system of the present invention. In this embodiment, the distraction device 202 is deployed with the aid of a guide wire or delivery track 200. Prior to deployment, the distraction device 202 preferably has an elongated generally linear shape and includes a center bore or passageway (shown in FIG. 39-FIG. 48) for slidably mounting onto the guide wire. The distraction device 202 should be sufficiently flexible to follow along the contour of the guide wire 200 for example, the distraction device 202 may be required to take on a generally elongated shape for mounting on a guide wire for deployment into the treatment site and a generally coil or spring shape within the treatment site.

The distraction device 202 is preferably made from biocompatible materials that are suitable for long term implantation into human tissue in the treatment of degenerative tissue, trauma or metastatic conditions or where a tissue distraction device is needed. The material used may also be a biological material such as, Calcium Phosphate, Tricalicum Phosphate, Hydroxyapatite, or any other suitable biological material. The biocompatible materials may be PEEK (polyetheretherketone), Nylon, NiTi or any other suitable. The material may be solid or porous for tissue ingrowth, and may elute therapeutic or growth enhancing agents. One of the advantages of using biological or biocompatible material to treat vertebral compression fractures is that these elements have a more natural like substance. However, other materials could be used and still be within the scope of the present invention.

Figure 44:
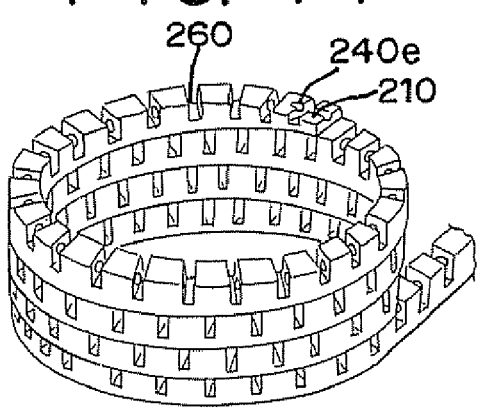

The guide wire 200 includes a proximal end portion 204 and a distal end portion 206. The distal end portion, in a deployed state, preferably defines a multi-tiered arrangement, scaffolding or platform, such as the illustrated coil or helical shape with a plurality of stacked windings, as shown in FIG. 27. The shape of distal end portion of the guide wire in a deployed state may be predetermined. Preferably, at least the coil shaped distal end portion 206 of the guide wire 200 is made of a shape memory material, such as a Nitinol or a polymer having shape memory characteristics, so that the guide wire can be deformed into a generally straight configuration prior to or during deployment of the guide wire into the treatment site, and then allowed to reform into its initial coil shape within the treatment site. With this arrangement, the guide wire itself may act as an initial distraction device, contacting the endplates of the vertebra and forcing them apart. For that purpose, the guide wire may also have a cross-sectional shape (e.g., oval) that tends to reduce contact force with endplates or to keep contact force within an acceptable range. After the coiled distal end portion 206 of the guide wire has attained the desired positioned within the treatment site, the distraction device 202 is inserted onto the proximal end portion 204 of the guide wire followed by a pusher 208. Optionally, the distal end portion 210 of the distraction device can be tapered, ramped or otherwise configured (as illustrated in FIGS. 27 and 44) to facilitate insertion and passage of the distraction device through the bone and between the tissue to be distracted.

Figure 28:
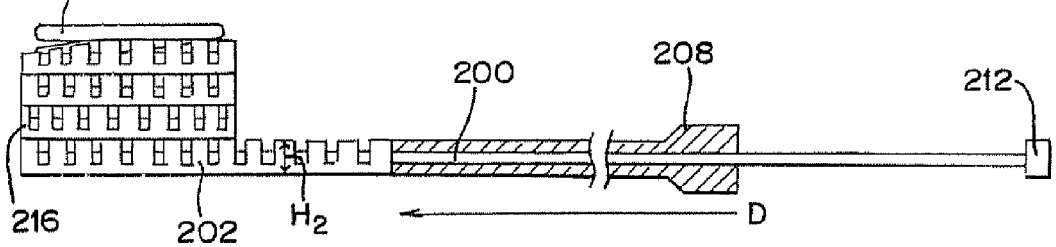
FIG. 28 is a partial cross-sectional side view of the distraction device delivery system of FIG. 27, with the pusher advanced distally and the distraction device partially advanced over a coiled section of the guide wire.

A small knob 212 can be mounted at the proximal end portion 204 of the guide wire 200 to provide a gripping portion. The knob 212 can be held with one hand as the pusher 208 is advanced distally along the guide wire 200, indicated by arrow D in FIG. 28, with the other hand. Advancing the pusher 208 distally forces the distraction device 202 to move distally, sliding over the guide wire 200. The distraction device 202 follows along guide wire 200 into the vertebra and substantially takes the shape of the distal end portion of the guide wire to form a support structure with a multi-tiered arrangement or scaffolding. For example, in the illustrated embodiment, the distraction device 202 winds into a coil shape as it passes over the coil-shaped portion 206 of the guide wire. The distraction device 202 winds upon on itself as many times as the number of windings 214 of the guide wire to form a multi-tiered support structure or scaffolding, such as the coil or helical shaped support structure 216.

Figure 29:
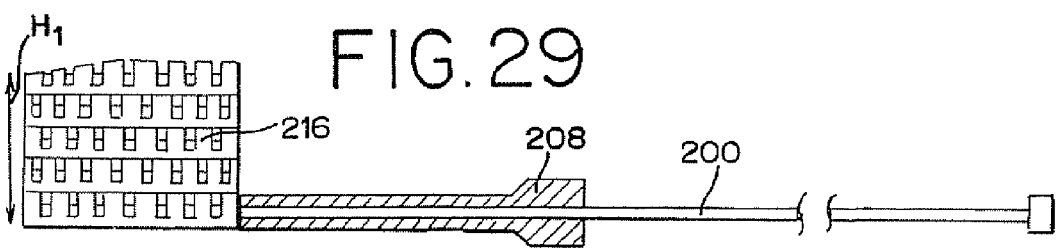
FIG. 29 is a partial cross-sectional side view of the distraction device delivery system of FIG. 27, with the distraction device substantially advanced over the coiled section of the guide wire.

FIG. 29 illustrates a completed scaffolding or support structure 216 that is defined by the coiled distraction device 202. The extent or height $H_1$ of the support structure 216 is determined generally by multiplying the number of turns or windings by the height $H_2$ (shown in FIG. 27) of the elongated distraction device. If desired, the guide wire 200 can now be removed from the deployed distraction device 202. The removal of the guide wire 200 can be accomplished by holding the pusher 208 in place while pulling the proximal end 204 of the guide wire 200 in a proximal direction. Optionally, depending on the treatment, the guide wire 200 can remain in place with the distraction device 202 to further strengthen and stabilize the support structure 216 defined of distraction device 202. In that usage, the proximal end 204 of the guide wire 200 could be severed from the remainder of the guide wire by cutting, unscrewing or other means as it is known in the art.

It should therefore be apparent from the above that the present invention is particularly advantageous and conducive to minimally invasive surgical procedures for treatment of the spine. In accordance with this aspect of the present invention only a single access opening is required, which may be made transcutaneously and through the appropriate spinal bone or other tissue. Through this single opening a relatively large three-dimensional support structure can be built within the confined space of an individual vertebra or between adjoining vertebrae. Insertion of the distraction device may be aided by an introduction cannula or sheath, or the distraction device itself may be directly advanced through an access opening without the need for a cannula or other advancing aid. In any event, in the illustrated embodiment a relatively large support structure is built or formed in situ through a relatively much smaller access opening, providing the benefits of more drastic and invasive surgical approaches with the safety and ease of minimally invasive techniques.

Figure 30:
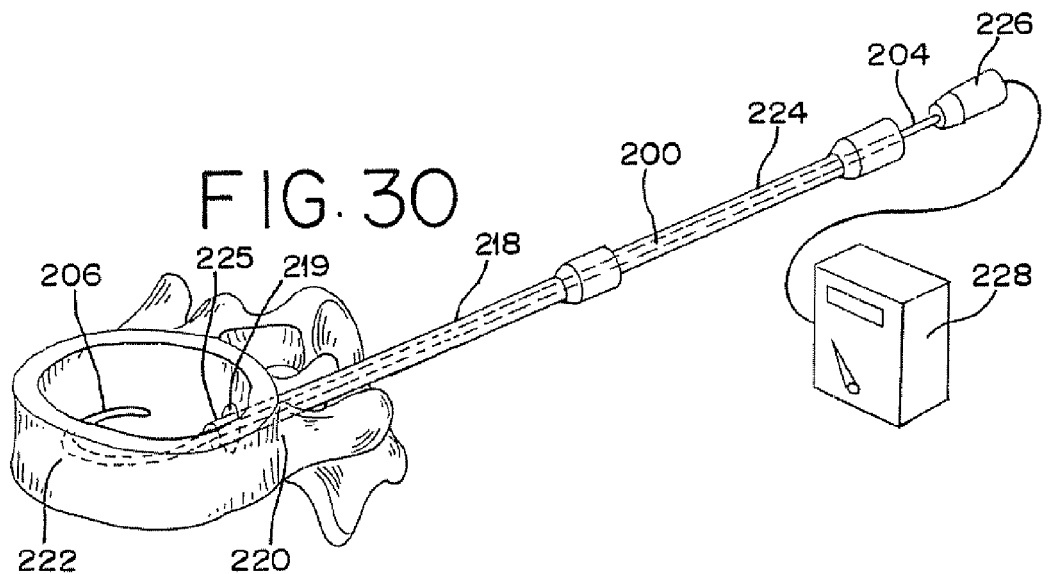
FIG. 30 is a perspective view of a vertebra with the superior endplate removed to show the delivery of a guide wire into the vertebral body.

FIG. 30 through FIG. 35 illustrate the deployment of the distraction device 202 into a vertebral body. Referring to FIG. 30, an introducer sheath 218 is introduced through the back of a patient while the patient is lying in a prone position. Fluoroscopic guidance using a biplane imaging system for better visualization of the spine may be used to help guide the delivery system to the desired location. The introducer sheath 218 has a sharp tip to help penetrate the bone structure typically through the pedicle 220 of the vertebral body 222 (in the transpedicular approach). Once the introducer sheath 218 has passed through or created a passage 219 in the pedicle 220 and is in the desired position, which can be confirmed by imaging, a delivery cannula 224 may be inserted into the introducer sheath 218 and the guide wire 200 is advanced forward through the cannula. Alternatively, the guide wire may be inserted through the cannula without an introducer sheath.

As explained above, the guide wire 200 is preferably made of a shape memory material that has an initial or free state in the shape of a coil or spring. As the guide wire 200 is inserted into the cannula 224, the cannula constrains the guide wire into a generally elongated linear configuration, allowing an easy and minimally invasive deployment of the guide wire into the treatment site. Because of the shape memory properties, the guide wire 200 will return to its coil-shaped free state once the constraint is removed, i.e., as the guide wire exits the distal end portion 225 of the cannula 224 and enters the vertebral body 222. The guide wire 200 can be advanced through the cannula 224 manually or with the aid of an advancing mechanism, such as a ratcheting mechanism, e.g., the ratchet gun shown in FIG. 58.

In order to improve the rate and ease of penetration of the guide wire 200 through bone and other tissues, an energy system can be operatively connected to the guide wire to transmit energy that enables the tip of the wire to drill through the tissue or bone to access the desired site or obtain the desire configuration. In the illustrated embodiment, the proximal end portion 204 of the guide wire 200 can be coupled to an energy system, such as a transducer assembly 226 with a piezoelectric element that produces ultrasonic vibrations at a specific frequency to help the guide wire penetrate the bony structure of the vertebral body. Such energy system could include an energy source 228 coupled to the transducer 226 capable of propagating ultrasonic energy at frequencies suitable for drilling a pathway into dense material, such as bone. The use of such energy systems that may be employed in the present invention are described in U.S. Pat. No. 6,498,421 to Oh which discloses drilling, U.S. Pat. No. 6,899,715 to Beaty which discloses boring and U.S. Pat. No. 4,838,853 to Parisi which discloses cutting using ultrasonic energy. Such devices have also been used in the vascular system to penetrate through arterial blood clots as described in U.S. Pat. No. 6,929,632 to Nita. All of the aforementioned patents are hereby incorporated herein by reference.

It will be understood that the energy system as described herein can also be used in a substantially similar manner to aid in the delivery of the above described distraction device 136 of FIG. 12. It will also be understood that the use of a transducer assembly is optional and that in some procedures it is advantageous to deploy the guide wire 200 without the aid of a transducer assembly. In those instances in which a transducer assembly is not used, the guide wire can be deployed in a manner generally similar to that previously described above with respect to the deployment of the distraction device 136 of FIG. 12.

As the guide wire 200 exits the distal end portion 225 of the cannula 224 and enters the vertebral body 222, the distal end portion 206 of the guide wire begins to return to its unconstrained shape, i.e., the distal end portion of the guide wire begins to wind into its coil shape. Referring to FIG. 31, the guide wire 200 is advanced and deployed into cancellous bone of the vertebral body 222 until the coil shape reaches the desired height or has the desired number of loops or windings 214. As noted earlier, the guide wire itself may function to distract or separate the endplates of a damaged vertebra. Preferably, the guide wire 200 is advanced until the coiled portion of the guide wire attains a height that spans the gap between the superior endplate and the inferior endplate. Further, in certain treatments, as noted above the guide wire 200 may itself contact the endplates of the vertebral body and function to cause distraction of the endplates and enlargement of the vertical height of the vertebral body, restoring or partially restoring the height of the vertebra. Alternatively, the coil shaped guide wire may be deployed within the vertebral body without any distraction or minimal distraction of the endplates.

Referring to FIG. 32, after the guide wire 200 has achieved a desired deployed configuration, the introducer sheath and cannula can be retracted and removed from the system and the transducer assembly can be disconnected. At this stage, the coiled distal end portion 206 of the guide wire 200 is deployed within the vertebral body 222, and the proximal end portion 204 of the guide wire is extending out of the passageway 219 of the vertebral body. The proximal end portion 204 of the guide wire defines an insertion path or track for the distraction device 202. Alternatively, when desired, the introducer sheath and/or cannula can be left in place, and the distraction device can be deployed into the vertebral body through the introducer sheath, the cannula or both.

One of the advantages of removing the introducer sheath and the cannula from the system is that such removal allows for a larger passageway into the vertebral body. The larger passageway makes it possible to employ distraction devices or implants having larger dimensions. Thus, when the introducer sheath and cannula are removed, the dimensions of the distraction device can be larger because the size of the distraction device is not constrained or controlled by the size of the introducer sheath or cannula. One advantage of employing a larger distraction device is that the larger distraction device provides a larger surface area that disperses the loading forces acting on the device and results in less pressure being placed on any given portion of the device or on the surface of the vertebral body contacted by the distraction device.

As illustrated in FIG. 32, the distraction device 202 is inserted over the proximal end portion (not shown) of the guide wire 200, and a pusher member 208 is placed over the guide wire behind or proximal the distraction device. As the pusher member 208 is advanced, it contacts the distraction device 202 and advances it forward or distally over the guide wire 200. A ratchet device (shown in FIG. 58) or other advancement mechanism may also be employed to assist in advancing the pusher member incrementally.

Referring to FIG. 33, as the distraction device 202 is advanced forward (distally) over the guide wire 200, the guide wire guides the distraction device through the passageway 219 and into vertebral body 222. As illustrated in FIGS. 27 and 44 and as noted above, the distal end 210 of the distraction device can be tapered, ramped or otherwise shaped to aid in passing through tissue.

In the vertebral body, the distraction device 202 follows along the coiled shaped portion 206 of the guide wire 200 and winds into a coil shaped support structure 216 as shown in FIGS. 34 and 35. The side slots in the distraction device allow it to bend more easily and follow the contour of the guide wire. With each formation of an additional coil or windings 236 of the support structure 216, the support structure increases in height. As the support structure 216 increases in height, it distracts and supports the endplates of the vertebra, restoring or partially restoring vertebral height and stabilizing the vertebral body 222. When treating a fractured vertebral body, the distraction of the endplates stabilizes the fracture because the load is no longer applying pressure onto the fractured section or onto the fragmented pieces that can pressure the nerve endings surrounding the vertebral body, and thus back pain is reduced.

One advantage of this embodiment of the distraction device, as noted above, is that it can be inserted through a small access hole and a much larger three dimensional support structure, such as a multi-tiered arrangement or scaffolding, can be built within a limited or confined space between or within the tissue layers. For instance the distraction device 202 can be inserted through a small access hole and the support structure 216 can be built one loop at the time by adding one thickness of the distraction device over another one. As an example, the average vertebral body is 18 mm in height. As illustrated in FIG. 2, after a vertebral body compression fracture, the vertebral body can be about half of the height of a normal vertebral body, which would result in a compressed body of about 9 mm. By way of example, a guide wire in the form a wire with a 1 mm in diameter with a pitch about half of the wire size would require about 5 loops to span from endplate to endplate. When the distraction device is inserted onto the guide member, it will start winding along the loops and distract or push up and down in the axial direction which may benefit from the mechanical advantage of advancing over a coil. Because the fractured body has less resistance, it will expand the distance between the two endplates until they are preferably at the pre-fractured position, as illustrated in FIG. 35.

After the distraction device 202 has been deployed, the guide wire 200 can be retracted from the distraction device and removed from the system. This can be accomplished by holding the pusher member 208 in place while retracting the guide wire 200 in a proximal direction. For example, the guide wire 200 can be retracted proximally by reversing the advancing mechanism, e.g., the ratchet mechanism of the delivery gun, while keeping the pusher member in place.

The distraction device of the present invention is preferably but not exclusively used with bone filler material to add stability to the distraction device and support between the distracted tissue, i.e., the endplates of the vertebra. Bone filler may be introduced in a variety of ways. As illustrated in FIG. 36 and FIG. 37, a small tubular element or needle 238 may be inserted between the windings 236 of the support structure or within a center hole of distraction device 202, for example central channel 240 of FIG. 39, so that a bone filler material 242, preferably bone graft material or bone cement, can be injected into the inner area or resident volume 244 defined by the support structure 216. The resident volume 244 may or may not contain cancellous bone. The needle 238 could be connected to syringe or other type injection device. In the illustrated embodiment, the distraction device 202 includes slots 246 that communicate with the central channel. The slots 246 are arranged so that the slots direct the injected bone filler 242 to resident volume 244 defined by the support structure 216. The support structure 216 acts as a barrier that limits and/or directs the movement of the bone filler 242 and substantially prevents the bone filler from spreading to areas outside of the support structure 216. In other words, the support structure 216 can serve as a containment device that surrounds the bone filler 242 and contains it within resident volume 244 defined by the support structure 216. The support structure/containment device 216 prevents undesired leakage or extravasation. Preferably, the bone filler 242 is injected until it has completely filled the resident volume 244 defined by the support structure 216 as illustrated in FIG. 38.

The distraction device may have a variety of configurations without departing from the present disclosure. The different configurations provide a variety of advantageous features of the distraction device. One aspect to be considered in regards to an implanted distraction device is the ability of the device to resist different forces, such as compressive and axial forces. It is easily understood that the device can resist compressive loading wherein the force on the distraction device is axial. However, additional lateral or translation forces can also act on the device when the body is moving.

FIGS. 39-48 illustrate examples of possible profiles of the distraction device and the multi-tiered support structures that can be formed by such distraction devices. The various profiles aid in shape retention so as to keep the distraction device in the shape of the deployed support structure and substantially accommodate resistance to both compressive and lateral forces, among other advantageous features. All of the embodiments in these figures preferably include a channel generally designated 240-240i for mounting the distraction device onto the guide wire. The central channel in some embodiments also can be utilized for directing the flow of bone filler or the delivery of drugs or other fluid materials.

Figure 39:
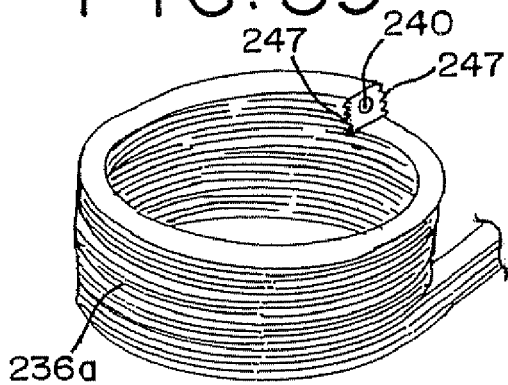
FIGS. 39-48 are perspective views of different embodiments of distraction devices, showing a variety of shapes and cross-sectional profiles including profiles that all allow the distraction device to bend or curve.
Figure 40:
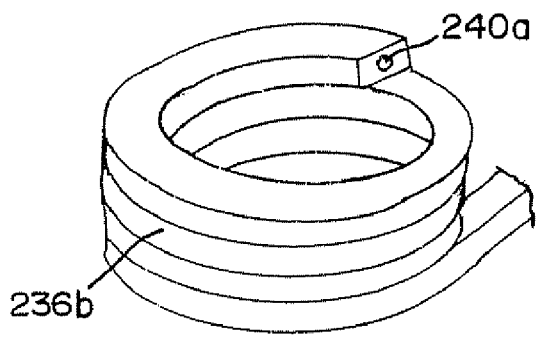

In FIG. 39, the cross-sectional profile is generally square and in FIG. 40, the cross-sectional profile is generally rectangular. Both of these embodiments provide windings 236a and 236b having substantially flat surfaces that contact flat surfaces of adjacent windings. The contact between the surfaces of each winding provides a support structure, which is very good at resisting compressive forces. Additionally, as illustrated in FIG. 39 the distraction device can have a porous coating 247 throughout or at least on the sides of the distraction device for better integration into the tissue to be treated.

Figure 41:
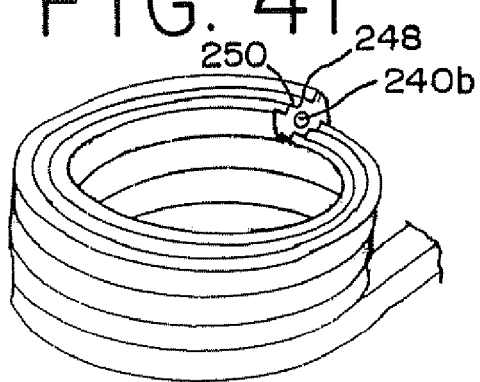

In FIG. 41, the cross-sectional shape is a custom tongue and groove profile having a corrugated shape with a plurality of peaks 248 and valleys 250. The peaks 248 and valleys 250 of each winding engage these of the next adjacent winding to provide interfering surface that adds stability and resists lateral slippage.

Figure 42:
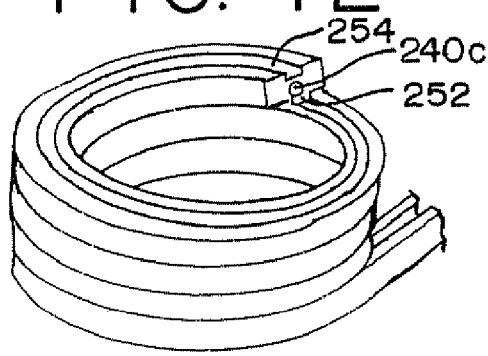

In FIG. 42, the cross-sectional shape is a custom profile with a single tongue and groove configuration. The distraction device has a groove 254 formed on one surface and a raised rib or tongue 252 formed on the opposite surface so that when wound together the tongue extends into the groove of an adjacent winding and the groove receives the tongue of an adjacent winding. Again the tongue 252 and groove 254 engage each other to provide interfering surfaces that add stability and resists slippage and shifting due to lateral forces.

Figure 43:
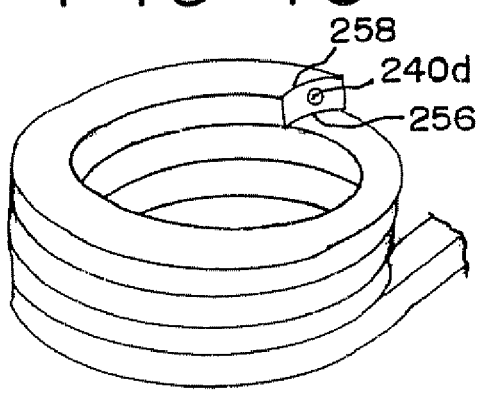

In FIG. 43, the cross-sectional shape is a custom profile having opposed concave surface 256 and a convex surface 258. When the distraction device forms a support structure the concave and convex surfaces 256, 258 engage the mating convex or concave surface of adjacent windings to add stability and reduce slippage and shifting due to lateral forces.

FIGS. 44-48 illustrate embodiments of the distraction device which include features that assist in directing and limiting the direction bone filler injected into the treatment site. In the illustrated embodiments, materials, such as bone filler or medications, can be injected into one of the channels 240e-240i. The material will flow through the channel and into slots located in the distraction device. The slots direct and/or limit the flow of the material to a specific region within the treatment site. The illustrated embodiments also include features that aid in the insertion of the distraction device and assist in the turning of the distraction device as it is guided over the guide wire. For example, the slots located in the distraction device enhances the flexibility of the distraction device, making it easier for the distraction device to follow the contour of the guide wire.

FIG. 44 illustrates a distraction device wherein the distraction device includes upward directed slots 260. When bone filler is injected into the channel 240e, the boner filler flows out of the slots 260 and into areas on both the inside and outside of the distraction device support structure.

Figure 45:
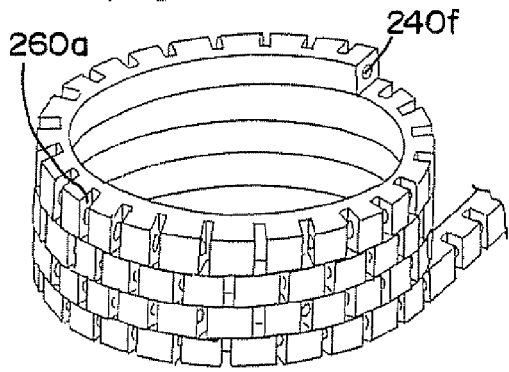

In FIG. 45, the distraction device includes outwardly facing slots 260a. When bone filler is injected into the channel 240f, the bone filler flows out of the slots 260a into the area outside of the distraction device support structure. Thus, the slots 260a direct the flow of bone filler toward the outside of the distraction device, and the distraction device support structure acts as a barrier, leaving the inner area defined by the distraction device substantially free of bone filler material.

Figure 46:
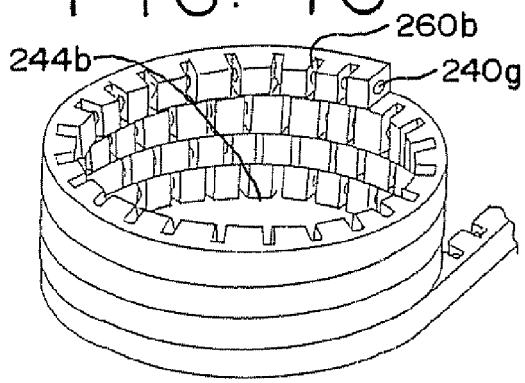

In FIG. 46, the distraction device includes inwardly facing slots 260b. When bone filler is injected into the channel 240g, the bone filler flows out of the slots 260b and into the inner space 244b defined by the distraction device. Thus, the slots 260b direct and limit the flow of bone filler toward the inside of the distraction device, and the distraction device acts like a container that contains the bone filler within the distraction device, leaving the outside region of the distraction device substantially free of bone filler material.

Figure 47:
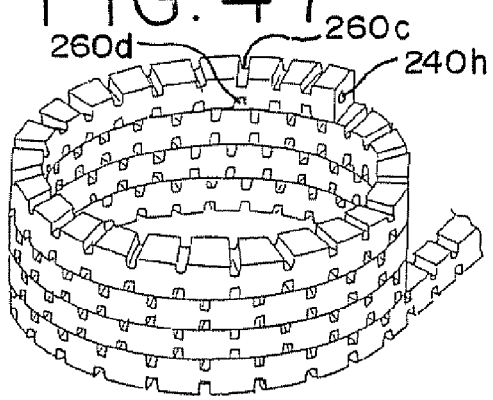

In FIG. 47, the distraction device has upwardly and downwardly facing slots 260c, 260d, which allows bone filler to flow into regions inside and outside of the distraction device.

Figure 48:
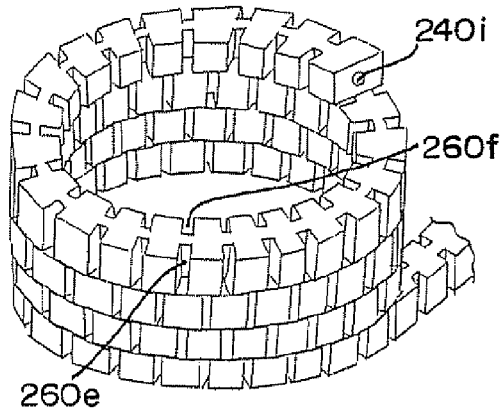

In FIG. 48, the distraction device has inwardly and outwardly facing slots 260e, 260f. In this embodiment, the inwardly and outwardly facing slots 260e, 260f direct the bone filler toward both the inner space defined by the distraction device and the region outside of the distraction device.

The size and dimension of the distraction device when used for the treatment of vertebral compression fracture is preferably of a size that can be inserted through a cannula no larger that about a 6 gauge size (working diameter about 0.173 inches (about 4.39 mm)) which would allow the distraction device to have a generally square profile of about 0.118 inches×0.118 inches (about 3 mm×3 mm). Other sizes and dimensions could be used depending on the application. The length of the distraction device could be pre-determined or could be cut to fit during the treatment.

The construction of the distraction device could be accomplished using several techniques known in the art, including but not limited to molding, machining or extruding. It is also understood that the delivery coil or guide member could have different profiles and different shapes according to the application requirements.

Figure 48A:
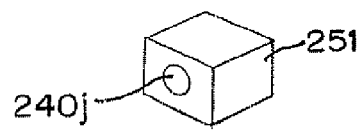
FIG. 48A is one embodiment of a distraction device element.
Figure 48B:
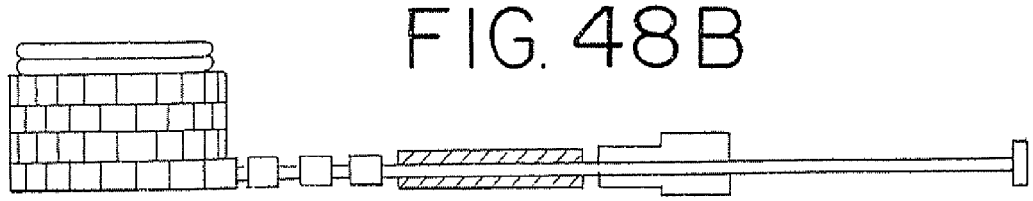
FIG. 48B is a partial cross-sectional side view of one embodiment of a distraction device having multiple distraction device elements slidably mounted on a guide wire.

In one embodiment, referring to FIG. 48a, the distraction device could be comprised of a plurality of individual distraction device elements 251, each including a hole 240j for mounting onto the guide wire 200a for insertion into the vertebral body. The individual distraction device elements 48a could have a cube-like configuration or could be longer or shorter in length or width depending on the desired use. When individual distraction device elements 251 are used, the distraction device is preferably stabilized by leaving the guide wire 200 implanted within the distraction device or with the aid of cement introduced into the inner area defined by the distraction device or at least in contact with the spiral or both.

The distraction device also can be constructed by linking a plurality of individual distraction device elements together to form a chain-like structure. For example, a thin section of material could be connected to a plurality of cube-like distraction device elements to retain all of the elements together, forming a line or deformable linear structure. The individual distraction device elements can be similarly sized and shaped, or alternatively, each individual element can be a different size and shape.

Alternatively, the distraction device can be formed from a bar or rod shaped in which a multitude of slots that can be machined into the starting bar or rod at regular or random intervals. A channel may be bored through the middle of the distraction device for mounting and sliding onto a guide wire.

The distraction devices and guide wires of the present invention can be deployed by a variety of different methods and with a variety of apparatus. It will be understood that the deployment methods and apparatus disclosed in FIGS. 49-58 are examples of what could be used to deliver distraction devices of the type generally disclosed in FIG. 12 or guide wires of the type generally disclosed in FIG. 27. For convenience, the aforementioned deployment methods and apparatus will be described in relation to the deployment of distraction devices.

The distraction device may be made more effective for certain procedures by using multiple coil or spring-shaped distraction devices in order to speed up the procedure and also increase the surface area in contact with the tissue or endplates in the case of treating vertebras. In circumstances where smaller distraction devices are used, but the surgeon desires to have the maximum surface area to support the two endplates of a vertebra, the surgeon can used a bi-transpedicular approach for instance as shown in FIG. 49. Two holes are drilled into the vertebral body 262 and two cannulas 264a, 264b can be inserted through the holes to deliver each distraction device 266a, 266b. The surgeon may, preferably, insert one device after the other for ease of use and safety concerns. However, at the surgeon's option both could be inserted at the same time. Thus, this invention is not limited to the sequence of insertion.

Figure 50:
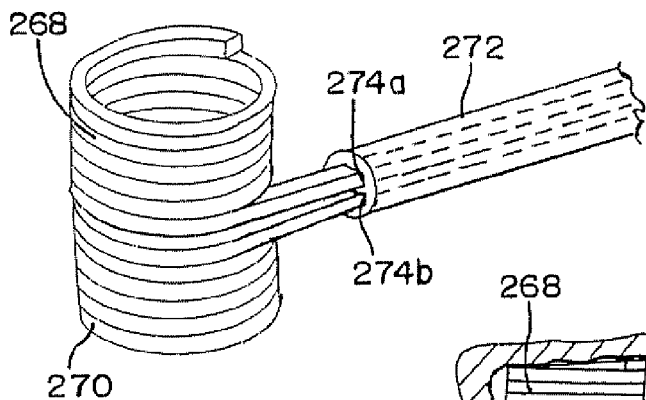
FIG. 50 is a perspective view of one embodiment of the delivery system of the present invention for placing two distraction devices or guide wires in a relative superior and inferior position.
Figure 51:
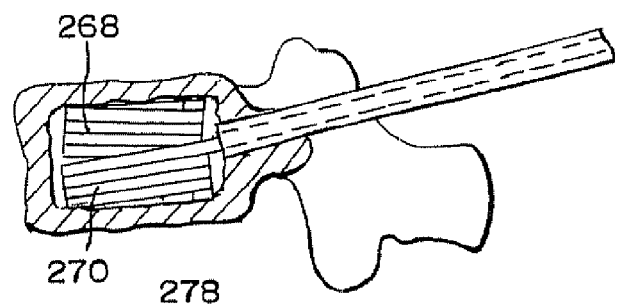
FIG. 51 is a side cross-sectional view of a vertebral body in combination with the system of FIG. 50 at least partially deployed.

A double coil or distraction device having a superior device 268 and an inferior device 270 is also shown in FIGS. 50 and 51. Each device winds in the opposite direction, therefore device 268 winds in the upward direction and device 270 winds in the downward direction. The devices are preferably delivered simultaneously but could also be delivered one at the time. Both devices 268 and 270 wind to the right relative to surgeon introducing them; however another device could have the devices that wind to the left as it might be required. The delivery cannula 272 could also have two channels 274a, 274b on its distal end to properly guide each device in its proper orientation. Since the same number of winds would be required for a given height dimension, having two devices being deployed at the same time would cut in half the time require to deliver that particular device if only one coil would be used. This embodiment is preferably employed when it is possible to access the center (height wise) of the vertebral body because the distraction device expands in both directions.

Figure 52:
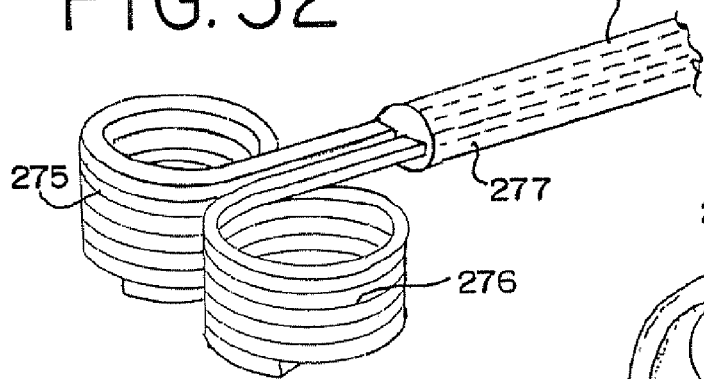
FIG. 52 is a perspective view of another embodiment of the delivery system of the present invention having a double distraction device or guide wire configuration in a relative lateral position.
Figure 53:
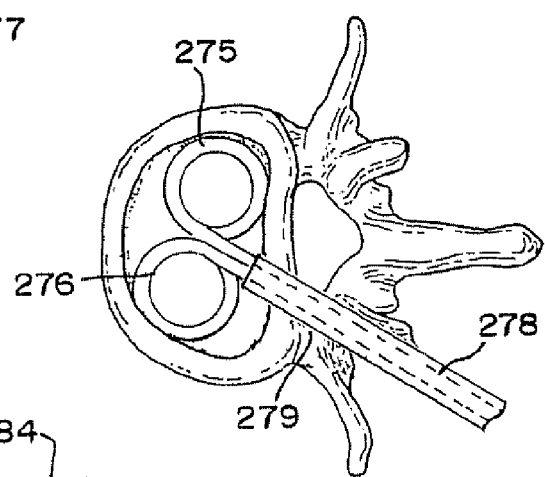
FIG. 53 is a top partial cross-sectional view of a vertebral body and the system of FIG. 52 at least partially deployed.

Another configuration of a double coil or device design is shown in FIG. 52, wherein the distraction device has a first device 275 in an anterior position and a second device 276 in a posterior position. The first device 275 winds to the right when deployed and the other device 276 winds to the left when deployed. In this embodiment, both of the devices 275, 276 wind in the downward direction; however, in another embodiment both devices could wind in the upward direction. The distal end 277 of the cannula 278 has two channels located side by side to properly guide the devices. In this case, the surface area contact is doubled which reduces the stress to the tissue or endplate as the case might be. However, the deployment time is similar as to deploying a single coil device. It might be more advantageous to use this embodiment when only one pedicle 279 or one side can be access for a medical or physical reason, as shown in FIG. 53. This way the surface contact area is significantly increased.

Figure 54:
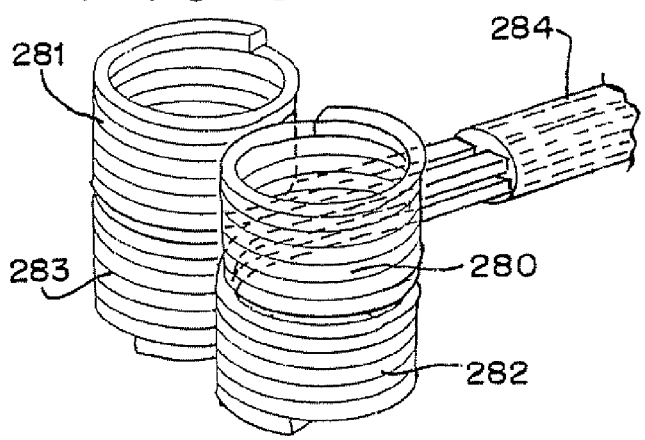
FIG. 54 is a perspective view of yet another embodiment of the system of the present invention having a quadruple distraction device or guide wire configuration in relative superior and inferior lateral positions.

In order to both reduce delivery time and double the surface contact area, another distraction device configuration is illustrated with four distraction devices in FIG. 54. Basically, it is a combination of the two previously described devices. The two devices 280 and 281 are located in a superior position and side-by-side, with device 280 winding to the right and device 281 winding to the left. Both devices also wind in the upward direction. The other two devices 282 and 283 are located in an inferior position and both are winding downwardly with device 282 winding to the left and device 283 winding to the right. This design of course, potentially requires a larger cannula 284 to accommodate the four different materials for each of the distraction devices.

Figure 55:
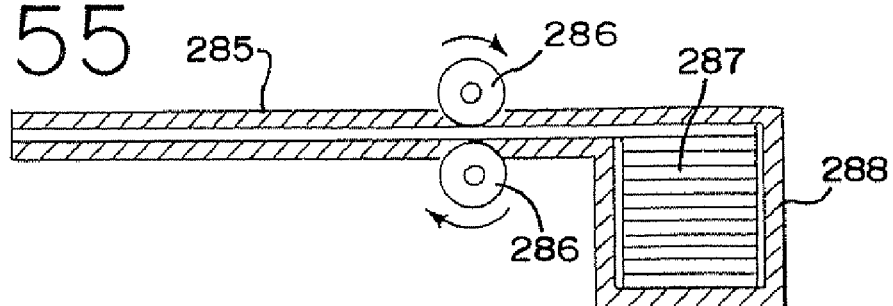
FIG. 55 is a side view of a wheel driven delivery apparatus in a starting position.

In addition to a manual pushrod advance of the distraction device, semi-automated or automated apparatus may be provided for ease of use. FIG. 55 shows a schematic representation of an automatic design using a cannula 285 for the delivery of the distraction device within the body to the treatment site. The apparatus has a set of motorized rollers 286 to push out the distraction device 287 in its un-deformed configuration from a holding cartridge 288. The controls of such an apparatus would include stop and start commands and potentially a reverse command so that the distraction device can be retrieved. It could also include indication of delivery speed and force resistance encountered by the advancing distraction device into the intended tissue in question. Additional features could be added to such apparatus as it is well know in the art.

Figure 56:
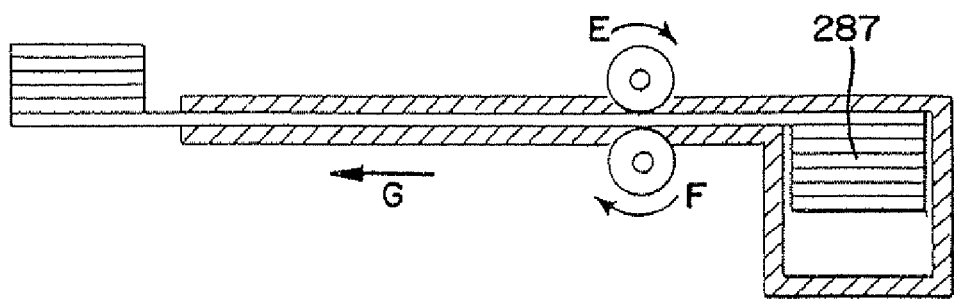
FIG. 56 is a side view of the wheel driven delivery apparatus of FIG. 55 during deployment of the distraction device.

FIG. 56 shows the coil distraction device 287 being delivered and as the rollers 286 spin in the direction represented by arrow E and F, the friction exercises onto the distraction device will make it move into the direction shown by arrow G.

Figure 57:
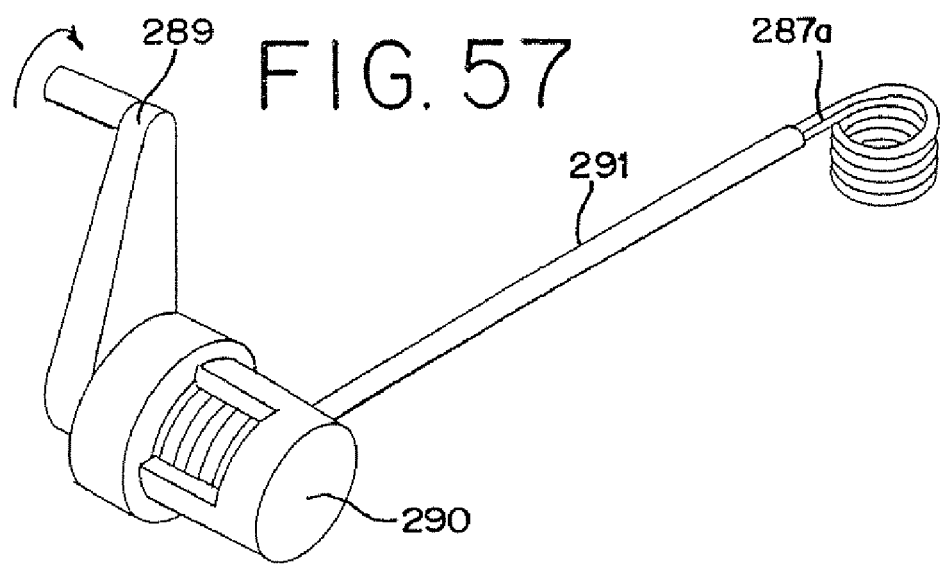
FIG. 57 is a perspective view of a spool type delivery system during deployment.

Another device and method to deliver the distraction device are illustrated in FIG. 57 as a semi-automated type of device with manual control of the delivery action. The distraction device 287a is mounted on a rotating spool which is connected to a handle 289, and carried with a housing 290. The distraction device extends through a fixed cannula 291. By turning the handle 289 in the direction indicated by arrow, the distraction device is fed along the cannula 291 until it exits at the distal end and takes its un-deformed state at the treatment site.

Figure 58:
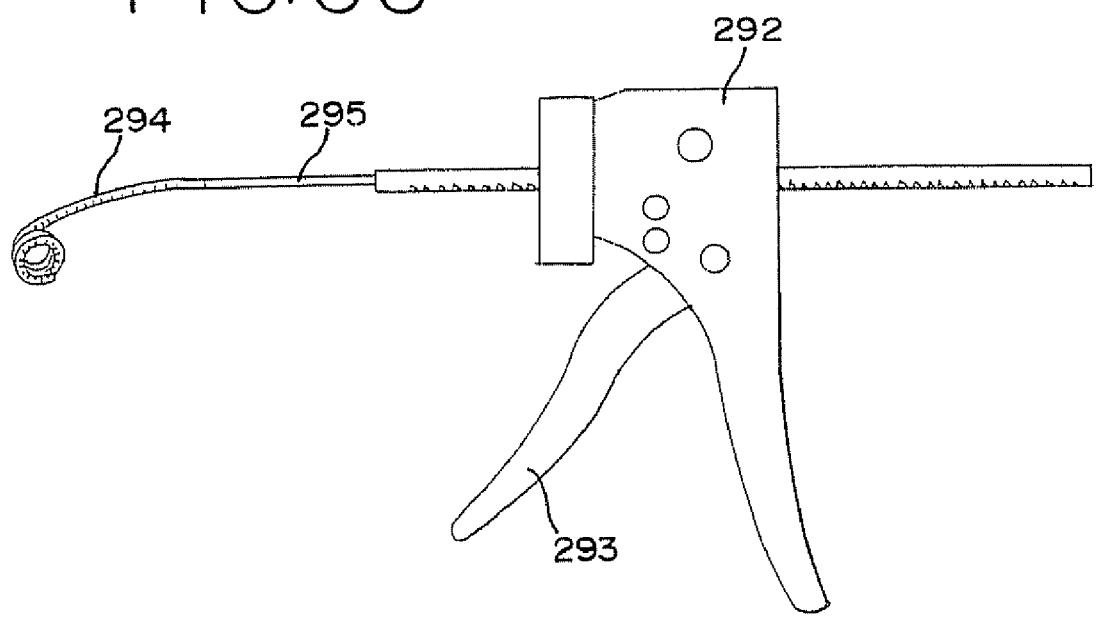
FIG. 58 is a side view of a ratchet delivery apparatus.

FIG. 58 illustrates a ratchet feed device 292 that preferably has an advancing mode and a retracting mode. In the advancing mode, upon activation of the trigger 293, the distraction device 294 advances incrementally through the cannula 295. In the illustrated embodiment, the trigger 293 is activated by repeatedly squeezing and releasing the trigger.

Figure 58A:
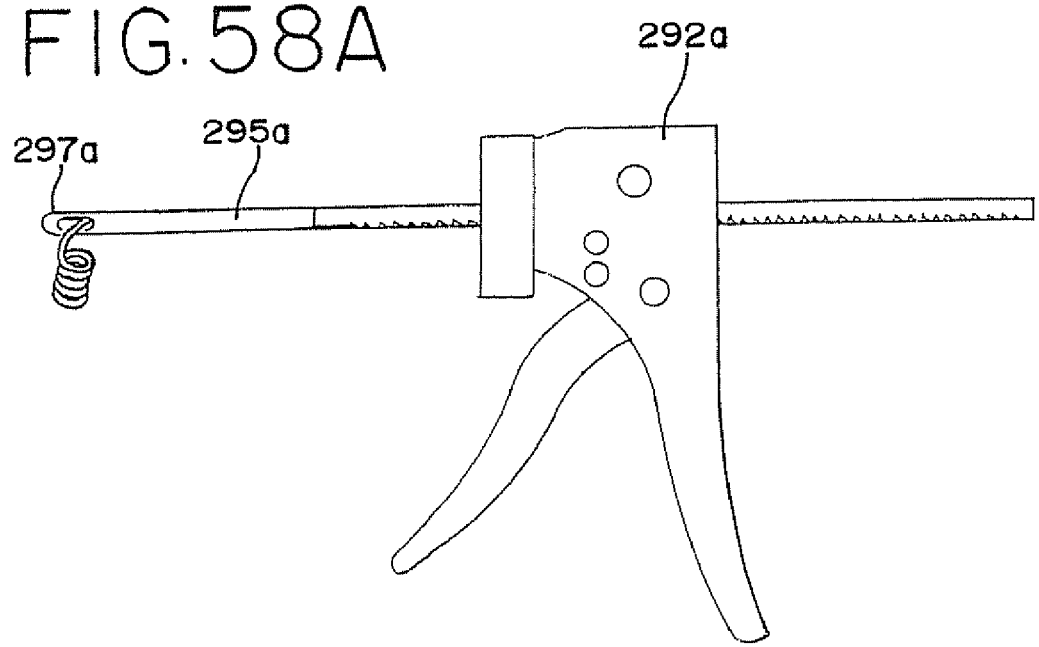
FIG. 58A is a side view of a ratchet delivery apparatus in which the distraction device or guide wire exits out of the side of the distal tip of the delivery apparatus.

FIG. 58A illustrates another embodiment of a ratchet feed device 292a in which the distraction device or guide track exits out of the side of the distal end 297a of the cannula 295a.

As noted above, the present invention relates to devices and methods to treat a condition that requires skin, tissue, organ, bone or a combination of those to be distracted from one another and supported apart of each other, either on a permanent situation or a temporary situation. It is also more specifically applicable for the treatment of vertebral compression fractures. The distraction device is also particularly well suited for the treatment of intervertebral disk treatments and spinal fusion.

Figure 59:
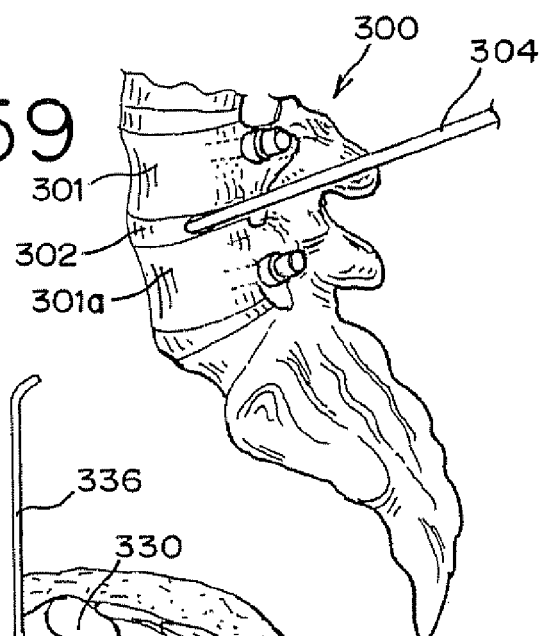
FIG. 59 is a side view of a vertebral column shown with a disk nucleus removal tool entering one of the intervertebral disk from a posterior approach.
Figure 61:
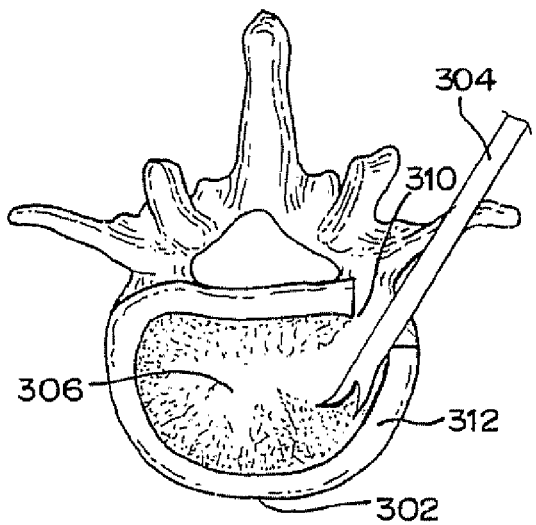
FIG. 61 is a top cross-sectional view of an intervertebral disk shown with a disk removal tool inserted into the disk for disk nucleus pulpous removal.

FIG. 59 illustrates a section of a vertebral (spinal) column 300 having adjacent vertebrae 301 and 301a and an intervertebral disk 302 located between the vertebrae 301, 301a. A disk nucleus removal tool 304, such as rongeurs, curettes, probes and dissectors, is shown accessing the disk 302 via a posterior approach. As illustrated in FIG. 61, the removal tool 304 can be inserted through a small access hole 310 in the anulus fibrous 312 to remove the disk nucleus pulpous 306 using techniques and procedures generally known to those skilled in the art.

Figure 62:
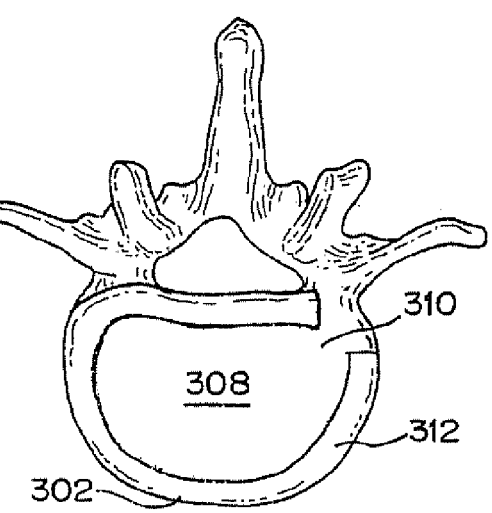
FIG. 62 is a top cross-sectional view of the intervertebral disk of FIG. 61 shown after the nucleus pulpous of the disk has been removed.

Referring to FIG. 62, an open space or disk nucleus space 308 is created by the removal of the disk nucleus 306. Additionally, the small access hole 310 that was created in the disk annulus 312 during the nucleus removal can be used to access the disk nucleus space.

Figure 63:
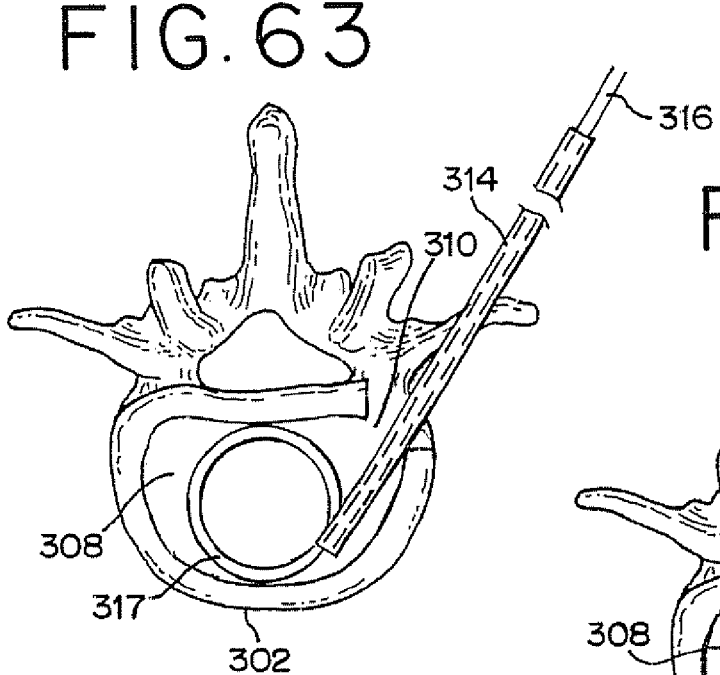
FIG. 63 is a top cross-sectional view of the intervertebral disk of FIG. 61 shown with a cannula inserted into the disk and a guide wire partially deployed within the nucleus space.
Figure 64:
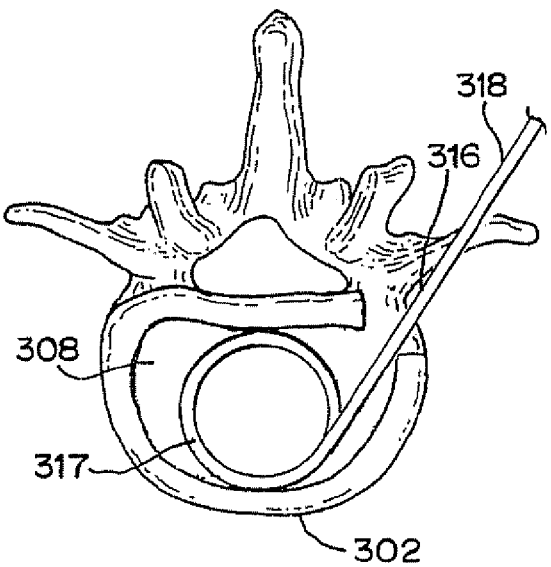
FIG. 64 is a top cross-sectional view of the intervertebral disk of FIG. 61 shown with the guide wire deployed within the nucleus disk space and the cannula removed.
Figure 63A:
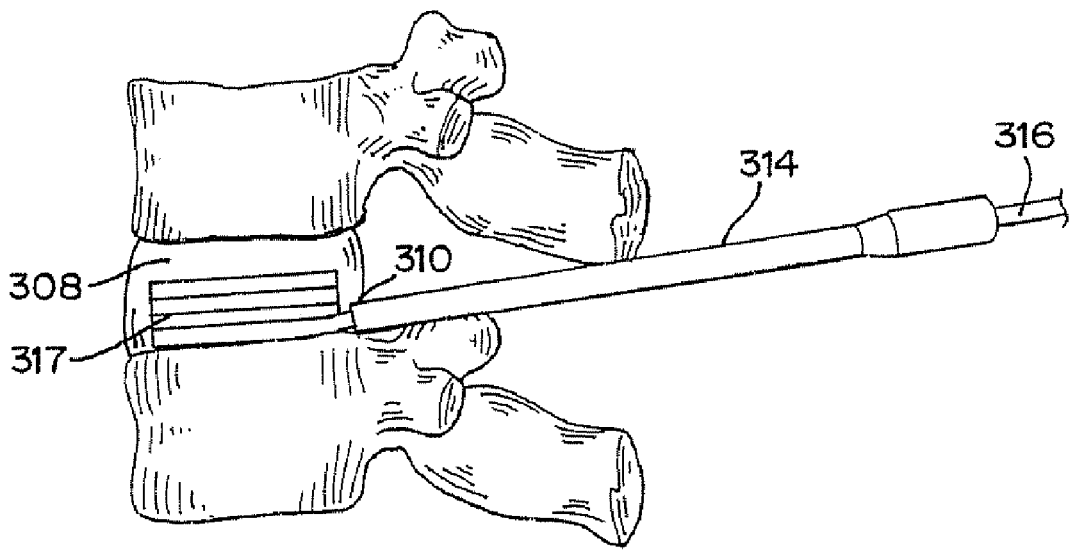
FIG. 63A is a side partial cross-sectional view of the intervertebral disk of FIG. 61 shown between superior and inferior vertebrae and with the guide wire partially deployed.

In one preferred method of delivering a distraction device in accordance with the present invention, referring to FIGS. 63 and 63A, a delivery cannula 314 is inserted through the access hole 310 and a guide wire 316 is deployed into the nucleus space 308 through the cannula 314, using similar procedures and techniques as described above. Similar to the embodiments described above, the guide wire 316 has an elongated linear configuration for delivery through the cannula and a coiled or deployed configuration upon exiting the cannula. After the guide wire 316 has been deployed, the delivery cannula 314 can be retracted and removed from the delivery system. A coiled portion 317 of the guide wire 316 is left occupying at least a portion of the nucleus space 308, as shown in FIG. 64, and a proximal end 318 of the guide wire extends from the disk 302 to define an insertion path for deployment of a distraction device.

Figure 65:
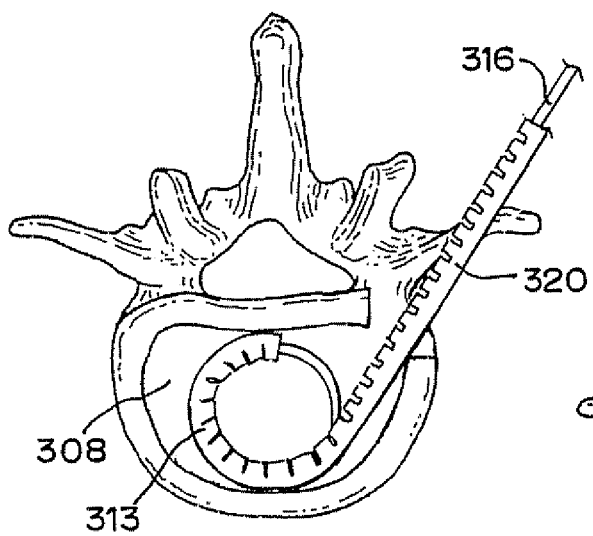
FIG. 65 is a top cross-sectional view of the intervertebral disk of FIG. 61 shown with a distraction device placed over the guide wire partially deployed within the nucleus space.
Figure 65A:
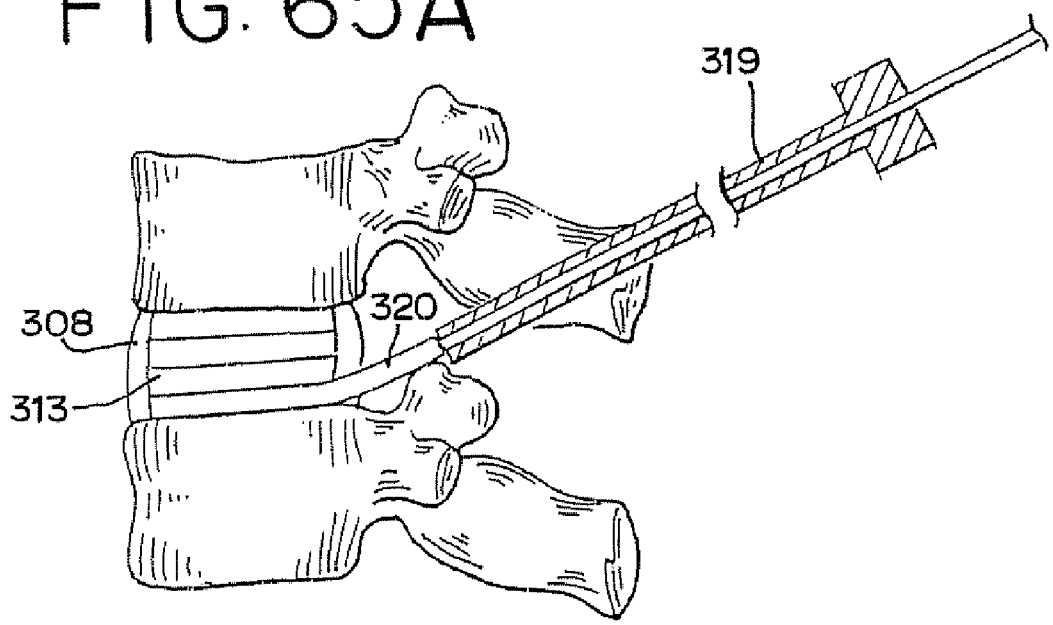
FIG. 65A is a side partial cross-sectional view of the intervertebral disk of FIG. 61 shown between superior and inferior vertebrae and with the distraction device mounted on the guide wire and partially deployed within the intervertebral disk.

As illustrated in FIGS. 65 and 65A, an implant or distraction device 320 is advanced distally over the guide wire 316. The distraction device 320 can be advanced over the guide wire 316 with the assistance of a pusher 319 or an advancing mechanism, such as the delivery ratcheting gun 292 of FIG. 58, or by any other suitable method. As the distraction device 320 advances over the guide wire 316, the guide wire guides the distraction device into the nucleus space 308. The distraction device 320 follows along the guide wire 316 and winds into a coil to form a support structure 313 substantially similar to the support structures of the previous embodiments.

Figure 66:
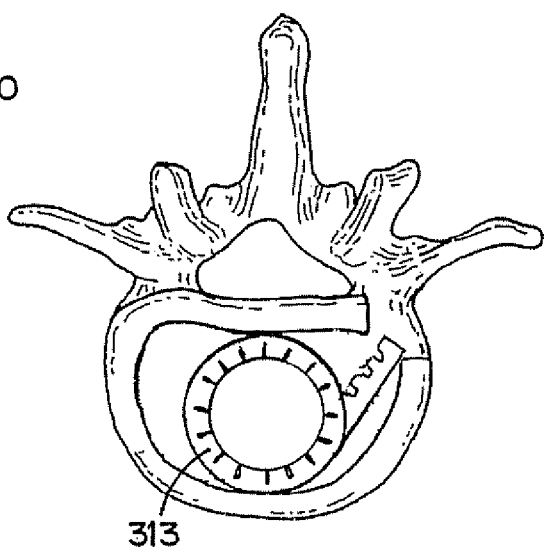
FIG. 66 is a top cross-sectional view of the intervertebral disk of FIG. 61 shown with a distraction device defining a support structured deployed within the nucleus space.

Once the distraction device has achieved the desired deployment, the delivery wire 316 can be removed leaving the support structure 313 in place as shown in FIG. 66. Alternatively, the delivery wire 316 may be severed and left within the distraction device 320. In addition to the distraction device 320, bone filler, such as bone cement or cancellous bone graft material, may be inserted around the distraction device to promoted bone fusion. The complete fusion process is expected to require about 6 months to be totally healed. If required, supplemental fixation may be added to the spine to prevent instability during the healing process.

Figure 67:
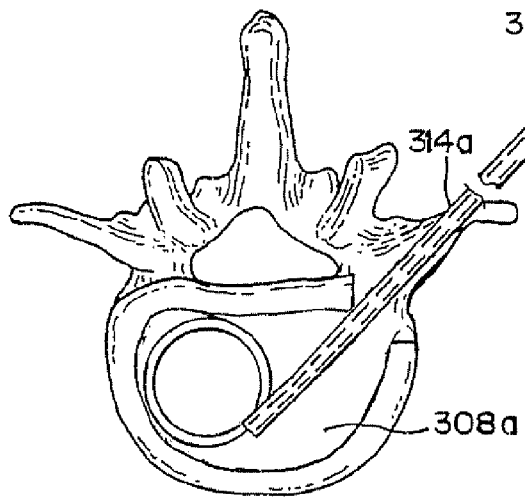
FIG. 67 is a top cross-sectional view of an intervertebral disk shown with a cannula inserted into the nucleus space and a guide wire partially deployed into the nucleus space.

An alternate deployment method in accordance with the present invention is illustrated in FIGS. 67-71. FIG. 67 illustrates an intervertebral disk in which the nucleus has already been removed. A guide wire 322a, similar to the guide wires described above, is deployed through a cannula 314a into the nucleus space 308a in a generally similar manner as described above. After the guide wire 322a has been deployed, if desired, the cannula 314a can be removed from the system. The coiled configuration of this embodiment of the guide wire has a tighter wind (smaller diameter coil), and thus occupies only a portion of the nucleus space 308a.

Figure 68:
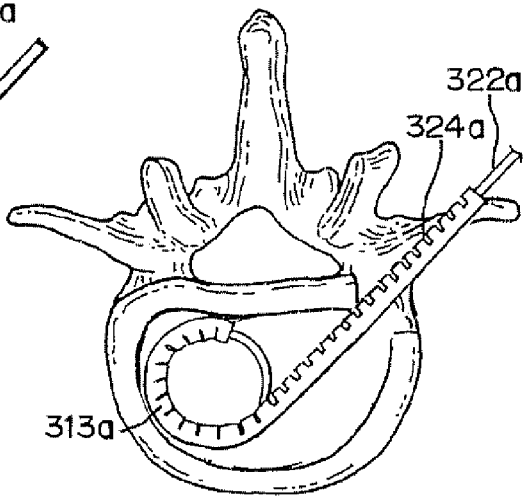
FIG. 68 is a top cross-sectional view of the intervertebral disk of FIG. 67 shown after the cannula has been removed and a distraction device partially deployed within the nucleus space.
Figure 69:
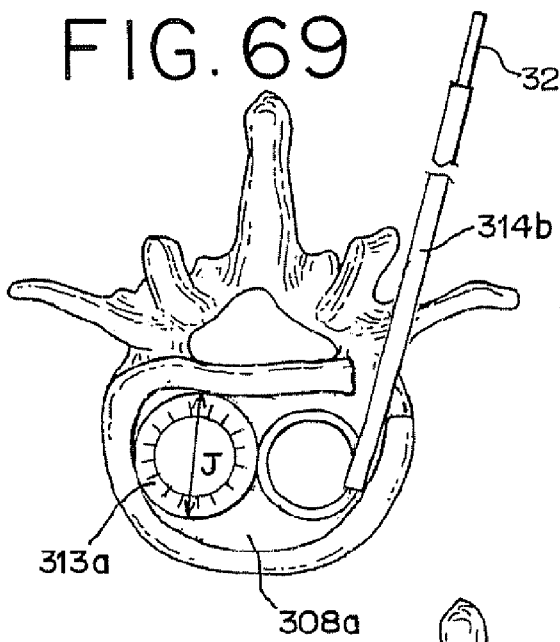
FIG. 69 is a top cross-sectional view of the intervertebral disk of FIG. 67 shown with a second cannula inserted into the nucleus space and a second guide wire deployed into the nucleus space.

As illustrated in FIG. 68, a distraction device 324a is placed over the guide wire 322a and deployed into the nucleus space 308a, in a similar manner as previously disclosed. The distraction device 324a follows along the coiled guide wire 322a and winds into a coil to form a support structure 313a as shown in FIG. 69. Because the wind of the coiled guide wire is tighter, the cross-sectional width "J" of the support structure 313a is smaller than in the previously described embodiment, and thus the support structure only occupies a portion of the nucleus space 308. After the distraction device 324a has been deployed, the guide wire 322d can be removed. Alternatively, the guide wire 322a can be severed and left within the distraction device 324a.

After the distraction device 324a has formed the support structure 313a, if there are excess portions of the distraction device, the excess portion may be severed and removed. In other words, the distraction device can be cut to length after deployment. One of the advantages of being able to cut the distraction device to length is that a single distraction device is capable of being deployed over guide wires of different radii, lengths and coil or deployment configurations.

Figure 70:
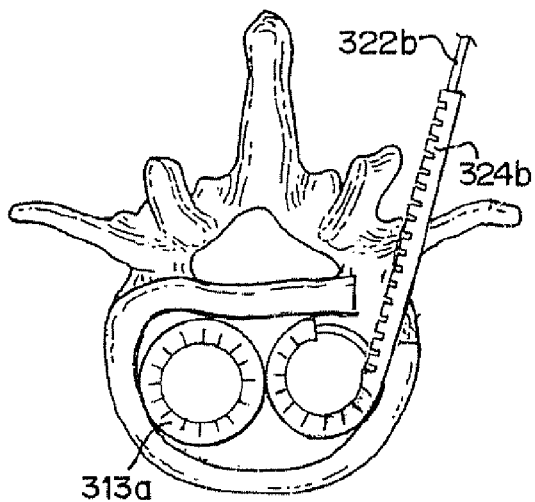
FIG. 70 is a top cross-sectional view of the intervertebral disk of FIG. 67 shown with a second distraction device placed over a delivery track and partially deployed within a nucleus space.

As shown in FIG. 69, a second guide wire 322b is deployed through a cannula 314b into the nucleus space 308a adjacent to support structure 313a. A second distraction device 324b is then deployed over the guide wire 322b, as shown in FIG. 70.

Figure 71:
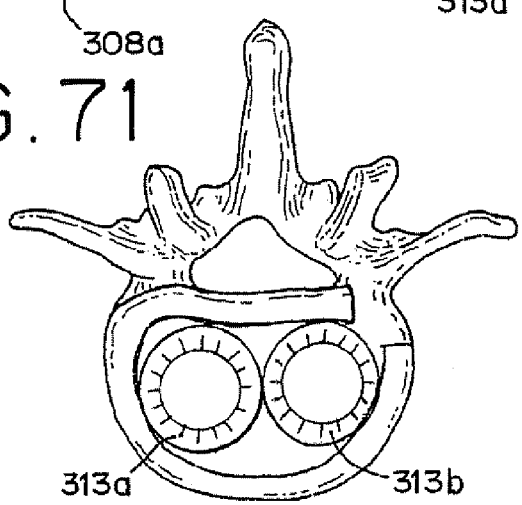
FIG. 71 is a top cross-sectional view of the intervertebral disk of FIG. 67 shown with two distraction devices deployed within a nucleus space.

FIG. 71 illustrates an intervertebral disk after the two distractions devices support structures 313a, 313b have been deployed within the nucleus space 308a. One advantage of employing two distraction devices is an increased surface area occupied by the distraction devices, which provides for aided support and distribution of forces.

Figure 60:
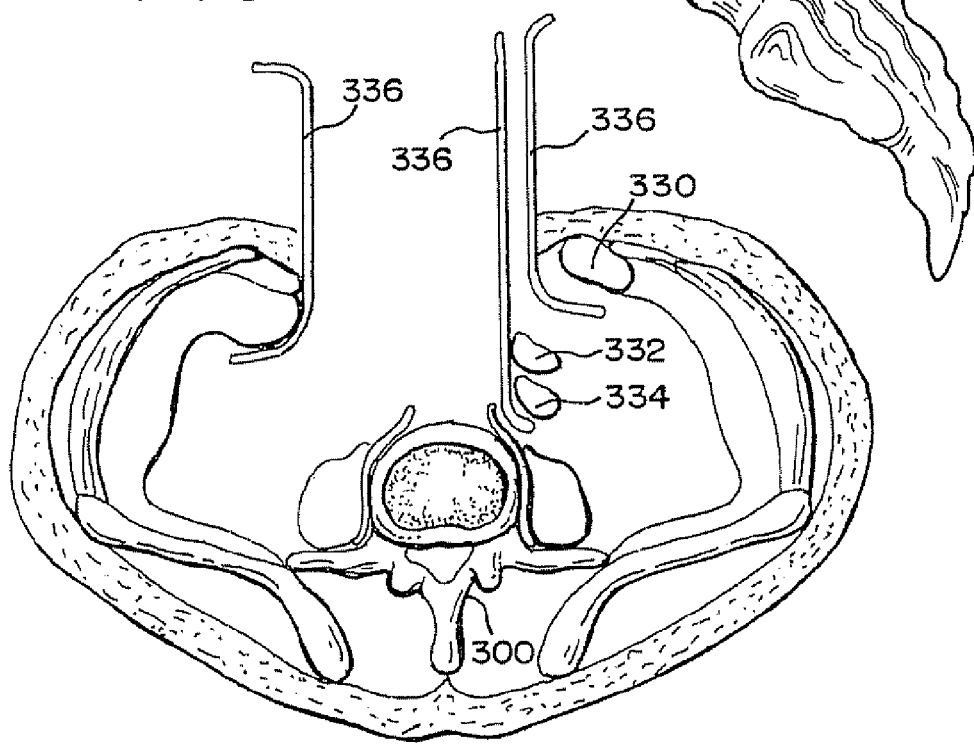
FIG. 60 is a cross-sectional view of the spinal region illustrating in example of an anterior approach which can be used for deployment of a distraction device.

The previous methods have been described for a posterior access to the spine. However, in some situations, especially in the lumbar region, an anterior approach is desired. FIG. 60 illustrates an example of an anterior approach. In such an approach, an incision is made in the belly of the patient and the main organs such as the descending colon 330, aorta 332 and inferior vena cava 334 are dissected and pushed to the side and then held by retractors 336 to provide an access to the vertebral column 300. One advantage of this approach is the ability to access the disk space from the anterior and complete a fusion when the end plates 338, 340 of adjacent vertebra are not parallel, as shown in FIG. 72, but have a wedge like shape making is difficult to insert a distraction device from the posterior approach.

In the situation where the end plates of the adjacent vertebra are not parallel it may be preferable to use a distraction device that forms a support structure having oblique ends. FIG. 74 shows one embodiment of a support structure 341 formed by a distraction device. The support structure 341 has a top portion 342 and a bottom portion 344 that are generally angled toward each other. The support structure has an anterior portion 346 and a posterior portion 348. Preferably, the anterior portion 346 is taller than the posterior portion 348, conforming the support structure to the wedge-like shape between the non-parallel vertebral plates 338, 340 as illustrated in FIG. 72B.

Figure 72A:
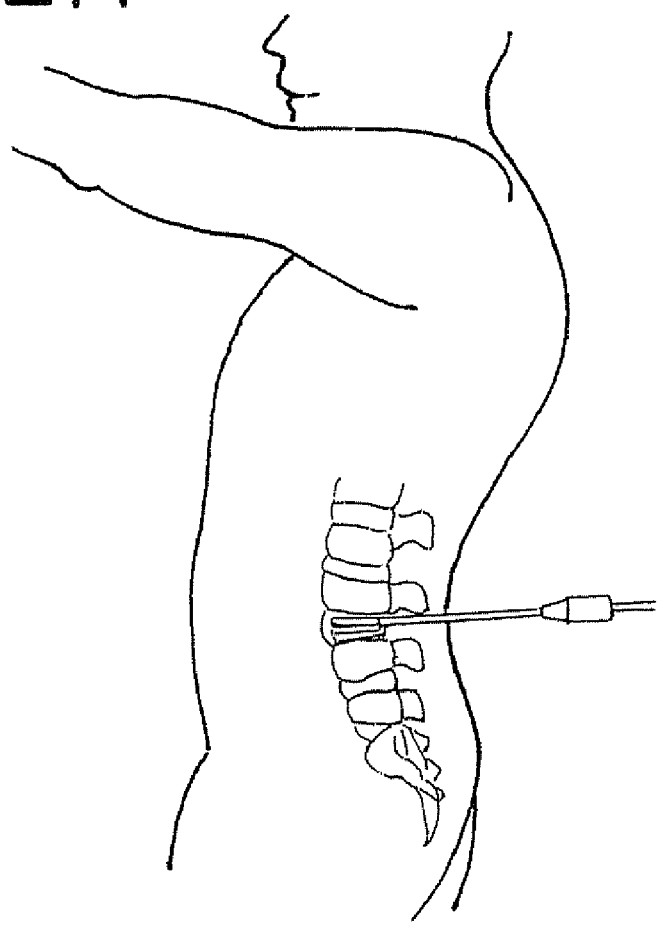
FIG. 72A is a schematic illustration of a distraction device delivery system inserted into an intervertebral disk using a posterior approach.
Figure 72B:
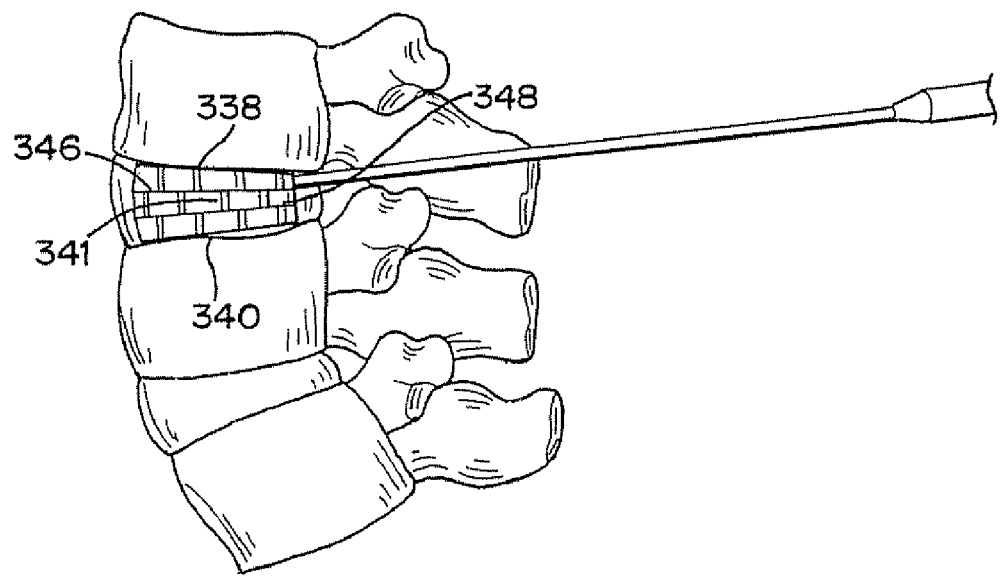
FIG. 72B is a side partial cross-sectional view of the vertebral column of FIG. 72 shown with the distraction device illustrated in FIGS. 73 and 74 partially deployed within an intervertebral disk of the vertebral column.

One advantage of an oblique configuration is that it can be used with a posterior approach as illustrated in FIG. 72A, which is much less invasive than the anterior approach just described. The posterior approach allows for a faster recovery period without sacrificing the wedge type implant desired for these particular cases.

The distraction device having an oblique configuration can be formed from the distraction device ribbon 349 as illustrated in FIG. 73. The distraction device ribbon 349 has a pre-deployed state having peaks 350 and valleys 351. Each peak 350 is spaced apart by a defined pitch "P." The peaks 350 and valleys 351 of the distraction device 349 are spaced apart so that when an appropriate guide wire is employed, the distraction device forms the support structure 341 of FIG. 73 having a longer anterior dimension. Such a support structure can be achieved by deploying distraction device 349 on a corresponding guide wire that has a coiled configuration having a radius that matches the appropriate pitch spacing.

FIGS. 75 and 76 illustrate another embodiment of the present invention wherein the deployed configuration of the guide wire 352 would have a single layer spiral portion 353. As illustrated in FIG. 76, the guide wire 352 is deployed through a cannula 355 into the open space 308b created by the removal of the disk nucleus. As the guide wire 352 exits the cannula 355, the spiral portion 353 of the guide wire forms within the nucleus space 308b. Referring to FIG. 77, the distraction device 354 is inserted over the guide wire 352 and advanced into the nucleus space 308 using methods and techniques generally similar to those previously described. The distraction device 354 follows along the guide wire 352 to create a single layered generally spiraled support structure 356. Optionally, the delivery track 352 can be removed leaving behind a well compact distraction device. FIG. 78 illustrates the distraction device support device 356 deployed in this spiral configuration. An advantage of this embodiment is to provide for a single layer of the distraction device occupying a wide area and to provide good support and stability for fusion.

Figure 79:
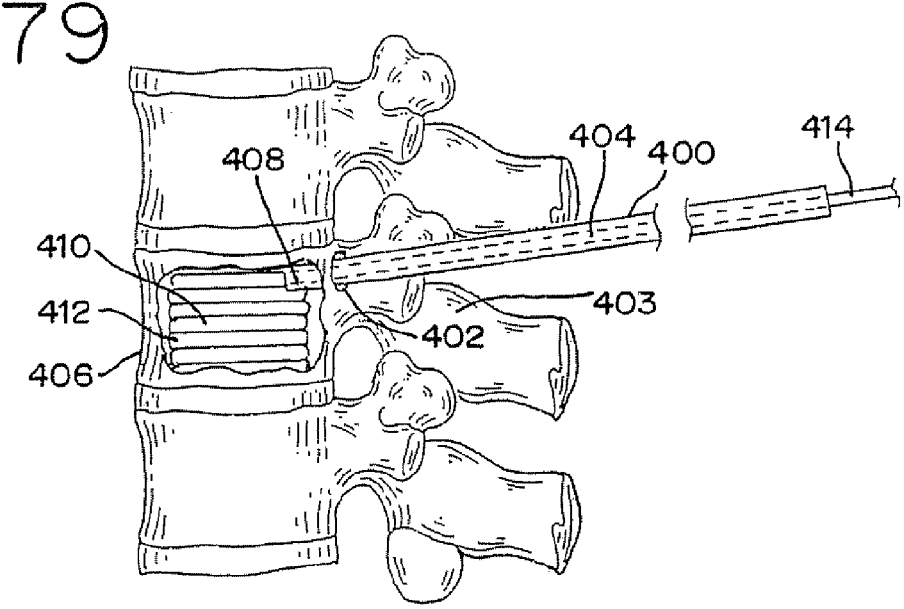
FIG. 79 is a side view of a section of a vertebral column with portions of a vertebral body broken away to show a guide wire deployed into the vertebral body via a cannula.

The distraction devices of the present invention can also be used for total or partial vertebral body replacements (VBR). In one minimally invasive partial VBR procedure of the present invention, an endoscopic procedure, generally similar to the procedure described above with respect to FIG. 26G, can be used to remove damaged vertebral body tissue. This procedure can include inserting a vertebral bone removal tool through a small access hole of the vertebral body to remove damaged portions of vertebral bone. After the damaged bone has been removed, a delivery cannula 400 can be inserted through an access hole 402, typically the same access hole created for bone removal, in vertebra 403, and a guide wire 404 is deployed into the vertebral body 406 through the cannula, as illustrated in FIG. 79.

As the guide wire 404 exits the distal end portion 408 of the cannula 400 and enters the vertebral body 406, the distal end portion 410 of the guide wire begins to return to its unconstrained coiled shape. The guide wire 404 is advanced and deployed into the vertebral body until the coil shape reaches a desired height or has the desired number of windings 412.

Figure 80:
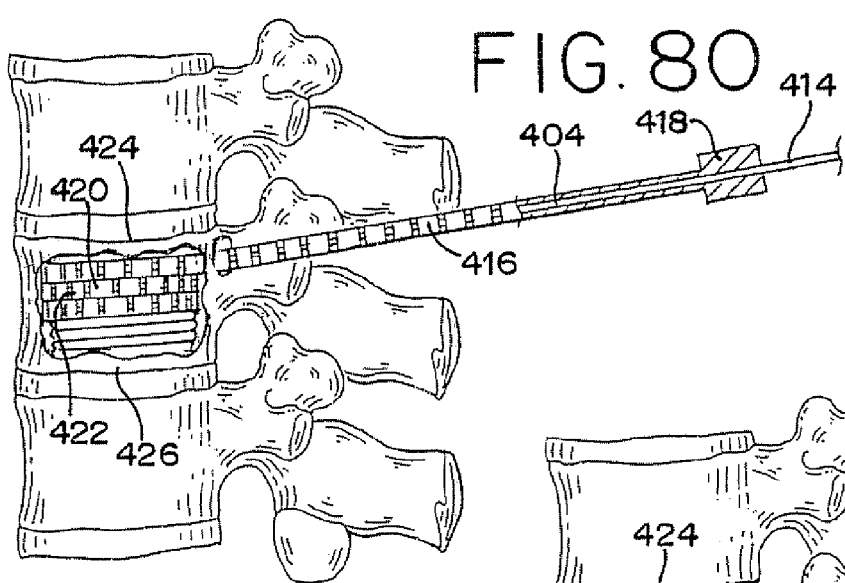
FIG. 80 is a side view of the vertebral column section of FIG. 79 with portions of the vertebral body broken away to show a distraction device being deployed into the vertebral body via a guide wire.
Figure 81:
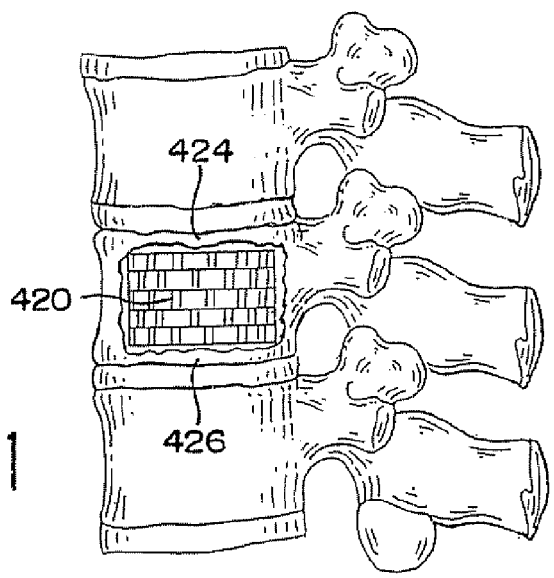
FIG. 81 is a side view of the vertebral column section of FIG. 79 with portions of the vertebral body broken away to show the distraction device deployed within the vertebral body.

After the guide wire 404 has achieved a desire deployment configuration, optionally, the cannula 400 can be retracted and removed from the system. At this stage, the coiled distal end portion 410 of the guide wire 404 is deployed within the vertebral body 406, and the proximal end portion 414 of the guide wire is extending out of the passageway 408. The proximal end portion 414 of the guide wire defines an insertion path for the distraction device 416, as illustrated in FIG. 80.

The distraction device 416 is inserted over the proximal end portion 414 of the guide wire 404, and a pusher member 418 is placed over the guide wire behind or proximal the distraction device. As the pusher member 418 is advanced, it contacts the distraction device 416 and advances it forward or distally over the guide wire 404.

In the vertebral body, the distraction device 416 follows along the coiled shaped portion 410 of the guide wire 404 and winds into a coil shaped support structure 420. With each formation of an additional coil or winding 422 of the support structure 420, the support structure increases in height or extent. As the support structure 420 increases in height, it distracts and supports the endplates 424, 426 of the vertebra, restoring or partially restoring vertebral height and stabilizing the vertebral body 406.

After the distraction device 416 has been deployed, the guide wire 404 can be retracted from the distraction device and removed from the system. Alternatively, the guide wire 404 could be severed and left within the distraction device 416. Optionally, bone filler such as bone cement, allograph or autograph, or therapeutic drugs may be inserted in or around the device, by similar methods described above, in order stabilize the device and/or to promote bone fusion.

In one minimally invasive method of a total VBR procedure, the vertebral body removal tool described above can be used to remove substantially all of the vertebral body of a vertebra 401, and a disk removal tool can used to substantially remove the adjacent disks. Referring to FIG. 82, the distal end portion 408a of the cannula 400a can be inserted into the space 430 created by the removal of the vertebral body and adjacent disk, and a guide wire 404a can be deployed into said space, using similar procedures and techniques as described above. As the guide wire 404a exits the distal end portion 408a of the cannula 400a, the distal end portion 410a of the guide wire 404a begins to return to its unconstrained coiled shape. The guide wire 404a is advanced and deployed into the space 430 created by the vertebral body and disk removal until the coil shape reaches the desired height or has the desired number of loops or windings 412a.

After the guide wire 404a has achieved a desired deployment configuration, the cannula 400a can be retracted and removed from the system. Referring to FIG. 83, the distraction device 416a is inserted over the proximal end portion 414a of the guide wire 404a, and a pusher member 418a is placed over the guide wire behind the proximal end portion of distraction device. As the pusher member 418a is advanced, it contacts the distraction device 416a and advances it forward or distally over the guide wire 404a. As the distraction device 416a is advanced over the guide wire 404a, the guide wire guides the distraction device into the space 430 created by the removal of the vertebral body and adjacent disks. As the distraction device 416a follows along the coiled shaped portion 410a of the guide wire 404a, it winds into a coiled shape support structure 420a. With each formation of the additional coil or winding 422a of the support structure 420a, the support structure increases in height. As the support structure 420a increases in height, it distracts and supports an endplate 432 of a superior vertebra 434 and an endplate 436 of an inferior vertebra 438, as shown in FIG. 84.

After the distraction device has been deployed, optionally, bone filler, such as bone cement, allograph or autograph, or therapeutic drugs may be inserted in or around the support structure to stabilize the support structure and/or to promote bone fusion.

Although the present invention is described in light of the illustrated embodiments, it is understood that this for the purposes illustration and not limitation. Other applications, modifications or use of the support or distraction device may be made without departing for the scope of this invention, as set forth in the claims now or hereafter filed.

What is claimed is:

1. An intravertebral implant system insertable into a human vertebral body having an interior region defined by a superior endplate, an inferior endplate and a cortical rim, the implant system comprising:
    at least one elongated guide member having a proximal end portion and a distal end portion, said distal end portion changeable in configuration between a pre-deployed configuration and a deployed configuration, in the pre-deployed configuration said distal end portion being sized for insertion into the vertebral body, and in the deployed configuration said distal end portion defining a pre-determined shape that is sufficiently small to reside within the interior region of the vertebral body; and
    an elongated intravertebral implant having opposed proximal and distal ends and a plurality of slots spaced apart along the intravertebral implant, the intravertebral implant including an opening at each end, a guide lumen extending between said end openings, the guide lumen slidably receiving the guide member therethrough so that the intravertebral implant may be longitudinally slidable on the guide member for advancing the intravertebral implant distally along the guide member for insertion into the vertebral body; and
    when advanced along the distal end portion of the guide member said intravertebral implant substantially conforming to the pre-determined shape defined by the distal end portion of the guide member to form a vertically extending support structure that has a transverse dimension sufficiently small to reside within the interior region of the vertebral body, and a vertical extent sufficient to separate, support or both separate and support the superior and inferior endplates.

2. The implant system of claim 1 in which the pre-determined shape of the distal end portion of the guide member in the deployed configuration defines the shape of the desired support structure.

3. The implant system of claim 1 in which the pre-deployed configuration of the guide member is generally linear.

4. The implant system of claim 1 in which the distal end portion of the guide member self-forms into the deployed configuration.

5. The implant system of claim 4 in which at least the distal end portion of the guide member is comprised of a shape memory material.

6. The implant system of claim 1 in which the pre-determined shape formed by the distal end portion of the guide member in the deployed configuration is a coil-shape including a plurality of adjacent windings.

7. The implant system of claim 1 in which the pre-determined shape formed by the distal end portion of the guide member in the deployed configuration is a spiral or helical shape.

8. The implant system of claim 1 further including a cannula for assisting in the insertion of the distal end portion of the guide member into the vertebral body.

9. The implant system of claim 1 further including an energy source that produces ultrasonic vibrations operatively connected to the guide member to aid in the insertion of the distal end portion of the guide member to the location between tissue layers.

10. The implant system of claim 1 in which the guide member is adapted to be removed from the elongated intravertebral implant after the support structure is formed.

11. The implant system of claim 1 in which elongated intravertebral implant comprises an elongated member comprised of a polymeric material.

12. The implant system of claim 1 in which the vertebral body contains cancellous bone therewithin and the support structure includes a resident volume for containing cancellous bone.

13. The implant system of claim 1 in which the elongated intravertebral implant has a cross-sectional shape that assists in enhancing the flexibility of the elongated implant.

14. The implant system of claim 1 in which the elongated intravertebral implant includes at least one passageway for the introduction of a flowable material, said passageway configured to direct movement of the flowable material to desired locations.

* * * * *

UNITED STATES PATENT AND TRADEMARK OFFICE
CERTIFICATE OF CORRECTION

PATENT NO. : 7,666,226 B2
APPLICATION NO. : 11/464790
DATED : February 23, 2010
INVENTOR(S) : Laurent Schaller It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 121 days.

Signed and Sealed this

Seventh Day of December, 2010

David J. Kappos
*Director of the United States Patent and Trademark Office*